(12) United States Patent
Hongo et al.

(10) Patent No.: US 8,563,695 B2
(45) Date of Patent: Oct. 22, 2013

(54) ANTIBODIES THAT BIND β2

(75) Inventors: Jo-Anne Hongo, Redwood City, CA (US); Jing Li, Foster City, CA (US); Victoria Smith, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 299 days.

(21) Appl. No.: 12/743,516

(22) PCT Filed: Nov. 18, 2008

(86) PCT No.: PCT/US2008/083865
§ 371 (c)(1),
(2), (4) Date: Apr. 5, 2011

(87) PCT Pub. No.: WO2009/067429
PCT Pub. Date: May 28, 2009

(65) Prior Publication Data
US 2011/0182886 A1       Jul. 28, 2011

Related U.S. Application Data

(60) Provisional application No. 60/988,874, filed on Nov. 19, 2007.

(51) Int. Cl.
*C07K 16/00* (2006.01)
*C07K 16/18* (2006.01)
*C12P 21/08* (2006.01)

(52) U.S. Cl.
USPC ............... 530/388.1; 530/388.15; 530/388.22

(58) Field of Classification Search
None
See application file for complete search history.

(56) References Cited

U.S. PATENT DOCUMENTS

2006/0259991 A1* 11/2006 Von Der Kammer et al. .. 800/12

OTHER PUBLICATIONS

Mix et al. Immunoglobulins-basic considerations. J Neurol 253 (Suppl 5): V/9-V/17, 2006.*
Datasheet for Abnova SCN2B monoclonal antibody (M01), clone 2G11-C12; catalog # H00006327-M01; online date Apr. 24, 2008.*
Coward et al. Sodium channel beta1 and beta2 subunits parallel SNS/PN3 alpha-subunit changes in injured human sensory neurons. Neuroreport 12(3): 483-488, 2001.*
Maier et al. Distinct subcellular localization of different sodium channel alpha and beta subunits in single ventricular myocytes from mouse heart. Circulation 109: 1421-1427, 2004.*
Ratcliffe et al. Sodium channel beta1 and beta3 subunits associate with neurofascin through their extracellular immunoglobulin-like domain. J Cell Biol 154(2): 427-434, 2001.*
Artavanis-Tsakonas et al., "Notch Signaling: Cell Fate Control and Signal Integration in Development" *Science* 284:770-776 (1999).
Aybar et al., "Snail precedes slug in the genetic cascade required for the specification and migration of the *Xenopus* neural crest" *Development* 130:483-94 (2003).
Batlle et al., "The transcription factor snail is a repressor of E-cadherin gene expression in epithelial tumour cells" *Nat Cell Biol.* 2:84-9 (Feb. 2000).
Bolos et al., "The transcription factor Slug represses E-cadherin expression and induces epithelial to mesenchymal transitions: a comparison with Snail and E47 repressors" *J Cell Sci.* 116:499-511 (Feb. 2003).
Bray, "Notch signalling: a simple pathway becomes complex" *Nat Rev Mol Cell Biol.* 7(9):678-89 (Sep. 2006).
Cano et al., "The transcription factor snail controls epithelial-mesenchymal transitions by repressing E-cadherin expression" *Nat Cell Biol.* 2:76-83 (Feb. 2000).
Conacci-Sorrell et al., "Autoregulation of E-cadherin expression by cadherin-cadherin interactions: the roles of beta-catenin signaling, Slug, and MAPK" *J Cell Biol.* 163(4):847-57 (2003).
Cui et al., "NB-3/Notch1 pathway via Deltex1 promotes neural progenitor cell differentiation into oligodendrocytes" *J Biol Chem.* 279(24):25858-65 (Jun. 2004).
Curry et al., "Gamma secretase inhibitor blocks Notch activation and induces apoptosis in Kaposi's sarcoma tumor cells" *Oncogene* 24(42):6333-44 (Sep. 2005).
De Strooper et al., "A presenilin-1-dependent gamma-secretase-like protease mediates release of Notch intracellular domain" *Nature* 398:518-22 (Apr. 1999).
Deangelo et al., "A phase I clinical trial of the notch inhibitor MK-0752 in patients with T-cell acute lymphoblastic leukemia/lymphoma (T-ALL) and other leukemias" *J. Clin. Oncol.* (ASCO Meeting Abstracts: 6585), 24(18S):2 pages (Jun. 20, 2006).
Eubanks et al., "Structure and chromosomal localization of the beta2 subunit of the human brain sodium channel" *Nueroreport* 8:2775-2779 (1997).
Ganguly et al., "*Drosophila* WntD is a target and an inhibitor of the Dorsal/Twist/Snail network in the gastrulating embryo" *Development* 132(15):3419-29 (Aug. 2005).
Hicks et al., "Fringe differentially modulates Jagged1 and Delta1 signalling through Notch1 and Notch2" *Nat Cell Biol.* 2(8):515-20 (Aug. 2000).
Hirata et al., "Oscillatory expression of the bHLH factor Hes1 regulated by a negative feedback loop" *Science* 298:840-3 (Oct. 2002).
Hu et al., "F3/contactin acts as a functional ligand for Notch during oligodendrocyte maturation." *Cell* 115(2):163-75 (Oct. 2003).
Huber et al.,, "Molecular requirements for epithelial-mesenchymal transition during tumor progression" *Curr Opin Cell Biol.* 17(5):548-58 (Oct. 2005).
Iso et al., "Notch signaling in vascular development" *Arterioscler Thromb Vasc Biol* 23(4):543-553 (Apr. 2003).
Isom et al., "Structure and function of the β 2 subunit of brain sodium channels, a transmembrane glycoprotein with a CAM motif" *Cell* 83:433-442 (1995).

(Continued)

*Primary Examiner* — Bridget E Bunner
(74) *Attorney, Agent, or Firm* — Julia vom Wege

(57) ABSTRACT

Compositions and methods are provided for the classification, diagnosis, treatment, and prevention of tumors characterized by loss of REST function, expression of β2, and/or activation of Notch. Further compositions and methods are provided for modulation of cellular processes such as EMT, cell migration, and apoptosis.

18 Claims, 18 Drawing Sheets

(56) References Cited

OTHER PUBLICATIONS

Jarriault et al., "Signalling downstream of activated mammalian Notch" *Nature* 377:355-8 (Sep. 1995).

Kim et al., "Presenilin/gamma-secretase-mediated cleavage of the voltage-gated sodium channel beta2-subunit regulates cell adhesion and migration" *J Biol Chem.* 280(24):23251-61 (Jun. 2005).

Lee et al., "The epithelial-mesenchymal transition: new insights in signaling, development, and disease" *J Cell Biol.* 172(7):973-81 (Mar. 2006).

Malhotra et al., "Sodium channel beta subunits mediate homophilic cell adhesion and recruit ankyrin to points of cell-cell contact" *J Biol Chem.* 275(15):11383-8 (Apr. 2000).

Nam et al., "Notch signaling as a therapeutic target" *Curr Opin Chem Biol.* 6(4):501-9 (Aug. 2002).

Nickoloff et al., "Notch signaling as a therapeutic target in cancer: a new approach to the development of cell fate modifying agents" *Oncogene* 22(42):6598-6608 (Sep. 29, 2003).

Ray et al., "Cell surface presenilin-1 participates in the gamma-secretase-like proteolysis of Notch" *J Biol Chem.* 274(51):36801-7 (Dec. 1999).

Santagata et al., "JAGGED1 expression is associated with prostate cancer metastasis and recurrence" *Cancer Research* 64(19):6854-7 (Oct. 1, 2004).

Thiery et al., "Complex networks orchestrate epithelial-mesenchymal transitions" *Nat Rev Mol Cell Biol.* 7(2):131-42 (Feb. 2006)

Timmerman et al., "Notch promotes epithelial-mesenchymal transition during cardiac development and oncogenic transformation" *Genes Dev.* 18(1):99-115 (Jan. 2004).

Westbrook et al., "A genetic screen for candidate tumor suppressors identifies REST" *Cell* 121(6):837-848 (Jun. 17, 2005).

Xiao et al., "Tenascin-R is a functional modulator of sodium channel beta subunits" *J Biol Chem.* 274(37):26511-7 (Sep. 1999)

Yang et al., "Twist, a master regulator of morphogenesis, plays an essential role in tumor metastasis" *Cell* 117(7):927-39 (Jun. 2004).

Zayzafoon et al., "Notch signaling and ERK activation are important for the osteomimetic properties of prostate cancer bone metastatic cell lines" *J Biol Chem.* 279(5):3662-70 (Jan. 2004).

Koch et al., "Notch and Cancer: a double-edged sword" Cellular and Modular Life Sciences 64:2746-2762 ( 2007).

Wu et al., "Notch Signaling and its role in breat cancer" Frontiers in Bioscience 12:4370-4383 ( 2007).

\* cited by examiner

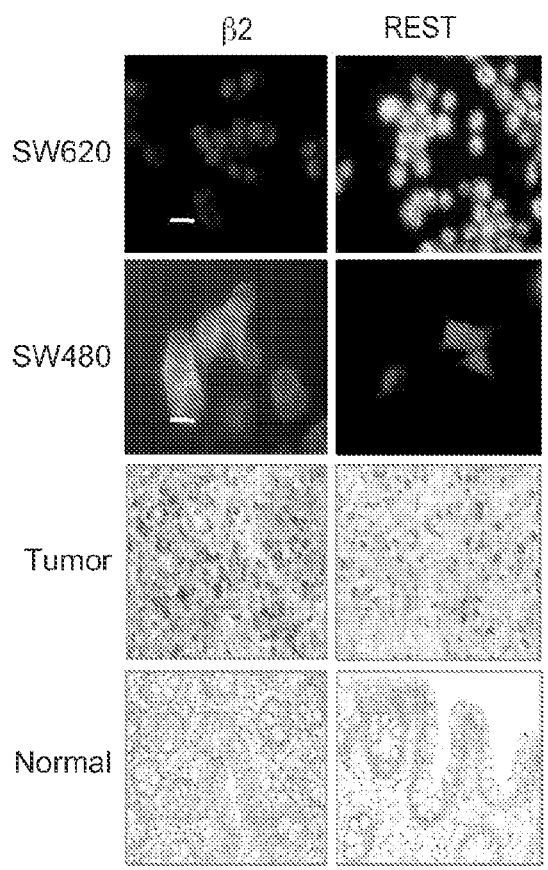
FIG. 5A
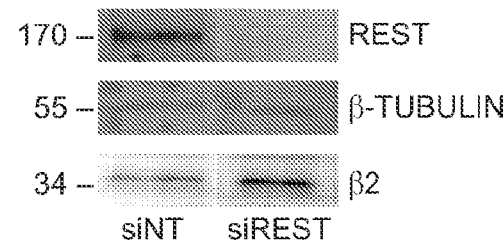
FIG. 5B
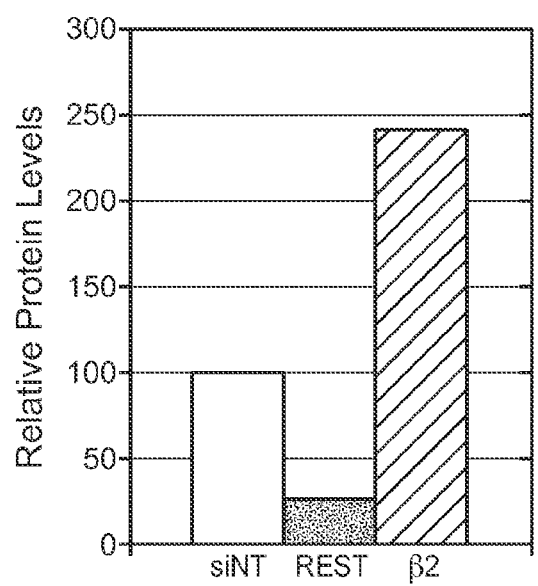
FIG. 5C siRNA Knock Down of REST

| | REST | β2 |
|---|---|---|
| SW620 | +++ | - |
| SW480 | - | ++ |
| SW1417 | - | + |
| DLD-1 | +++ | + |
| COLO205 | - | - |
| SW1116 | - | +++ |
| H460 | +++ | - |

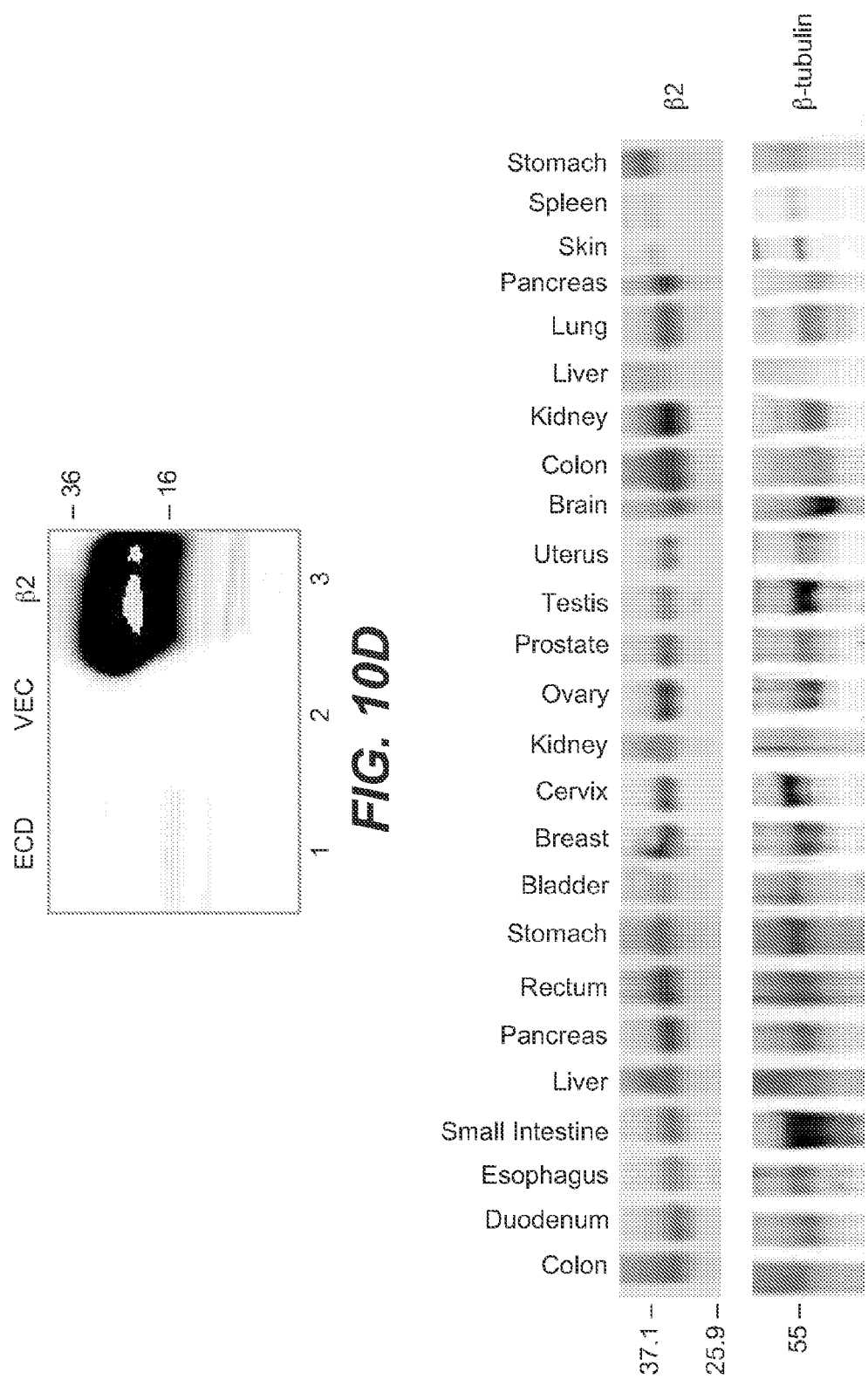

ANTIBODIES THAT BIND β2

This application is a US National Stage of PCT/US2008/083865, filed on Nov. 18, 2008, which claims the benefit of U.S. Provisional Application 60/988,874, filed Nov. 19, 2007. The entire disclosures of the foregoing applications are incorporated by reference herein.

CROSS REFERENCE TO RELATED APPLICATION

This application claims the benefit of U.S. Provisional Application No. 60/988,874, filed Nov. 19, 2007, the disclosure of which is incorporated herein by reference in its entirety.

FIELD OF THE INVENTION

The present invention relates to genes and polypeptides involved in tumor progression and other cellular processes.

BACKGROUND

EMT

During tumorigenesis, carcinoma cells lose many of their normal epithelial characteristics and acquire mesenchymal properties through a process called the "epithelial-mesenchymal transition," or EMT. EMT is associated with changes in cell adhesion and motility that promote both local invasion and metastasis to distant sites. Some genes capable of inducing EMT in model systems, such as MMP11 and TGFB1, have been described. For review, see, e.g., Huber et al., *Curr. Opin. Cell Biol.* 17:548-558, 2005; Lee et al., *J. Cell Biol.* 172:973-981, 2006; Theiry et al., *Nat. Rev. Mol. Cell Biol.* 7:131-142, 2006. However, there is a need in the art to identify further genes involved with induction of EMT in tumor cells. Such genes and their encoded proteins are useful targets, e.g., in the treatment of cancer. The invention described herein meets this need and provides other benefits.

β2

β2, which is encoded by the SCN2B gene, is a single-pass transmembrane protein with an extracellular domain containing an immunoglobulin fold similar to those found in cell adhesion proteins (Eubanks et al., *Neuroreport* 8:2775-2779, 1997; Isom et al., *Cell* 83:433-442, 1995). Originally characterized as a modulator of sodium channel properties and membrane surface area (Eubanks et al., supra), β2, along with the β1 subunit, is also capable of acting independently of the sodium channel as a cell adhesion molecule. In *Drosophila* S2 cells, the β1 and β2 subunits can bind in a trans-homophilic fashion, and with matrix proteins Tenascin C and Tenascin R via their EGF repeat motif, resulting in changes to the cytoskeleton, as well as alterations in cell adhesion and aggregation properties (Malhotra et al., *J. Biol. Chem.* 275:11383-11388, 2000; Xiao et al., *J. Biol. Chem.* 274:26511-26517, 1999). In addition, β2 has been characterized as a gamma-secretase target that induces migration in Chinese Hamster Ovary (CHO) cells (Kim et al., *J. Biol. Chem.* 280:23251-23261, 2005). These studies have also suggested that β2 undergoes ectodomain shedding mediated by an α-secretase-like protease(s). Kim et al., supra.

Notch

The Notch receptor family is a class of evolutionarily conserved transmembrane receptors that transmit signals affecting development in organisms as diverse as sea urchins and humans. Both Notch receptors and its family of ligands Delta and Serrate (the latter known as Jagged in mammals) are transmembrane proteins with large extracellular domains that contain epidermal growth factor (EGF)-like repeats. The number of Notch paralogues differs between species. For example, there are four Notch receptors in mammals (Notch1-Notch4), two in *Caenorhabditis elegans* (LIN-12 and GLP-1) and one in *Drosophila melanogaster* (Notch). Notch receptors are proteolytically processed during transport to the cell surface by a furin-like protease at a site Si external to the transmembrane domain, producing an extracellular Notch (ECN) subunit and a Notch transmembrane subunit (NTM). These two subunits remain non-covalently associated and constitute the mature heterodimeric cell-surface receptor. Notch1 ECN subunits contains 36 N-terminal EGF-like repeats followed by three tandemly repeated Lin 12/Notch Repeat (LNR) modules that precede the S1 site. Each LNR module contains three disulfide bonds and a group of conserved acidic and polar residues predicted to coordinate a calcium ion. Within the EGF repeat region lie binding sites for the activating ligands. The LNR modules, which comprise a unique domain of Notch receptors, participate in maintaining Notch in a resting conformation before ligand-induced activation. The Notch1 NTM comprises an extracellular region (which harbors the S2 cleavage site), a transmembrane segment (which harbors the S3 cleavage site), and a large intracellular part that includes a RAM domain, ankyrin repeats, a transactivation domain and a carboxy-terminal PEST sequence. Stable association of the ECN and NTM subunits is dependent on a heterodimerization domain (HD) comprising the carboxy-terminal end of the ECN (termed HD-C) and the extracellular amino-terminal end of NTM (termed HD-N). Binding of a Notch ligand to the ECN subunit initiates two successive proteolytic cleavages that occur through regulated intramembrane proteolysis. The first cleavage by a metalloprotease at site S2 renders the Notch transmembrane subunit susceptible to the second cleavage at site S3 close to the inner leaflet of the plasma membrane. Site S3 cleavage, which is catalyzed by a multiprotein complex containing presenilin and nicastrin, liberates the intracellular portion of the Notch transmembrane subunit, allowing it to translocate to the nucleus and activate transcription of target genes.

Five Notch ligands of the Jagged and Delta-like classes have been identified in humans (Jagged1 (also termed Serrate1), Jagged2 (also termed Serrate2), Delta-like1 (also termed DLL1), Delta-like3 (also termed DLL3), and Delta-like4 (also termed DLL4)). Each of the ligands is a single-pass transmembrane protein with a conserved N-terminal Delta, Serrate, LAG-2 (DSL) motif essential for binding Notch. A series of EGF-like modules C-terminal to the DSL motif precede the membrane-spanning segment. Unlike the Notch receptors, the ligands have short cytoplasmic tails of 70-215 amino acids at the C-terminus. In addition, other types of ligands have been reported (e.g., DNER, NB3, and F3/Contactin).

The Notch pathway functions during diverse developmental and physiological processes including those affecting neurogenesis in flies and vertebrates. In general, Notch signaling is involved in lateral inhibition, lineage decisions, and the establishment of boundaries between groups of cells (see, e.g., Bray, *Molecular Cell Biology* 7:678-679, 2006). A variety of human diseases, including cancers and neurodegenerative disorders, have been shown to result from mutations in genes encoding Notch receptors or their ligands (see, e.g., Nam et al., *Curr. Opin. Chem. Biol.* 6:501-509, 2002). The connection between unrestrained Notch signaling and malignancy was first recognized when a recurrent t(7;9)(q34; q34.3) chromosomal translocation, which creates a truncated, constitutively active variant of human Notch1, was identified in a subset of human acute lymphoblastic leukemias (T-ALL). In mouse models, Notch1 signaling has been shown to be essential for T cell development and that Notch1-mediated signals promote T cell development at the expense of B cell development. Also, in mouse models, excess Notch signaling during development leads to T cell neoplasia.

Moreover, Notch receptors are expressed in a wide-range of human cancers and tumor-derived cell lines and promote neural fates in human embryonic stem cells. For instance, Notch is highly expressed in neoplastic lesions in the human cervix and in human renal cell carcinoma cells. Given the involvement of Notch signaling in a wide variety of human disease it is clear that there continues to be a need for agents that regulate Notch signaling and that have clinical attributes that are optimal for development as therapeutic agents. The invention described herein meets this need and provides other benefits.

REST

REST (also called NRSF) is a transcriptional repressor of neuronal gene expression in non-neuronal tissues (Westbrook et al., *Cell:* 121:837-848, 2005). REST has been characterized as a tumor suppressor. The REST gene was identified as a frequent target of deletion in colorectal cancer. Further, a dominant negative form of REST has been identified which is capable of transforming epithelial cells. There is a need in the art to identify genes involved with REST tumor suppression. Such genes and their encoded proteins are useful targets, e.g., in the treatment of cancer. The invention described herein meets this need and provides other benefits.

SUMMARY

The invention is based, in part, on the discovery that loss of the transcriptional repressor REST leads to expression of β2, which in turn activates Notch signaling in tumors. The invention is further based, in part, on the identification of β2 as a novel ligand of Notch, whereby β2 induces EMT by binding to Notch and activating Notch signaling. These discoveries indicate that the REST/β2/Notch pathway promotes tumor progression and/or metastasis.

In one aspect, compositions and methods are provided for the classification, diagnosis, treatment, and prevention of tumors characterized by loss of REST function, expression of β2, and/or activation of Notch.

In another aspect, a monoclonal antibody that binds to β2 and blocks binding of β2 to Notch is provided. In one embodiment, the monoclonal antibody (a) is produced by a hybridoma selected from ATCC Accession Number PTA-8404, PTA-8405 and PTA-8406; (b) is a humanized form of the antibody of (a); (c) binds to the same epitope as the antibody of (a); or (d) competes with the antibody of (a) for binding to β2.

In another aspect, an isolated soluble polypeptide is provided, wherein the polypeptide comprises a fragment of Notch that specifically binds to β2.

In another aspect, a method of inhibiting tumor progression is provided, the method comprising exposing a tumor to an antagonist of β2. In one embodiment, the antagonist of β2 is an antisense nucleic acid specific for SCN2B. In one such embodiment, the antisense nucleic acid is a regulatory RNA capable of RNAi. In another embodiment, the antagonist of β2 is an antibody that binds to β2 and blocks binding of β2 to Notch. In one such embodiment, the antibody (a) is produced by a hybridoma selected from ATCC Accession Number PTA-8404, PTA-8405 and PTA-8406; (b) is a humanized form of the antibody of (a); (c) binds to the same epitope as the antibody of (a); or (d) competes with the antibody of (a) for binding to β2. In another embodiment, the antagonist of β2 is an antibody that binds to Notch and blocks binding of Notch to β2. In one such embodiment, the antibody binds within a region of Notch1 comprising EGF repeats 10-21. In another embodiment, the antagonist of β2 comprises a soluble polypeptide comprising a fragment of Notch that specifically binds to β2. In another embodiment, the tumor is metastatic. In another embodiment, the tumor is resistant to chemotherapy. In another embodiment, the tumor is a colon tumor. In another embodiment, the tumor has decreased REST activity or increased β2 activity.

In another aspect, a method of inhibiting EMT in a cell is provided, the method comprising exposing the cell to an antagonist of β2. In one embodiment, the antagonist of β2 is an antisense nucleic acid specific for SCN2B. In one such embodiment, the antisense nucleic acid is a regulatory RNA capable of RNAi. In another embodiment, the antagonist of β2 is an antibody that binds to β2 and blocks binding of β2 to Notch. In one such embodiment, the antibody (a) is produced by a hybridoma selected from ATCC Accession Number PTA-8404, PTA-8405 and PTA-8406; (b) is a humanized form of the antibody of (a); (c) binds to the same epitope as the antibody of (a); or (d) competes with the antibody of (a) for binding to β2. In another embodiment, the antagonist of β2 is an antibody that binds to Notch and blocks binding of Notch to β2. In one such embodiment, the antibody binds within a region of Notch1 comprising EGF repeats 10-21. In another embodiment, the antagonist of β2 comprises a soluble polypeptide comprising a fragment of Notch that specifically binds to β2. In another embodiment, the cell is a tumor cell. In another embodiment, the tumor cell is derived from a metastatic tumor. In another embodiment, the tumor cell is derived from a tumor that is resistant to chemotherapy. In another embodiment, the tumor cell is a colon tumor cell. In another embodiment, the cell is in vitro. In another embodiment, the cell is in vivo.

In another aspect, a method of determining whether a tumor will respond to an antagonist of β2 or an antagonist of Notch is provided, the method comprising detecting decreased REST activity or increased β2 activity in the tumor, wherein decreased REST activity or increased β2 activity in the tumor indicates that the tumor will respond to an antagonist of β2 or an antagonist of Notch. In one embodiment, the method comprises detecting decreased REST activity. In another embodiment, the method comprises detecting increased β2 activity. In another embodiment, the tumor is metastatic. In another embodiment, the tumor is resistant to chemotherapy. In another embodiment, the tumor is a colon tumor.

The above embodiments and further embodiments are provided in the description below.

Figure 1A:
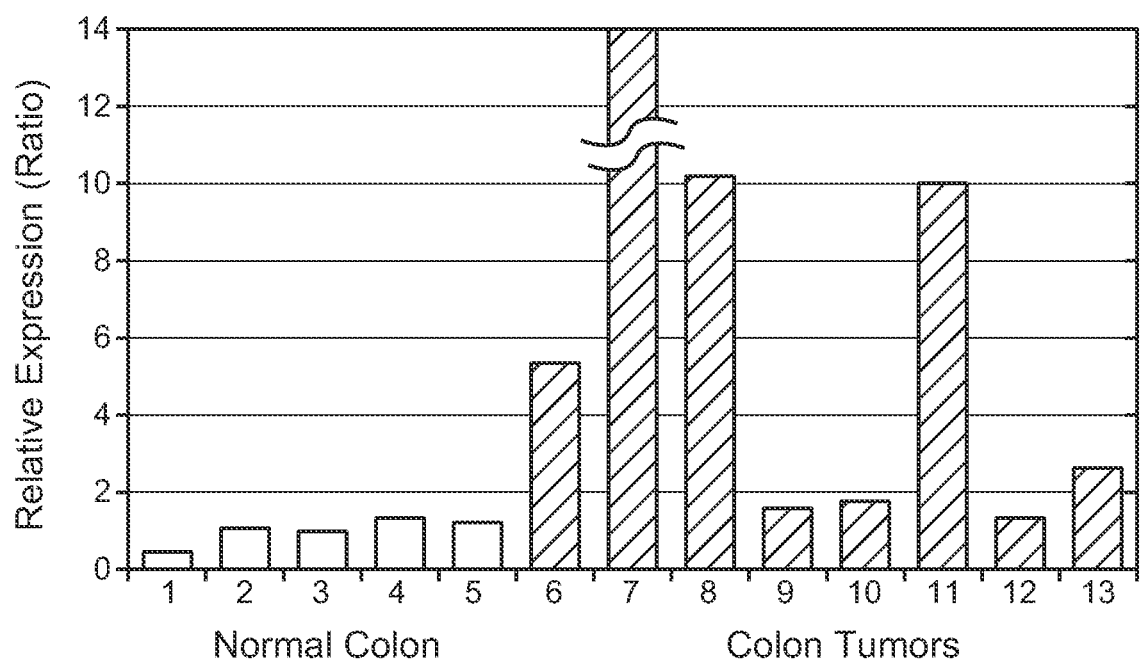
FIG. 1A

SCN2B expression in normal colon epithelium (lanes 1-5) and colon tumor epithelium (lanes 6-13). RNA was isolated following laser capture microdissection, and SCN2B expression was measured by microarray analysis. Values represent relative expression levels as a ratio of SCN2B transcript to a universal reference RNA (derived from a pool of tumor cell lines). The value of 33 for the sample in lane 7 is truncated, indicated by bars.

FIG. 1B

Examples of β2 protein expression in colon tumors and normal colon using an α-β2 monoclonal antibody (3D1).

FIG. 2A

Visualization of the actin cytoskeleton of cell lines (names on left) treated with control conditioned media (C-CM) or β2 ECD in conditioned media (β2-CM) or transfected with full length β2 (FL: β2). Images for experimental groups were collected using the same settings. The actin cytoskeleton was stained with phalloidin and nuclei with DAPI. 15 μm scale bars are indicated in lower left corner.

FIG. 2B

Antibody blocking of β2-induced phenotypic change in β2-transfectected CHO (upper 2 panels) or β2-transfectected SW620 (lower 2 panels) cells treated with antibodies against Ragweed (RW, left panels) or β2 (right panels). The actin cytoskeleton was stained with phalloidin and nuclei with DAPI. All images for experimental groups were collected using the same settings. Scale bar: 15 μm.

FIG. 2C

β2 ECD depletion assay: NCI-H226 cells were treated with control (C-CM) or β2 conditioned media (β2-CM) subjected to mock β2 depletion or partial or complete β2 depletion. The corresponding protein recovery is indicated by lane on the α-β2 immunoblot. Lane 1 contains β2 isolated from conditioned media as a positive control. The actin cytoskeleton was stained with phalloidin and nuclei with DAPI. All images were collected using the same settings.

FIG. 3A

Migration of vector-transfected (Vec) SW620 control cells or β2-transfected SW620 (FL: β2) cells, or SW620 cells treated with control conditioned medium (C-CM) or β2 ECD in conditioned medium (β2-CM), in 0.1% fetal bovine serum (FBS). No migration was observed in the absence of serum (0% FBS). Fluorescence intensity is of migrated cells stained with YO-PRO-1. Error bars represent standard deviation of mean values, derived from triplicates. A statistically significant increase in migration was observed for both β2-transfected or β2-ECD treated SW620 cells (p=0.03 and p=0.0009, respectively).

FIG. 3B

Migration of SW480 cells treated with an α-Ragweed (RW) antibody or 2 different α-β2 antibodies (3D1 or 12A9). Fluorescence intensity is of migrated cells stained with YO-PRO-1. Error bars represent standard deviation of mean values, derived from triplicates. A statically significant decrease in migration was observed in the presence of both α-β2 antibodies (p=0.001 for each).

FIG. 3C

Starvation assay: cell death of vector-transfected (Vec) SW620 control cells or β2-transfected SW620 (FL: β2) cells as a percentage of total cells after starvation. Experiments were performed in triplicate, error bars represent standard deviation of mean values. A statically significant decrease in cell death was observed for SW620 cells transfected with β2 (p=0.002).

FIG. 3D

Doxorubicin resistance in SW620 cells: cell viability (Y axis) in the presence of doxorubicin (μg/ml, X-axis) for cells transfected with vector only (Vec) or full length β2 (FL: β2). Experimental points were performed in triplicate, error bars represent standard deviation of mean values.

FIG. 3E

Methotrexate resistance in CHO cells: cell death of cells treated with control conditioned medium (C-CM) or β2 ECD in conditioned medium (β2-CM), as a percentage of total. Experiments performed in triplicate, error bars represent standard deviation of mean values. A statically significant decrease in cell death was observed for CHO cells treated with β2 ECD (p=0.01).

FIG. 4A

E-cadherin staining of SW620 control-treated cells (C-CM) or cells transfected with β2 protein (FL: β2) or treated with β2 ECD in conditioned media (β2-CM). Nuclei were stained with DAPI. All images were collected using the same settings. Scale bar: 15 μm.

FIG. 4B

FACS analysis of E-cadherin staining of SW620 in (i) cells transfected with vector (Vec) or full length β2 (FL: β2), or (ii) cells treated with control conditioned medium (C-CM) or β2 ECD in conditioned medium (β2-CM). Median ratio values were plotted and error bars represent the standard deviation of duplicates.

FIG. 4C

Vimentin staining of SW620 control-treated cells (C-CM) or cells transfected with β2 protein (FL: β2) or treated with β2 ECD in conditioned media (β2-CM). Nuclei were stained with DAPI. All images were collected using the same settings. Scale bar: 15 μm.

FIG. 4D

Twist1 depletion: actin cytoskeleton (phalloidin, upper panel) and E-cadherin (lower panel) staining of SW620 cells treated with β2 ECD in conditioned media (β2-CM) after siRNA knockdown using a non-targeting control sequence (siNT) or a siRNA targeting Twist1 (siTwist1). No change in phenotype or E-cadherin staining was detected in siNT or siTwist1 cells treated with control conditioned medium (C-CM). Images for experimental groups were collected using the same settings. Nuclei were stained with DAPI. Scale bar: 15 μm.

FIG. 4E

E-cadherin levels: quantitative analysis of E-cadherin staining in Twist1 depletion experiments for SW620 cells treated with control conditioned media (C-CM) or β2 conditioned media (β2-CM). Statistical analyses indicated that E-cadherin levels for β2-ECD treated cells depleted for Twist1 (siTwist1 and siTwist1 (3)) were significantly different compared to β2-ECD treated cells transfected with a non-targeting control (siNT) (p=0.001 and 0.009). The last set of columns, siTwist1 (3), represent a combined analysis of the data for 3 additional independent siRNA sequences targeting Twist1. At least 5 independent fields of cells were used for quantitative analysis using Metamorph as described. Error bars represent the standard error.

FIG. 5A

β2 (left column) and REST (right column) staining of SW620 and SW480 cells (top 2 panels) and in colon tumor and normal colon (bottom 2 panels). All images for an experimental group were collected using the same settings. Scale bar: 15 μm.

FIG. 5B

Immunoblot analysis of REST (upper panel) and β2 (lower panel) in SW620 following siRNA knockdown of REST (siREST) as compared to a non-targeting control (siNT). Molecular weight (KDa) is indicated on the left. The blot was also probed for β-tubulin (middle panel) as a loading control.

FIG. 5C

Relative decrease in REST protein (REST) and increase in β2 (β2) after REST knockdown using siRNA, normalized with respect to the non-targeting siRNA control (siNT, set to 100%). Values determined from Licor intensity readings of the immunoblot in 5B, background-subtracted and normalized to β-tubulin.

FIG. 5D

REST depletion: actin cytoskeleton (phalloidin, upper panel), E-cadherin (middle panel) and vimentin (lower panel) staining of SW620 cells after knockdown of REST using siRNA (siREST) or a non-targeting control (siNT), and in the presence of α-Ragweed (siREST, α-RW) or α-β2 (siREST, α-β2) antibodies. Images for all experimental groups were collected using the same settings. Nuclei were stained with DAPI. Scale bar: 15 µm.

FIG. 5E

Figure 5D:
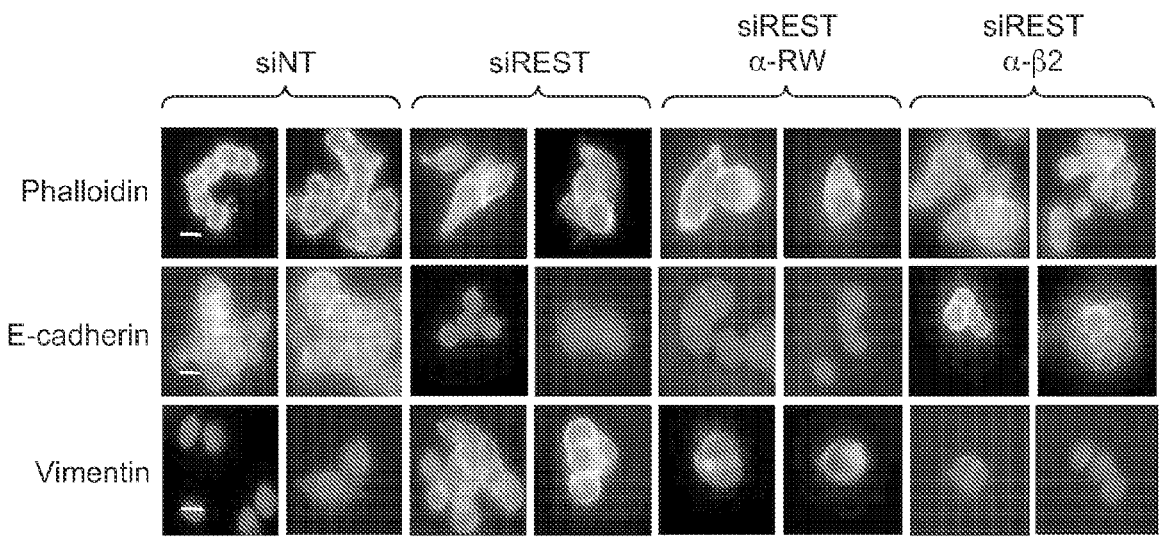

E-cadherin levels: quantitative analysis of E-cadherin staining in siREST depletion for SW620 cell experimental groupings in FIG. 5D. E-cadherin levels for cells transfected with REST-specific siRNA (siREST) were significantly decreased compared to the levels detected in cells transfected with the non-targeting control (siNT; p=0.001). REST depletion in the presence of α-β2 antibodies 3D1 (siREST:3D1) and 2E3 (siREST:2E3) resulted in wild-type levels of E-cadherin staining that were significantly increased compared to REST-depleted cells (siREST) or REST-depleted cells treated with an α-Ragweed (siREST: α-RW) antibody (p=0.02 and p=0.01). At least 5 independent fields of cells were used for quantitative analysis using Metamorph as described. Error bars represent the standard error.

FIG. 6A

Notch1 depletion: actin cytoskeleton (phalloidin, upper panel) and E-cadherin (lower panel) staining of SW620 cells treated with β2 ECD in conditioned media (β2-CM) after siRNA knockdown using a non-targeting control sequence (siNT) or a siRNA targeting Notch1 (siNotch1). No change in phenotype or E-cadherin staining was detected in siNT or siNotch1 cells treated with control conditioned medium (C-CM). Images for experimental groups were collected using the same settings. Nuclei were stained with DAPI. Scale bar: 15 µm.

FIG. 6B

Chemical inhibition of Notch signaling: E-cadherin staining of SW620 cells treated with β2 ECD in conditioned media (β2-CM) after addition of DMSO or DAPT in DMSO (DAPT). No change in E-cadherin staining was detected in cells treated with control conditioned medium (C-CM) in DMSO. Images for experimental groups were collected using the same settings. Nuclei were stained with DAPI. Scale bar: 15 µm.

FIG. 6C

E-cadherin levels: quantitative analysis of E-cadherin staining in siNotch1 depleted and DAPT-treated SW620 cells treated with control conditioned media (C-CM) or β2 conditioned media (β2-CM). Statistical analyses indicated that E-cadherin levels for β2-ECD treated cells depleted for Notch1 (siNotch1 and siNotch1(3)) were significantly different compared to β2-ECD treated cells transfected with a non targeting control (siNT) (p=0.03 and 0.03). Columns labeled siNotch1(3) represent a combined analysis of the data for 3 additional independent siRNA sequences targeting Notch1. E-cadherin levels were also significantly different for DAPT-treated cells (DAPT) treated with β2-ECD (β2-CM) compared to β2-ECD treated cells in DMSO (DMSO) (p=0.00001) At least 5 independent fields of cells were used for quantitative analysis using Metamorph as described. Error bars represent the standard error.

FIG. 7A

Co-immunoprecipitation of endogenous Notch1 in SW620 cells using α-β2 antibodies (β2: lanes 2, 3, 5, 6) or an α-Ragweed antibody (RW: lanes 1, 4) in SW620 cells transfected with vector only (Vec: lanes 1-3) or with β2 (FL: β2: lanes 4-6). The immunoblot was probed with a Notch1 polyclonal antibody (G20) and bands were detected at the expected size for this antibody (~120 kDa, indicated on the left). The level and doublet band pattern of endogenous Notch1 is shown in Lane 7, which contains an SW620 cell lysate (25 µg total protein).

FIG. 7B

Binding of Notch1 and β2 ECDs. Lanes 1 and 3 contain β2 conditioned media from CHO cells (containing His(8) tagged β2 ECD) and lanes 2 and 4 control conditioned media from CHO cells containing an irrelevant His(8) tagged protein (Gli-1). Flag-tagged Notch1 ECD protein was added to lanes 1-4 as described. Lane 5 contains 100 ng purified Notch1 ECD, Lane 6 contains 50 ng β2 ECD (expressed and purified from *E. coli*). The blot was probed for Notch1 using an α-Flag antibody (labeled Notch1, upper section of immunoblot) then stripped and re-probed for β2 using an α-β2 monoclonal antibody (3D1, labeled β2 lower section of immunoblot). Molecular weight (KDa) is indicated on the left.

FIG. 7C

Binding of Notch1 ECD fragment containing EGF repeat region 10-21 and β2 ECD. Lanes 1 and 3 contain β2 conditioned media from CHO cells (containing His(8) tagged β2 ECD) and lanes 2 and 4 control conditioned media from CHO cells containing an irrelevant His(8) tagged protein. Flag-tagged Notch1 ECD EGF repeat regions were added to lanes 1 and 2 (EGF 10-21) and lanes 3 and 4 (EGF 22-33). Lanes 5 and 6 contain 75 ng purified Notch1 ECD, EGF10-21 or EGF22-33, respectively. The blot was probed for Notch ECD using an α-Flag antibody. Molecular weight (KDa) is indicated on the left.

FIG. 7D

Translocation of Notch1 NICD to nucleus in response to β2. Notch1 NICD staining in SW620 cells transfected with vector only (Vec) or full length β2 protein (FL:β2) is shown in the left 2 panels, and NICD staining for SW620 cells treated with control conditioned medium (C-CM) or β2 ECD in conditioned medium (β2-CM) is shown in the right 2 panels. Nuclei were stained with DAPI. Scale bar: 15 µm. The lower series of panels contain enlarged regions from the images in the upper panels.

FIG. 8

Overview of proposed pathway for induction of EMT resulting from loss of REST, expression of β2, and activation of Notch pathway signaling. CDH1=E-cadherin.

FIG. 9

Anti-correlation of REST and β2 in tumor cell lines: summary of immunofluoresence analysis of tumor cell lines for REST and β2 expression. Semi-quantitative evaluation of staining indicated by +.

FIG. 10A

LCM strategy from fresh-frozen colon tumor sections with examples of a well differentiated primary colon tumor (HF3766, upper panel) and a poorly differentiated invasive primary colon tumor (HF3546, lower panel). Captured cells are outlined in the left panels.

FIG. 10B

RT-PCR analysis of β2 transcript expression in sections from samples used for LCM and microarray analysis, normalized to β-actin expression.

FIG. 10C

Non-isotopic in situ hybridization (ISH) for β2 transcript on colon tumor sections matching those used for LCM (fresh-frozen sections). Sense controls were run on matching sections and are shown for each image in the lower panel.

FIG. 10D

Detection of β2 protein on an immunoblot using an α-β2 monoclonal antibody (3D1) in SW620 transfected with vector only (VEC: lane 2) a or with full-length β2 (β2: lane 3). 25 µg of total cell protein was loaded in lanes 2 and 3. Purified β2 ECD (4 ng) was loaded in lane 1 (labeled ECD). Molecular weight (KDa) is indicated on the right.

FIG. 10E

β2 detection across human tumors by immunoblot analysis using an α-β2 monoclonal antibody (3D1, upper panel). All samples are tumor samples and the tissue of origin is listed across the top. The blot was also probed with β-tubulin as a loading control (lower panel). Molecular weight (KDa) is indicated on the left.

FIG. 11A

Staining of the actin cytoskeleton (phalloidin) for a variety of cell lines treated with β2 ECD in conditioned medium (β2-CM, right panels) or with control conditioned medium (C-CM, left panels). Cell lines (names are listed on the left): SW480, PC3, HUVEC, MDCK, HEK293. Nuclei were stained with DAPI.

FIG. 11B

Notch1 transcript expression in β2-responsive tumor cell lines SW620, SW480, NCI-H226, PC-3, and endothelial cell line HUVEC. From Affymetrix microarray data, MASS intensity values are plotted on the Y-axis.

FIG. 11C

Notch2 transcript expression in β2-responsive tumor cell lines SW620, SW480, NCI-H226, PC-3, and endothelial cell line HUVEC. From Affymetrix microarray data, MASS intensity values are plotted on the Y-axis.

FIG. 11D

Expression of other Notch ligands and receptors in SW620: Jagged1 (JAG1), Jagged2 (JAG2), Notch3, Notch4. From Affymetrix microarray data, MASS intensity values are plotted on the Y-axis.

FIG. 12A

HES1 and Twist1 transcript expression from 0-72 hours in SW620 cells treated β2 ECD in conditioned medium. RNA was extracted from cells at 0, 6, 18, 24, 48, and 72 hour timepoints and microarray analysis performed on Agilent Whole Human Genome microarrays versus a universal reference RNA. Log ratio (Y-axis) is plotted against time in hours (X-axis). Transcript data for 2 independent HES1 oligonucleotide probe sequences and for Twist1 are shown.

FIG. 12B

RT-PCR analysis of Twist1 transcript expression at 0, 6, and 18 hr timepoints in SW620 cells treated with β2 ECD. Twist1 expression was normalized to housekeeping gene RPL19.

FIG. 13A

REST depletion: RT-PCR analysis of REST (i) and β2 (ii) transcript expression in SW620 cells transfected with an siRNA specific to REST (siREST) or a non-targeting control (siNT). Transcript levels were normalized to housekeeping gene RPL19.

FIG. 13B

REST depletion: Immunofluorescence analysis of REST (upper panel) and β2 (lower panels) in SW620 cells transfected with an siRNA specific to REST (siREST: right panels) or a non-targeting control (siNT: left panels). Nuclei were stained with DAPI. All experimental groups were imaged using the same settings. Scale bar: 15 µm.

FIG. 13C

Notch1 depletion: RT-PCR analysis Notch1 transcript expression in SW620 cells transfected with an siRNA specific to Notch1 (siNotch1) or a non-targeting control (siNT). Transcript levels were normalized to housekeeping gene RPL19.

FIG. 14

Antibody blocking experiments. Five different anti-β2 antibodies were subject to competitive binding assays.

DETAILED DESCRIPTION OF EMBODIMENTS

The invention is based, in part, on the identification of β2 as a novel ligand of Notch that links loss of REST with activation of Notch signaling, thereby defining a role for β2, REST and Notch in tumor progression and metastasis.

I. DEFINITIONS

The term "β2" refers to any native sodium channel beta 2 subunit from any vertebrate source, including mammals such as primates (e.g. humans) and rodents (e.g., mice and rats), unless otherwise indicated. The term encompasses "full-length," unprocessed β2 as well as any form of β2 that results from processing in the cell. The term also encompasses naturally occurring variants of β2, e.g., splice variants or allelic variants.

The term "Notch" or "Notch receptor," as used herein, refers to any protein that belongs to the Notch family of single-pass heterodimeric transmembrane receptors. The term encompasses native Notch from any vertebrate source, including mammals such as primates (e.g. humans) and rodents (e.g., mice and rats), unless otherwise indicated. The term encompasses the mammalian Notch receptors (Notch1, Notch2, Notch3, and Notch4). The term encompasses "full-length," unprocessed Notch as well as any form of Notch that results from processing in the cell. The term also encompasses naturally occurring variants of Notch, e.g., splice variants or allelic variants.

The term "Jagged," as used herein, refers to any protein that that belongs to the Jagged (or "Serrate") family of ligands for Notch. The term encompasses native Jagged from any vertebrate source, including mammals such as primates (e.g. humans) and rodents (e.g., mice and rats), unless otherwise indicated. The term encompasses the mammalian Jagged family members termed Jagged1 (also called Serrate1) and Jagged 2 (also called Serrate 2). The term encompasses "full-length," unprocessed Jagged as well as any form of Jagged that results from processing in the cell. The term also encompasses naturally occurring variants of Jagged, e.g., splice variants or allelic variants.

The term "DLL," as used herein, refers to any protein that that belongs to the Delta-like family of ligands for Notch. The term encompasses native DLL from any vertebrate source, including mammals such as primates (e.g. humans) and rodents (e.g., mice and rats), unless otherwise indicated. The term encompasses the mammalian DLL family members termed Delta-like1 (DLL1), Delta-like3 (DLL3), and Delta-like4 (DLL4). The term encompasses "full-length," unprocessed DLL as well as any form of DLL that results from processing in the cell. The term also encompasses naturally occurring variants of DLL, e.g., splice variants or allelic variants.

The term "REST," as used herein, refers to any native repressor element 1 silencing transcription (REST) factor from any vertebrate source, including mammals such as primates (e.g. humans) and rodents (e.g., mice and rats), unless otherwise indicated. The term encompasses "full-length," unprocessed REST as well as any form of REST that results from processing in the cell. The term also encompasses naturally occurring variants of REST, e.g., splice variants or allelic variants.

The term "PRO" refers generally to any protein described herein, including but not limited to any of β2, Notch, Jagged, DLL, and REST.

An "antagonist of β2" refers to an agent that inhibits production of β2 or nucleic acid encoding β2 (e.g., SCN2B nucleic acid); that inhibits processing of β2 (e.g., release of the ECD from β2); or that interacts directly with β2 or with Notch to inhibit binding of β2 to Notch.

A "disorder" is any condition or disease that would benefit from treatment with a composition or method of the invention. This includes chronic and acute disorders including those pathological conditions which predispose the mammal to the disorder in question. Non-limiting examples of disorders to be treated herein include conditions such as cancer (e.g., colon cancer) including refractory or metastatic cancers.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" refer to disorders that are associated with some degree of abnormal cell proliferation. In one embodiment, the cell proliferative disorder is cancer.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "colorectal tumor" or "colorectal cancer" refers to any tumor or cancer of the large bowel, which includes the colon (the large intestine from the cecum to the rectum) and the rectum.

A "colorectal cancer cell" refers to a colon cancer cell or a rectal cancer cell, either in vivo or in vitro, and encompasses cell lines derived from colorectal cancer cells.

The term "colon tumor" or "colon cancer" refers to any tumor or cancer of the colon.

A "colon cancer cell" refers to a colon cancer cell, either in vivo or in vitro, and encompasses cell lines derived from colon cancer cells.

The term "neoplasm" or "neoplastic cell" refers to an abnormal tissue or cell that proliferates more rapidly than corresponding normal tissues or cells and continues to grow after removal of the stimulus that initiated the growth.

The term "epithelial-mesenchymal transition" or "EMT" refers to the process by which a cell loses epithelial properties and acquires mesenchymal properties, including but not limited to loss of cell adhesion and increased migration, that in the case of tumor cells, promote local invasion and/or metastasis.

The term "tumor progression" refers to all stages of a tumor, including tumorigenesis, tumor growth and proliferation, invasion, and metastasis.

The term "inhibiting tumor progression" means inhibiting the development, growth, proliferation, or spreading of a tumor, including without limitation the following effects: (1) inhibition, to some extent, of tumor growth, including slowing down or complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) increase in the length of survival of a patient or patient population following treatment for a tumor; and/or (7) decreased mortality of a patient or patient population at a given timepoint following treatment for a tumor.

A tumor "responds" to a particular agent if tumor progression is inhibited as defined above.

The term "antisense nucleic acid" refers to a nucleic acid that reduces expression of a target polynucleotide to which it is partially or fully complementary. An antisense nucleic acid is "specific" for a target polynucleotide if it (a) selectively binds to the target polynucleotide or its encoded mRNA and (b) reduces expression of the target polynucleotide by at least about 10%, 20%, 30%, 40%, 50%, 60%, 70%, 80%, 90%, 91%, 92%, 93%, 94%, 95%, 96%, 97%, 98%, or 99%.

The term "RNAi" or "RNA interference" refers to partial or complete inhibition of gene expression by an RNA-mediated mechanism, e.g., by a double-stranded RNA-mediated mechanism. The term "knock down" refers to such partial or complete inhibition of gene expression.

The term "regulatory RNA" or "regulatory RNA molecule" refers to an RNA capable of regulating expression of a gene, e.g., by regulating expression of the corresponding mRNA. Such regulatory RNAs include, but are not limited to, RNA capable of RNAi. A regulatory RNA is "specific" for a target polynucleotide if it (a) selectively binds to the target polynucleotide or its encoded mRNA and (b) reduces expression of the target polynucleotide by at least about 10%, 20%, 30%, 40%, 50%, 60%, 70%, 80%, 90%, 91%, 92%, 93%, 94%, 95%, 96%, 97%, 98%, or 99% when the regulatory RNA is expressed in a cell that expresses the target polynucleotide.

The term "siRNA" or "short interfering RNA" refers to a double stranded RNA that has the ability to reduce expression of a target polynucleotide when the siRNA is expressed in the same cell as the target polynucleotide. The complementary strands of an siRNA that form the double stranded RNA typically have substantial or complete identity. In one embodiment, an siRNA refers to a double-stranded RNA, one strand of which (also referred to as the "antisense" strand) has substantial or complete identity to at least a portion of a target mRNA. In certain embodiments, an siRNA is about 15-50 nucleotides in length, about 20-30 nucleotides in length, about 20-25 nucleotides in length, or 24-29 nucleotides in length, including any length that is an integer within the above-stated ranges. See also PCT/US03/07237, published as WO03076592, herein incorporated by reference in its entirety. An siRNA molecule is "specific" for a target polynucleotide if it (a) selectively binds to the target polynucleotide or its encoded mRNA and (b) reduces expression of the target polynucleotide by at least about 10%, 20%, 30%, 40%, 50%, 60%, 70%, 80%, 90%, 91%, 92%, 93%, 94%, 95%, 96%, 97%, 98%, or 99% when the siRNA is expressed in a cell that expresses the target polynucleotide.

The term "siRNA" encompasses RNA capable of forming a hairpin structure, e.g., microRNA precursors (pre-miRNA) and short hairpin RNA (shRNA). See, e.g., Brummelkamp et al. (2002) *Science* 550-553. A pre-miRNA or an shRNA is a self-complementary RNA molecule having a sense region, an antisense region, and a loop region, and which is capable of forming a hairpin structure. In certain embodiments, the sense and antisense regions are each about 15-50 nucleotides in length, about 20-30 nucleotides in length, about 20-25 nucleotides in length, or about 24-29 nucleotides in length, including any length that is an integer within the foregoing ranges; and the loop portion is about 2-15 nucleotides in length or about 6-9 nucleotides in length, including any length that is an integer within the foregoing ranges.

The term "extracellular domain" or "ECD" refers to a region of a transmembrane protein that excludes essentially all of the transmembrane and cytoplasmic domains.

The term "soluble polypeptide" refers to a polypeptide that is not membrane-bound.

A "refractory" tumor refers to a tumor that a clinician skilled in the relevant art would conclude is significantly resistant to and/or is (or is expected to be) significantly non-responsive to a therapeutic treatment (e.g., there is increased tumor volume, number of cancerous cells, and/or spreading of the cancer even though a therapeutic treatment is given). In this context, such therapeutic treatment includes, but is not limited to, chemotherapy, radiation, stem cell transplantation, and surgical treatment, excluding treatment with agonists of REST, antagonists of β2, or antagonists of Notch. The phrase "resistant to chemotherapy" refers to a tumor that a clinician skilled in the relevant art would conclude is significantly resistant to and/or is (or is expected to be) significantly non-responsive to chemotherapy, excluding chemotherapy with agonists of REST, antagonists of β2, or antagonists of Notch.

"Relapsed" refers to the regression of a patient's illness substantially back to its former diseased state following a therapeutic treatment, especially the return of symptoms (e.g., cancer cells) following an apparent recovery or partial recovery (e.g., remission) in response to the therapeutic treatment. In this context, such therapeutic treatment includes, but is not limited to, chemotherapy, radiation, stem cell transplantation, and surgical treatment, excluding treatment with agonists of REST, antagonists of β2, or antagonists of Notch.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "anti-PRO antibody" or "an antibody that binds to PRO" refers to an antibody that is capable of binding PRO with sufficient affinity such that the antibody is useful as a diagnostic and/or therapeutic agent in targeting PRO. Preferably, the extent of binding of an anti-PRO antibody to an unrelated, non-PRO protein is less than about 10% of the binding of the antibody to PRO as measured, e.g., by a radioimmunoassay (RIA). In certain embodiments, an antibody that binds to PRO has a dissociation constant (Kd) of ≤1 µM, ≤100 nM, ≤10 nM, ≤1 nM, or ≤0.1 nM. In certain embodiments, an anti-PRO antibody binds to an epitope of PRO that is conserved among PRO from different species.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and µ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816, 567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147 (1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

"Framework" or "FR" residues are those variable domain residues other than the HVR residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits a biological activity of the antigen it binds. Blocking antibodies or antagonist antibodies may substantially or completely inhibit the biological activity of the antigen.

An "agonist antibody," as used herein, is an antibody which partially or fully mimics at least one of the functional activities of a polypeptide of interest.

"Growth inhibitory" antibodies are those that prevent or reduce proliferation of a cell expressing an antigen to which the antibody binds. For example, the antibody may prevent or reduce proliferation of cancer cells in vitro and/or in vivo.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 μl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$," according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Purified" means that a molecule is present in a sample at a concentration of at least 95% by weight, or at least 98% by weight of the sample in which it is contained.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

II. EMBODIMENTS OF THE INVENTION

In various embodiments, compositions and methods are provided for the classification, diagnosis, treatment, and prevention of tumors characterized by loss of REST function, expression of β2, and/or activation of Notch. In further embodiments, compositions and methods are provided for modulation of cellular processes such as EMT, cell migration, and apoptosis. These and further embodiments of the invention are based on the discovery that loss of the transcriptional repressor REST leads to expression of β2, which in turn binds to and activates Notch signaling in tumors.

A. Compositions

Compositions are provided for the treatment or prevention of tumors, including refractory tumors. Such compositions may comprise REST agonists, β2 antagonists, and Notch antagonists, either singly or in combination.

In one aspect, a β2 antagonist is a blocking antibody that binds to β2. In one embodiment, such an antibody blocks (either partially or completely) binding of β2 to Notch. In one embodiment, a blocking antibody binds to the ECD of β2. Certain antibodies that bind to β2 are described herein and are designated 3D1.4.1 ("3D1"), 12A9.22.1 ("12A9"), 2E3.1.1 ("2E3"), 12E3, or 3G5. Also provided herein are antibodies that bind to the same epitope as do any of 3D1, 12A9, 2E3, 12E3, or 3G5, as well as antibodies that compete with any of 3D1, 12A9, 2E3, 12E3, or 3G5 for binding to β2. In one embodiment, a blocking antibody is selected from 3D1, 12A9, 2E3, or 3G5. In one embodiment, a blocking antibody binds to the same epitope as does 3D1, 12A9, 2E3, or 3G5. In one embodiment, a blocking antibody competes with any of 3D1, 12A9, 2E3, or 3G5 for binding to β2.

In certain embodiments, an antibody provided herein is a monoclonal antibody. In certain embodiments, an antibody is an antibody fragment, e.g., a Fab, Fab'-SH, Fv, scFv, or (Fab')$_2$ fragment, or a single domain antibody (Domantis, Inc., Waltham, Mass.; see, e.g., U.S. Pat. No. 6,248,516 B1). In certain embodiments, an antibody is a bispecific antibody (see, e.g., WO94/04690 and Suresh et al. (1986) *Methods in Enzymology* 121:210). In certain embodiments, an antibody is a chimeric, humanized, or human antibody. For example, humanized forms of any of 3D1, 12A9, 2E3, 12E3, or 3G5 are provided herein.

In another aspect, a β2 antagonist is a nucleic acid that decreases SCN2B expression. In one embodiment, the nucleic acid is an antisense nucleic acid specific for SCN2B. In one such embodiment, the nucleic acid is a regulatory RNA. In one such embodiment, the nucleic acid reduces SCN2B expression by RNAi. In one such embodiment, the nucleic acid is an siRNA. Certain SCN2B-specific siRNAs are known in the art. For example, certain SCN2B-specific shRNAs are commercially available (e.g., from Sigma-Aldrich, St. Louis, Mo.). Certain other β2 antagonists may be found in the art. For example, TAPI-1, a small molecule inhibitor of α-secretase, can be used to inhibit ectodomain shedding from β2. (See Kim et al., *J. Biol. Chem.* 280:23251-23261, 2005.)

In another aspect, a β2 antagonist is an isolated polypeptide, preferably a soluble polypeptide, that comprises a fragment of Notch that binds to β2. A fragment of Notch that binds to β2 would be expected to compete with endogenous Notch for binding to β2. In certain embodiments, such a fragment is substantially incapable of effecting Notch signaling. In one embodiment, a polypeptide comprises a fragment of mammalian Notch1 comprising EGF repeats 10-21 or 14-21, or a functionally equivalent fragment of a member of the Notch family, e.g., Notch2, Notch3, or Notch4. Such a functionally equivalent fragment may be routinely ascertained, e.g., by aligning the amino acid sequence of Notch1 with the polypeptide sequence of a second Notch family member to identify a corresponding fragment in the latter, and optionally, testing the fragment thus identified for β2 binding. The amino acid sequence of a human Notch is shown in SEQ ID NO:1. EGF repeats 10-21 are located in SEQ ID NO:1 at approximately the following positions:

| EGF Repeat | Amino acids |
|---|---|
| 10 | 372-410 |
| 11 | 412-450 |
| 12 | 452-488 |
| 13 | 490-526 |

-continued

| EGF Repeat | Amino acids |
|---|---|
| 14 | 528-564 |
| 15 | 566-601 |
| 16 | 603-639 |
| 17 | 641-676 |
| 18 | 678-714 |
| 19 | 716-751 |
| 20 | 753-789 |
| 21 | 791-827 |

In another embodiment, an isolated polypeptide comprises a fragment of Notch that specifically binds to β2, wherein "specifically binds," in this context, means that the fragment does not substantially bind to any other Notch ligand. In another embodiment, an isolated polypeptide comprises a fragment of Notch that binds to β2 but does not bind to Jagged and/or DLL. In another embodiment, an isolated polypeptide comprises a fragment of Notch that binds to β2 and is less than or equal to 500, 450, 400, 350, 300, 250, 200, 150, or 100 amino acids in length.

In another aspect, a β2 antagonist is an antibody that binds to a region of Notch that binds to β2. In one embodiment, the region is a region of mammalian Notch1 comprising EGF repeats 10-21 or 14-21, or a functionally equivalent region of a member of the Notch family, e.g., Notch2, Notch3, or Notch4. Such a functionally equivalent region may be routinely ascertained, e.g., by aligning the polypeptide sequence of Notch1 with the polypeptide sequence of a second Notch family member to identify a corresponding region in the latter, and optionally, testing the region thus identified for β2 binding. In certain embodiments, an antibody that binds to a region of Notch that binds to β2 specifically blocks binding of β2 to Notch, wherein "specifically blocks," in this context, means that the antibody does not block binding of any other Notch ligand to Notch. In certain embodiments, an antibody that binds to a region of Notch that binds to β2 does not block binding of Jagged and/or DLL.

In another aspect, a composition comprises a REST agonist. In one embodiment, a REST agonist is REST, including fragments or variants of full-length REST that retain a biological activity of REST (e.g., tumor suppressor activity). In another embodiment, a REST agonist is a nucleic acid encoding any of the foregoing.

In another aspect, a composition comprises a Notch antagonist. Notch activity may be antagonized by a variety of selective approaches (e.g., antisense, monoclonal antibodies, and RNAi) and non-selective approaches (e.g., soluble forms of Notch or Notch decoys, γ-secretase inhibitors, intracellular MAML1 decoys, and Ras signaling inhibitors), and various Notch antagonists are known in the art. For example, various γ-secretase inhibitors are known to inhibit Notch signaling activity. See Zayzafoon et al., *J. Biol. Chem.* 279:3662-3670, 2004 (describing the Notch-inhibiting effects of the peptidomimetic L-685,458); and Curry et al., *Oncogene* 24:6333-6344, 2005 (describing the Notch-inhibiting effects of a tripeptide aldehyde inhibitor and a peptidomimetic inhibitor (LY-411,575) of γ-secretase). MK-0752, a small molecule inhibitor of γ-secretase and an inhibitor of Notch signaling activity, is currently being tested in clinical trials. See *J. Clin. Oncol.*, 2006 ASCO Annual Meeting Proceedings Part I. Vol 24, No. 18S (June 20 Supplement), 2006: 6585.

Compositions are also provided herein for promoting EMT, cell migration, and/or resistance to apoptosis. Such compositions would be useful in a therapeutic setting, e.g., where increased cell viability and/or cell migration is desired (e.g., in wound healing). Such compositions would also be useful in a research setting. Such compositions may comprise β2 agonists, REST antagonists, or Notch agonists, either singly or in combination.

In one aspect, exemplary β2 agonists comprise β2, including fragments or variants of full-length β2 that retain a biological activity of β2 (e.g., the ability to bind Notch and/or activate Notch signaling). A β2 agonist may comprise, e.g., the ECD of β2 or a fragment or variant thereof that retains the ability to bind Notch and/or activate Notch signaling. In another embodiment, a β2 agonist is a nucleic acid encoding any of the foregoing. The amino acid sequence of a human β2 is shown in SEQ ID NO:2. The approximate locations of the following features are provided: signal peptide from amino acids 1-29; ECD from amino acids 30-159; transmembrane domain from amino acids 160-180; cytoplasmic domain from amino acids 181-215, and Ig-like domain from amino acids 32-154.

In another aspect, exemplary Notch agonists comprise Notch, including fragments or variants of full-length Notch that retain a biological activity of Notch (e.g., the ability to activate expression of target genes). For example, Notch receptors lacking extracellular subunits are constitutively activated and have transforming activity in vitro and in animal models. See Nickoloff et al., *Oncogene* 22:6598-6608. In another embodiment, a Notch agonist is an agonist antibody that binds to Notch.

In another aspect, exemplary REST antagonists include deletion mutants and other mutant forms of REST that have decreased REST activity (e.g., decreased tumor suppressor activity). See, e.g., Westbrook et al., *Cell* 121:837-848, 2005.

B. Methods

In one aspect, methods are provided herein for the treatment or prevention of tumor progression, including the progression of refractory tumors. In certain embodiments, a method for inhibiting tumor progression is provided, the method comprising exposing the tumor to one or more agents selected from an antagonist of β2, an antagonist of Notch, and an agonist of REST. Certain antagonists of β2, antagonists of Notch, and agonists of REST are discussed above and can be used in the methods described herein. In one embodiment, the agent is an antagonist of β2.

In another embodiment, the tumor has decreased REST activity. "Decreased REST activity" refers to a significant decrease in the level of REST or a significant loss of REST function (either complete or partial loss of REST function) due to, e.g., mutation in the REST gene, including but not limited to deletion of all or a portion of the REST gene, or any other event that leads to a decrease in a biological activity of REST (e.g., transcriptional repressor activity and/or tumor suppressor activity). Decreased REST activity in a tumor may be detected, e.g., by comparing the level or activity of REST in the tumor as compared to the level or activity of REST in normal tissue of the same tissue type as the tumor.

In another embodiment, the tumor has increased β2 activity. "Increased β2 activity" refers to a significant increase in the level or activity of β2 (e.g., ability to bind Notch; ability to induce EMT; ability to induce cell migration; or ability to block apoptosis). Increased β2 activity may be detected, e.g., by comparing the level or activity of β2 in a tumor as compared to the level or activity of β2 in normal tissue of the same tissue type as the tumor.

In another embodiment, the tumor has increased Notch activity. "Increased Notch activity" refers to a significant increase in the level or activity of Notch (e.g., ability to increase expression of one or more target genes, e.g., HES family genes, cell cycle regulation genes (e.g., $p21^{cip1/waf1}$, cyclin D1), NF-κB family genes, or PPAR family genes). Increased Notch activity may be detected, e.g., by comparing the level or activity of Notch in a tumor as compared to the level or activity of Notch in normal tissue of the same tissue type as the tumor.

In another embodiment, the tumor is a refractory tumor. In one such embodiment, the tumor is resistant to chemotherapy. In another embodiment, the tumor is metastatic. In another embodiment, the tumor is a colon tumor or a tumor selected from the tumor types shown in FIG. 10E. In another embodiment, the tumor occurs in a relapsed patient.

In another aspect, a method of inhibiting EMT in a cell is provided, the method comprising exposing the cell to one or more agents selected from an antagonist of β2, an agonist of REST, and an antagonist of Notch. Certain antagonists of β2, antagonists of Notch, and agonists of REST are discussed above and can be used in the methods described herein. In one embodiment, the agent is an antagonist of β2. In another embodiment, the cell has decreased REST activity, as defined above. In another embodiment, the cell has increased β2 activity, as defined above. In another embodiment, the cell has increased Notch activity, as defined above. In another embodiment, the cell is in vitro. In another embodiment, the cell is in vivo. In another embodiment, the cell is a tumor cell. In one such embodiment, the tumor cell is derived from a refractory tumor. In one such embodiment, the tumor is resistant to chemotherapy. In another embodiment, the tumor cell is derived from a metastatic tumor. In another embodiment, the tumor cell is a colon tumor cell or a tumor cell type selected from FIG. 10E. In another embodiment, the tumor cell is derived from a relapsed patient.

In another aspect, a method of inhibiting migration of a cell is provided, the method comprising exposing the cell to one or more agents selected from an antagonist of β2, an agonist of REST, and an antagonist of Notch. Certain antagonists of β2, antagonists of Notch, and agonists of REST are discussed above and can be used in the methods described herein. In one embodiment, the agent is an antagonist of β2. In another embodiment, the cell has decreased REST activity, as defined above. In another embodiment, the cell has increased β2 activity, as defined above. In another embodiment, the cell has increased Notch activity, as defined above. In another embodiment, the cell is in vitro. In another embodiment, the cell is in vivo. In another embodiment, the cell is a tumor cell. In one such embodiment, the tumor cell is derived from a refractory tumor. In one such embodiment, the tumor is resistant to chemotherapy. In another embodiment, the tumor cell is derived from a metastatic tumor. In another embodiment, the tumor cell is a colon tumor cell or a tumor cell type selected from FIG. 10E. In another embodiment, the tumor cell is derived from a relapsed patient.

In another aspect, a method of promoting apoptosis in a cell is provided, the method comprising exposing the cell to one or more agents selected from an antagonist of β2, an agonist of REST, and an antagonist of Notch. Certain antagonists of β2, antagonists of Notch, and agonists of REST are discussed above and can be used in the methods described herein. In one embodiment, the agent is an antagonist of β2. In another embodiment, the cell has decreased REST activity, as defined above. In another embodiment, the cell has increased β2 activity, as defined above. In another embodiment, the cell has increased Notch activity, as defined above. In another embodiment, the cell is in vivo. In another embodiment, the cell is a tumor cell. In one such embodiment, the tumor cell is derived from a refractory tumor. In one such embodiment, the tumor is resistant to chemotherapy. In another embodiment, the tumor cell is derived from a metastatic tumor. In another embodiment, the tumor cell is a colon tumor cell or a tumor cell type selected from FIG. 10E. In another embodiment, the tumor cell is derived from a relapsed patient.

In another aspect, a method of promoting EMT in a cell is provided, the method comprising exposing the cell to one or more agents selected from an agonist of β2, an antagonist of REST, and an agonist of Notch. Certain agonists of β2, agonists of Notch, and antagonists of REST are discussed above and can be used in the methods described herein. In one embodiment, the agent is an agonist of β2. In another embodiment, the cell is in vitro. In another embodiment, the cell is in vivo.

In another aspect, a method of promoting cell migration is provided, the method comprising exposing the cell to one or more agents selected from an agonist of β2, an antagonist of REST, and an agonist of Notch. Certain agonists of β2, agonists of Notch, and antagonists of REST are discussed above and can be used in the methods described herein. In one embodiment, the agent is an agonist of β2. In another embodiment, the cell is in vitro. In another embodiment, the cell is in vivo.

In another aspect, a method of blocking apoptosis is provided, the method comprising exposing the cell to one or more agents selected from an agonist of β2, an antagonist of REST, and an agonist of Notch. Certain agonists of β2, agonists of Notch, and antagonists of REST are discussed above and can be used in the methods described herein. In one embodiment, the agent is an agonist of β2. In another embodiment, the cell is in vitro. In another embodiment, the cell is in vivo.

In another aspect, a method of determining whether a tumor will respond to an antagonist of β2 or an antagonist of Notch is provided, the method comprising detecting decreased REST activity or increased β2 activity in the tumor, wherein decreased REST activity or increased β2 activity in the tumor indicates that the tumor will respond to an antagonist of β2 or an antagonist of Notch. In one embodiment, the method comprises detecting decreased REST activity in the tumor. In one such embodiment, the method comprises detecting a mutation in the REST gene that results in decreased REST activity. In one such embodiment, the method comprises detecting a deletion in the REST gene. In another embodiment, the method comprises detecting increased β2 activity in the tumor. In one such embodiment, the method comprises detecting increased levels of SCN2B mRNA. In another such embodiment, the method comprises detecting increased levels of β2 protein. In one such embodiment, the method comprises detecting increased levels of β2 ECD in the extracellular environment. In another embodiment, the tumor is a refractory tumor. In one such embodiment, the tumor is resistant to chemotherapy. In another embodiment, the tumor is metastatic. In another embodiment, the tumor is a colon tumor or a tumor selected from the tumor types shown in FIG. 10E. In another embodiment, the tumor is from a relapsed patient.

In another aspect, a method of assessing the prognosis of a tumor is provided, the method comprising detecting decreased REST activity or increased β2 activity in the tumor, wherein decreased REST activity or increased β2 activity indicates that the tumor has a poor prognosis. "Poor prognosis" means that there is a substantial likelihood (>50% chance) that the tumor is or will be refractory and/or metastatic. In one embodiment, the method comprises detecting decreased REST activity in the tumor. In one such embodiment, the method comprises detecting a mutation in the REST gene that results in decreased REST activity. In one such embodiment, the method comprises detecting a deletion in the REST gene. In another embodiment, the method comprises detecting increased β2 activity in the tumor. In one such embodiment, the method comprises detecting increased levels of SCNB2 mRNA. In another such embodiment, the method comprises detecting increased levels of β2 protein. In one such embodiment, the method comprises detecting increased levels of β2 ECD in the extracellular environment. In another embodiment, the tumor is a colon tumor or a tumor selected from the tumor types shown in FIG. 10E.

In another aspect, a method of classifying a tumor as one in which Notch signaling is activated, the method comprising detecting decreased REST activity or increased β2 activity in the tumor, wherein decreased REST activity or increased β2 activity indicates that the tumor is one in which Notch signaling is activated. In one embodiment, the method comprises detecting decreased REST activity in the tumor. In one such embodiment, the method comprises detecting a mutation in the REST gene that results in decreased REST activity. In one such embodiment, the method comprises detecting a deletion in the REST gene. In another embodiment, the method comprises detecting increased β2 activity in the tumor. In one such embodiment, the method comprises detecting increased levels of SCNB2 mRNA. In another such embodiment, the method comprises detecting increased levels of β2 protein. In one such embodiment, the method comprises detecting increased levels of β2 ECD in the extracellular environment. In another embodiment, the tumor is a colon tumor or a tumor selected from the tumor types shown in FIG. 10E. In another embodiment, the tumor is a refractory tumor. In one such embodiment, the tumor is resistant to chemotherapy. In another embodiment, the tumor is metastatic. In another embodiment, the tumor is from a relapsed patient.

C. Pharmaceutical Formulations and Administration

Pharmaceutical formulations comprising an agent, e.g., an antibody, protein or nucleic acid provided above in Section II.A., may be prepared according to methods generally known in the art. Such formulations may be prepared for storage by mixing the agent having the desired degree of purity with optional physiologically acceptable carriers, excipients or stabilizers (*Remington's Pharmaceutical Sciences* 16th edition, Osol, A. Ed. (1980)) in the form of aqueous solutions or lyophilized or other dried formulations. Acceptable carriers, excipients, or stabilizers are generally of low toxicity to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile. This is readily accomplished, e.g., by filtration through sterile filtration membranes.

An agent may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the active agent, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated agents remain in the body for a long time, they may denature or aggregate as a result of exposure to moisture at 37° C., resulting in a loss of biological activity and, for antibodies, possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In another aspect, methods are provided for administering an agent, e.g., an antibody, protein or nucleic acid as provided in Section II.A., above, for treatment or prophylaxis. In certain embodiments, the agent is administered in combination with at least one additional therapeutic agent and/or adjuvant. In certain embodiments, an additional therapeutic agent is a cytotoxic agent, a chemotherapeutic agent, or a growth inhibitory agent. In one of such embodiments, a chemotherapeutic agent is an agent or a combination of agents used in the treatment of colon cancer. Such agents include, but are not limited to, fluorouracil (5FU) alone or in combination with leucovorin or levamisole; edrocolomab; irinotecan; oxaliplatin; raltitrexed; and fluoropyrimidines.

Such combination therapies noted above encompass combined administration (where two or more therapeutic agents are included in the same or separate formulations), and separate administration, in which case, administration of the agent can occur prior to, simultaneously, and/or following, administration of the additional therapeutic agent and/or adjuvant. The agent can also be used in combination with radiation therapy.

An agent (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, an agent may be administered by pulse infusion, particularly with declining doses of the agent. Dosing can be by any suitable route, e.g. by injections, such as intravenous or subcutaneous injections, depending in part on whether the administration is brief or chronic.

Gene therapy methods may be used, e.g., to deliver any of the nucleic acids described herein to cells in vivo. According to one embodiment, a targeting agent is used to direct the vehicle containing the nucleic acid to a desired tissue.

Presently, there are generally two major approaches to getting a nucleic acid (optionally contained in a vector) into a mammal's cells: in vivo and ex vivo. For in vivo delivery the nucleic acid is injected directly into a mammal, usually at the sites where the nucleic acid and, if applicable, the encoded polypeptide, are desired. For ex vivo treatment, the mammal's cells are removed, the nucleic acid is introduced into these isolated cells, and the modified cells are administered to the mammal either directly or, for example, encapsulated within porous membranes that are implanted into the mammal (see, e.g., U.S. Pat. Nos. 4,892,538 and 5,283,187).

There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (including, but not limited to, retroviral) particle with a cellular receptor, followed by introduction of the nucleic acids contained in the particle into the cell. A commonly used vector for ex vivo delivery of a nucleic acid is a retrovirus.

Commonly used in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of a nucleic acid are, for example, DOTMA, DOPE, and DC-Chol; see, e.g., Tonkinson et al., *Cancer Investigation,* 14(1): 54-65 (1996)). Such vectors are used to synthesize virus that can be used as vehicles for delivering agents, such as antagonists and nucleic acid molecules of this invention. The most commonly used vectors for use in gene therapy are viruses, e.g., adenoviruses, AAV, lentiviruses, or retroviruses. In one embodiment, a viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector may include a nucleic acid molecule that is operably linked to a nucleic acid of interest and acts as a translation initiation sequence. Such vector constructs may also include a packaging signal, long terminal repeats (LTRs) or portions thereof, and positive and negative strand primer binding sites appropriate to the virus used (if these are not already present in the viral vector). In addition, such vector constructs may include a signal sequence for secretion of the encoded polypeptide from a host cell in which it is placed. Optionally, the vector construct can also include a signal that directs polyadenylation, as well as one or more restriction sites and a translation termination sequence. By way of example, vectors will typically include a 5' LTR, a tRNA binding site, a packaging signal, an origin of second-strand DNA synthesis, and a 3' LTR or a portion thereof. Other vectors that can be used are non-viral, such as cationic lipids, polylysine, and dendrimers.

In some situations, the vehicle used for delivery of a nucleic acid or other molecule is associated with a targeting agent that targets the vehicle to specific cell populations. In one embodiment, the targeting agent is an antibody specific for a cell-surface membrane protein on the target cell, a ligand for a receptor on the target cell, etc. Where liposomes are employed, proteins that bind to a cell-surface membrane protein associated with endocytosis can be used for targeting and/or to facilitate uptake. The technique of receptor-mediated endocytosis is described, for example, by Wu et al., *J. Biol. Chem.,* 262: 4429-4432 (1987); and Wagner et al., *Proc. Natl. Acad. Sci. USA,* 87: 3410-3414 (1990).

For a review of the currently known gene marking and gene therapy protocols, see, Anderson et al., *Science,* 256: 808-813 (1992). See also WO 93/25673 and the references cited therein. Suitable gene therapy and methods for making retroviral particles and structural proteins can be found in, e.g., U.S. Pat. No. 5,681,746.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

III. EXAMPLES

A. Materials and Methods

1. Detection of β2 in Tumor Tissues

Fresh frozen colon tumor tissues were sectioned at 5-10 mm on glass slides. LCM was performed using Arcturus PixCell System. Tumor cells or normal epithelia were dissected from H&E stained sections using 15 or 30 mm laser pixel size; 100-3000 cell equivalents were collected per sample. RNA was isolated and probes generated and hybridized on cDNA microarrays. Immunohistochemistry (IHC) was performed using MACH 3 Rabbit-Probe HRP polymer kit or MACH 3 Mouse-Probe HRP polymer kit from Biocare Medical (Concord, Calif.) following the manufacturer's directions. α-REST polyclonal antibody (Upstate, Lake Placid, N.Y.) or α-β2 monoclonal antibody (3D1, Genentech, Inc.) were used with human colon adenocarcinoma (grade III) and colon metastatic carcinoma tissue arrays (Cybrdi, Gaithersburg, Md.).

2. SCN2B (β2) Plasmid Constructions and Transfection

SCN2B.ECD.HIS construct: nucleic acid encoding the C-terminal polyhistidine-tagged (HIS8) ECD of SCN2B was cloned into the pSVI7 vector (DHFR) and transfected into DP12 CHO cells using Fugene 6 (Roche Diagnostics, Indianapolis, Ind.). Clones were selected in medium containing 200 nM methotrexate. β2 protein was purified from the transfected DP12 cell culture media using Ni-NTA beads (Qiagen, Valencia, Calif.) for phenotype studies, generation of monoclonal antibodies, and Notch1 binding studies. SCN2B.FL.GFP: Full-length SCN2B constructs were cloned into a pSVIPD.IRES.GFP vector (puromycin resistance marker) and transfected into CHO or SW620 cells for antibody screening and phenotype assays.

3. Cell Culture

Human tumor cell lines were maintained in RPMI1640 or F12:DMEM50:50 medium supplemented with 10% FBS, L-glutamine and Penicillin-streptomycin. CHO cells were maintained in F12:DMEM50:50 medium supplemented with 10% FBS, GHT, L-glutamine and penicillin-streptomycin. HUVEC cells were maintained in EBM-2 medium supplemented with EGM-2 (Cambrex, Valkersville, Md.).

4. Immunoblot Analysis

Cells were lysed in lysis buffer (100 mM $NaH_2PO_4$, 10 mM Tris-HCL, 8M Urea and 0.05% tween-20, pH 8.0) with sonication and the lysate (typically 25 μg total protein) was loaded onto 4-12% Tris-Glycine gel (Invitrogen). Proteins were transferred onto PVDF membrane (Invitrogen, Carlsbad, Calif.) or Nictrocellulose membranes (Invitrogen). Immunoblots were blocked overnight at 4° C. in 2% BSA, 5% dry milk in PBS. The following antibodies were used: mouse α-β2 monoclonal or rabbit α-β2 polyclonal (Genentech, Inc.), α-REST polyclonal antibody (Upstate, Lake Placid, N.Y.), α-Notch1 (G20) polyclonal antibody (Santa Cruz Biotechnology, Santa Cruz, Calif.), α-FLAG antibody (Sigma). Secondary detection was performed using IRDye680-conjugated goat α-mouse IgG or IRDye680-conjugated donkey α-rabbit IgG (Rockland Inc., Gilbertsville, Pa.). Immunoreactive bands were detected and analyzed by scanning the blot with Odyssey Infrared Imaging System (LI-COR Biosciences, Lincoln, Nebr.). Alternatively, secondary detection was performed using ECL α-mouse IgG HRP (Amersham) and detected using Chemiglow West (Alpha Innotech).

5. Generation of β2 Antibodies

Five Balb/c mice (Charles River Laboratories, Hollister, Calif.) were hyperimmunized with recombinant polyhistidine-tagged (HIS8) human β2 ECD from CHO cells (Genentech, Inc., South San Francisco, Calif.) in Ribi adjuvant (Ribi Immunochem Research, Inc., Hamilton, Mo.). B-cells from these mice, all of which demonstrated high α-β2 antibody titers by direct ELISA and specific binding to β2 expressed on CHO cells by FACS, were fused with mouse myeloma cells (X63.Ag8.653; American Type Culture Collection, Rockville, Md.) using a modified protocol analogous to one previously described (Kohler and Milstein, *Nature* 256:495-497, 1975; Hongo et al., *Hybridoma* 14:253-260, 1995). After 10-12 days, the supernatants were harvested and screened for antibody production by direct ELISA and FACS. Clones showing the highest immunobinding after the second round of subcloning were expanded and cultured. The supernatants harvested from each hybridoma lineage were purified by affinity chromatography (Pharmacia fast protein liquid chromatography [FPLC]; Pharmacia, Uppsala, Sweden) using a modified protocol analogous to one previously described (Hongo et al., supra). The purified antibody preparations were then sterile filtered (0.2-μm pore size; Nalgene, Rochester N.Y.) and stored at 4° C. in phosphate buffered saline (PBS).

6. Immunofluoresence

Vimentin and actin cytoskeleton (rhodamine-phalloidin): cells were fixed in 4% paraformaldehyde for 20 minutes at room temperature and permeabilzed with 0.05% saponin for 5 minutes at room temperature. For β2, REST, cleaved-Notch1 NICD and E-cadherin staining: cells were fixed in methanol at 4° C. for 2 minutes. Primary antibody incubation was at room temperature for 1 hour (for vimentin staining), or for 15 minutes (for rhodamine-phalloidin staining) or at 37° C. for 1 hour (for β2, REST, cleaved-Notch1 NICD and E-cadherin staining). Secondary antibody incubation was at room temperature for 30 minutes. Antibodies used were as following: α-ankyrin monoclonal antibody (Chemincon International, Temecula, Calif.); α-vimentin monoclonal antibody (Sigma-Aldrich, St. Louis, Mo.); rhodamine-phalloidin (Molecular Probes, Eugene, Oreg.), α-REST polyclonal antibody (Upstate, Lake Placid, N.Y.), α-E-cadherin monoclonal antibody (Invitrogen, Carlsbad, Calif.), α-Notch1 (Val1744 peptide, detects both intact and cleaved Notch1 NICD) (Cell Signaling, Danvers, Mass.) or α-β2 monoclonal antibody (Genentech, Inc.). Secondary antibodies were as follows: Cy3-conjugated rabbit α-mouse IgG or Cy3-conjugated donkey α-rabbit IgG (Jackson Lab, Bar Harbor, Me.). Slides were mounted with Vectashield mounting media with DAPI (4',6-diamidino-2-phenylindole) (Vector Lab, Burlingame, Calif.). Images were acquired using 60× magnification on a microscope equipped with a camera. Images overlays were generated using Adobe Photoshop software. For intact or cleaved Notch1 NICD staining, after the secondary antibody incubation, slides were incubated with Hoechst 44257 to stain nuclei at room temperature for 20 minutes, and mounted with Prolong Gold anti-fade reagent (Invitrogen, Carlsbad, Calif.). Images were acquired using a LSM510 laser scanning confocal microscope (Carl Zeiss Micro Imaging, Inc., Thornwood, N.Y.). Two-photon excitation by a Chameleon laser (Coherent, Santa Clara, Calif.) was used for DAPI visualization, with a fully open pinhole. A HeNe (543 nm) laser was used for the fluorochrome excitation, with the pinhole set to one Airy unit. Images were saved in TIFF format and assembled in Photoshop.

7. β2 and β2 ECD Induced Phenotype Assays

CHO cells expressing β2 ECD were grown to 80% confluence and media was collected and centrifuged to remove any cell debris. This conditioned media was used to treat cell lines for the described analyses. Media collected from vector-transfected CHO cells was used as a control. For phalloidin, vimentin and E-cadherin staining, condition media treated cells were stained with antibodies at 48 or 72 hours.

8. Antibody Blocking Assay

SCN2B and vector transfected CHO cells and SW620 cells were seeded onto 1-well chamber glass slides (Nalge Nunc International, Rochester, N.Y.) at 25% confluence. α-β2 monoclonal antibody was added to the cell culture media at 100 ng/ml. After 72 hours, cells were stained with rhodamine phallodin.

9. β2 Depletion Assay

α-β2 monoclonal antibody-coupled gel was made using Seize Primary Immunoprecipitation Kits (Pierce, Rockford, Ill.) following manufacturer's instructions. Cell culture media collected from DP12/SCN2B.ECD.HIS cells was incubated with α-β2 monoclonal antibody-coupled gel for 2 hours to remove β2. The flow through was added to cells for phenotype analysis. A mock depletion of β2 was done with PBS-coupled gel using the same procedure. β2 was also depleted using Ni-NTA beads (Qiagen).

10. Migration Assay

Migration assays were performed using the HTS FluoroBlock Multiwell insert system with 8 mm pore size (BD Biosciences, Bedford, Mass.). $10^5$ cells/well were seeded into the upper wells and FBS was added to the bottom wells. After 18 hr, cells that migrated to the other side of the trans-well membrane were stained in 10 um YO-PRO-1 iodide (Invitrogen, Eugene, Oreg.) and quantitated using the fluorescence plate reader Spectra Max GeminiEM (Molecular Devices, Sunnyvale, Calif.).

11. Cell Death and Drug Resistance:

Resistance to starvation: SW620 cells were seeded into 6 well plates at 25% confluence in complete media overnight. This media was replaced the next morning with media lacking FBS. For the assay, cells were detached using trypsin, washed, and stained in 0.4% Trypan Blue (Invitrogen, Carlsbad, Calif.). Total cells and dead cells were counted using a hemocytometer. Assays were performed in triplicate. Doxorubicin resistance: $2\times10^4$ SW620 cells were seeded in 96 well clear bottom black plates (Corning Inc., Corning, N.Y.) with serial dilutions of doxorubicin hydrochloride (Sigma-Aldrich, St. Louis, Mo.) and incubated for 5 days. Cell viability was measured by using Cell Titer Glo Luminescent Cell Viability Kit (Promega, Madison, Wis.). Luminescence was quantified using an Envision 2103 multilabel reader (PerkinElmer, Finland). Methotrexate resistance: $5\times10^5$ CHO cells were seeded in 6-well plates with β2 ECD in conditioned medium or control conditioned medium containing 200 nm methotrexate (Genentech Inc.). Cells were detached from the plate and stained with Trypan Blue 0.4% (Invitrogen, Carlsbad, Calif.) as described.

12. siRNA Knock Down siRNA knock down of REST, Twist1 or Notch1 in SW620 cells was performed using 60 nm of siRNA with DharmaFECT 2 as the transfectant. A non-targeting siRNA sequence (Dharmacon, Lafayette, Colo.) was used as a negative control. Immunofluoresence staining and RT-PCR analysis were performed 4 days after siREST transfection. For Twist1 and Notch1 knock downs, cells were treated with β2 ECD in conditioned media 24-48 hours after transfection, followed by immunofluoresence staining or RT-PCR analysis after an additional 24-48 hours of incubation. For siREST experiments, α-β2 antibodies were added after 12 hours after transfection. The siRNA duplexes were designed and synthesized by Dharmacon (Lafayette, Colo.). The primary target sequences are as follows:

```
siREST:
                                        (SEQ ID NO: 3)
5'-CAACGAAUCUACCCAUAUUUU-3'.

siTwist1:
                                        (SEQ ID NO: 4)
5'-GCGACGAGCUGGACUCCAAUU-3'.

siNotch1:
                                        (SEQ ID NO: 5)
5'-GCGACAAGGUGUUGACGUUUU-3'.

Additional siRNA sequences: siTWIST1:
                                        (SEQ ID NO: 6)
5'-CUGCAGACGCAGCGGGUCAUU-3', (SEQ ID NO: 7)
5'-GGAGUCCGCAGUCUUACGAUU-3', (SEQ ID NO: 8)
5'-GAGCAAGAUUCAGACCCUCUU-3';

SiNOTCH1:
                                        (SEQ ID NO: 9)
5'-GAUGCGAGAUCGACGUCAAUU-3', (SEQ ID NO: 10)
5'-GAACGGGGCUAACAAAGAUUU-3', (SEQ ID NO: 11)
5'-GCAAGGACCACUUCAGCGAUU-3'.
```

13. Image Processing for E-Cadherin Intensity Calculations

Images were converted from Photoshop format to Tif in Photoshop CS2 (version 9.0.2, Adobe; San Jose, Calif.). Images were opened in Metamorph (version 7.0r4, Molecular Devices; Sunnyvale, Calif.) and subjected to an automated analysis routine. Briefly, a threshold value was applied for each set of images (approx. 10-15% of maximum pixel value) to remove background. A standard erode function was used to further reduce background and smoothen the edges of the remaining regions. Area and intensity measurements for each individual region were output directly to Excel (Microsoft, Redmond, Wash.). A small subset of images had specific staining that was above background, but below the threshold value. For this subset, regions of interest were created manually in order to obtain area and intensity measurements. Typically, 5 independent regions were analyzed and combined for each analysis.

14. Statistical Analysis

Analyses were performed in triplicate (or greater) and analyzed using a Student's T-test (equal variance, 1 tailed distribution) in Microsoft Excel.

15. Binding Assays

Immunoprecipitation: cells were removed from culture plates using 5 mm EDTA and lysed in TBS buffer containing 0.5% NP-40, EDTA-free protease inhibitor (Roche Diagnostics, Indianapolis, Ind.) and 1 mm PMSF. The cell lysate was incubated with pre-saturated protein G-agarose (Roche Diagnostics, Indianapolis, Ind.) at 4° C. for 1.5 hour followed by incubation with α-β2 monoclonal antibody at 4° C. for 2 hours. This cell lysate and antibody mixture was then incubated with pre-saturated protein G-agarose at 4° C. overnight. The agarose was collected and proteins were eluted in Tris-Glycine gel loading buffer (Invitrogen, Carlsbad, Calif.) for immunoblot analysis. Direct binding: conditioned media was collected as described above, incubated with FLAG-tagged Notch1 ECD:6-36 (5 μg) in 15 ml for 2 hours at room temperature with shaking 50 μl of Ni-NTA agarose bead slurry (Qiagen) was added with incubation for 2 hours at room temperature with shaking. Ni-NTA beads were collected by centrifugation and washed 3 times with PBS. Alternatively, conditioned media was treated with Ni-NTA beads to enrich for β2 and the resulting slurry incubated with Notch1 ECD: 6-36 (5 μg) in 1 ml PBS and incubated and washed as described. Samples were eluted into 2× loading buffer.

16. Microarray Analysis

Microarrays representing 9031 genes were generated by printing PCR products derived from cDNA clones (Invitrogen, Carlsbad, Calif. and Genentech, Inc.) on glass slides coated with 3-aminopropyltriethoxysilane (Aldrich, Milwaukee Wis.) and 1,4-phenylenediisothiocyanate (Aldrich, Milwaukee, Wis.) using a robotic arrayer (Norgren Systems, Mountain View, Calif.). RNA isolation from LCM material was accomplished by CsCl step gradient (Kingston R E, in *Current Protocols in Molecular Biology*, Vol. 1 (ed. Ausubel F M, et al.) 4.2.5-4.2.6 (John Wiley and Sons, Inc., USA, 1998)). Probes for array analysis were generated by conservative amplification and subsequent labelling as follows: double-stranded DNA generated from oligo dT priming of total RNA (Invitrogen, Carlsbad, Calif.) was amplified using a single round of a modified in vitro transcription protocol (MEGAScript T7 from Ambion, Austin, Tex.). The resulting cRNA was used as a template to generate a sense DNA probe using random primers (9mers, 0.15 mg/ml), Alexa 488 dUTP or Alexa 546 dUTP (40 μM and 6 μM, respectively, Molecular Probes, Eugene, Oreg.) using MMLV-derived reverse transcriptase (Invitrogen, Carlsbad, Calif.). A reference probe to reflect general epithelial cell expression was generated from 0.1 μg of total RNA from a universal reference RNA (Strategene, La Jolla, Calif.). Probes were hybridized to arrays overnight in 50% formamide/5×SSC at 37° C. and washed the next day in 2×SSC, 0.2% SDS followed by 0.2×SSC, 0.2% SDS. Array images were collected using a CCD-camera based imaging system (Norgren Systems, Mountain View, Calif.) equipped with a Xenon light source and optical filters appropriate for each dye. Full dynamic-range images were collected (Autograb, Genentech Inc) and intensities and ratios extracted using automated gridding and data extraction software (gImage, Genentech, Inc.) built on a Matlab (the MathWorks, Natick, Mass.) platform.

17. Microarray Data Analysis

Ratio values were normalized for experimental scatter at different intensity values within each experiment by plotting log ratio versus N intensity and by fitting a normal distribution at each intensity level. A measure of standard deviation (Z score) around a mean of zero was derived for each transcript in each experiment and this value was used in data mining. Specifically, for each microarray, we normalized the data by computing Z-scores, which were obtained from a scatterplot of the logarithm of the ratio of the test and reference data versus the logarithm of the minimum of the test and reference data. We estimated the median of the ratio as a function of intensity by applying the loess algorithm to the scatterplot. We estimated the standard error by applying loess to the square root of the absolute residuals, and squaring the result to obtain the median absolute deviation (MAD), and making a multiplicative correction to convert from MAD to a standard error. The Z scores were determined for each ratio by dividing its vertical distance from the median loess curve by the standard error at that intensity. Genes that were differentially expressed between tumor and normal epithelium were identified using a statistical test (Student's T test, equal variance, two-tailed distribution) in Rosetta Resolver.

B. Results

1. β2 is Expressed in Tumors

We discovered β2 expression in colon tumor cells through microarray expression profiling of laser capture microdissected material, a technique with demonstrated utility in isolating discrete cell populations from complex tissues and disease states such as tumors, allowing identification of gene expression not previously associated with these cells (Buckanovich et al., *Cancer Biol. Ther.* 5:635-642, 2006; Espina et al., *Methods Mol. Biol.* 319:213-229, 2006)

Figure 10A:
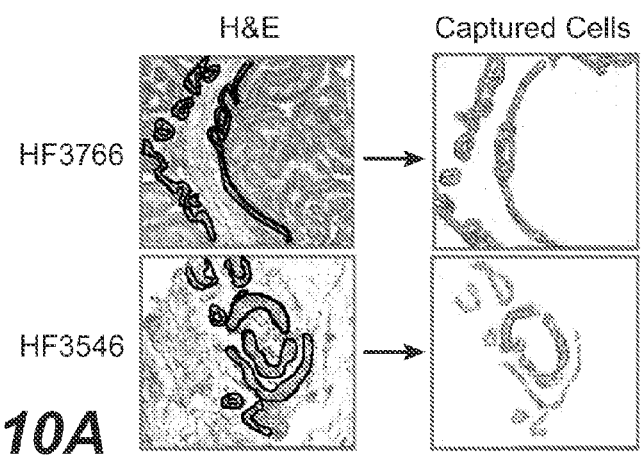
Figure 10B:
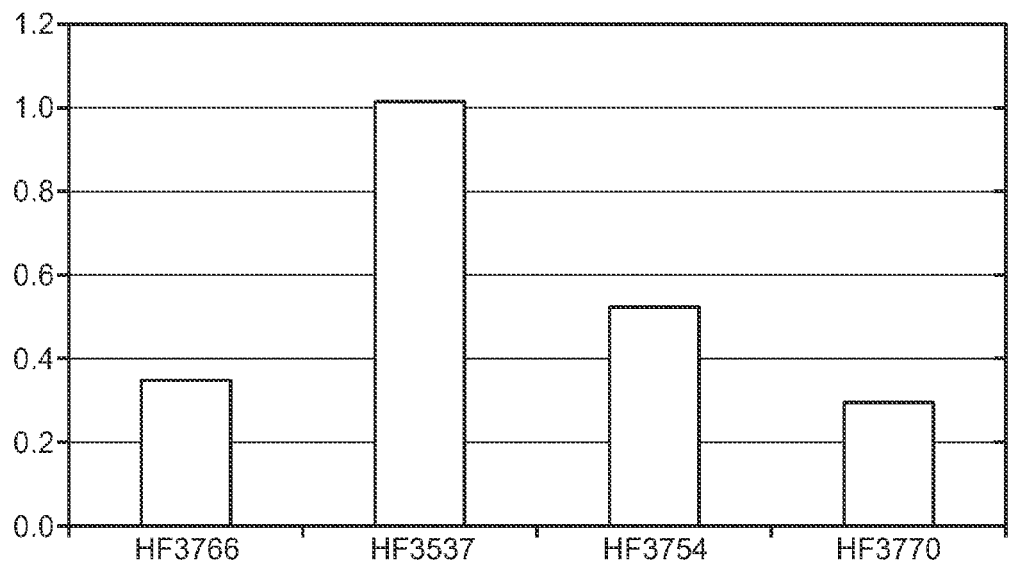
Figure 10C:
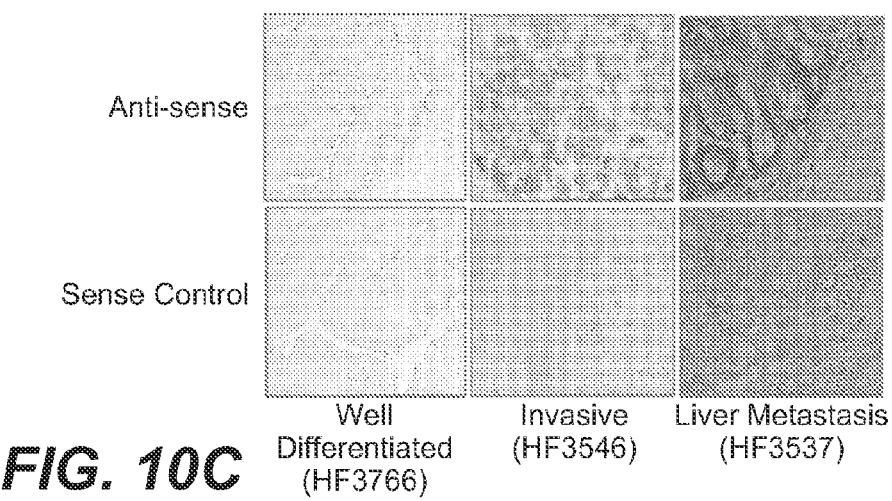

Laser capture microdissection (LCM) and transcript profiling were performed on fresh-frozen colon tumor sections. Sample collection was biased toward tumor cells near the tumor-stroma boundary. Five sets of normal colon epithelium were also isolated using LCM. β2 transcript was identified as overexpressed in tumor epithelium as compared to normal epithelium in a Student's T test comparing the sample populations (p value=0.0014, FIG. 1A; FIG. 10A). Detection of β2 transcript was validated using RT-PCR on RNA isolated from a subset of adjacent tumor sections (FIG. 10B). As an additional validation, non-isotopic in situ hybridization was performed on some adjacent tumor sections (FIG. 10C), confirming tumor cell expression.

Figure 1B:
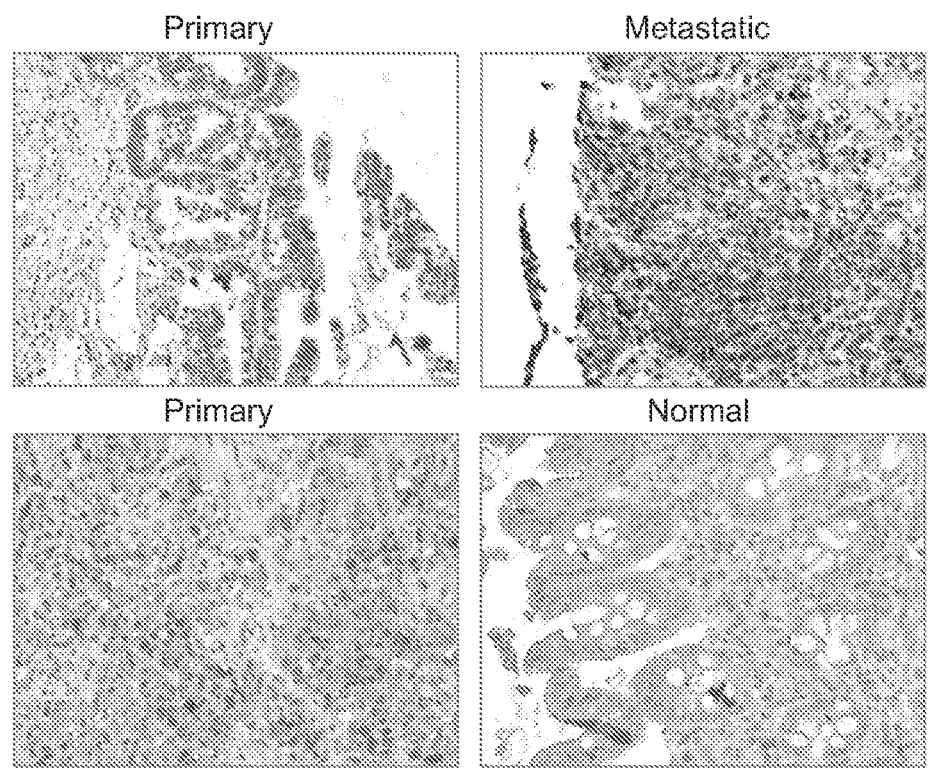

More extensive analysis of β2 expression in colon tumors by immunohistochemistry using an α-β2 monoclonal antibody and tissue microarrays revealed expression in tumor cells in grade III primary tumors and metastatic tumors (typically lymph node) from 22 of 41 patients (54%), and in 5 of 62 normal colon samples (8%). The tumor staining was heterogeneous and often punctate in nature, showing variation in intensity and distribution across the tumor epithelium (FIG. 1B). While the LCM analysis was biased toward the tumor-stroma boundary, this does not preclude expression elsewhere, and β2 was detected at the tumor edge as well as other regions of tumor epithelia not obviously bounded by stroma. The staining observed in the 5 β2-positive normal colons was weak to moderate, and present only in surrounding cells, not in the epithelial crypt cells. Overall, these data indicate that both the β2 transcript and protein are expressed in over 50% of colon tumors, contrasting with very limited expression in normal colon epithelium. Immunoblot analysis of protein isolated from tumor tissues indicated that β2 was also expressed in other tumor types, as well (FIG. 10E).

2. β2 Induces Morphological Transformation of Cells

Figure 2A:
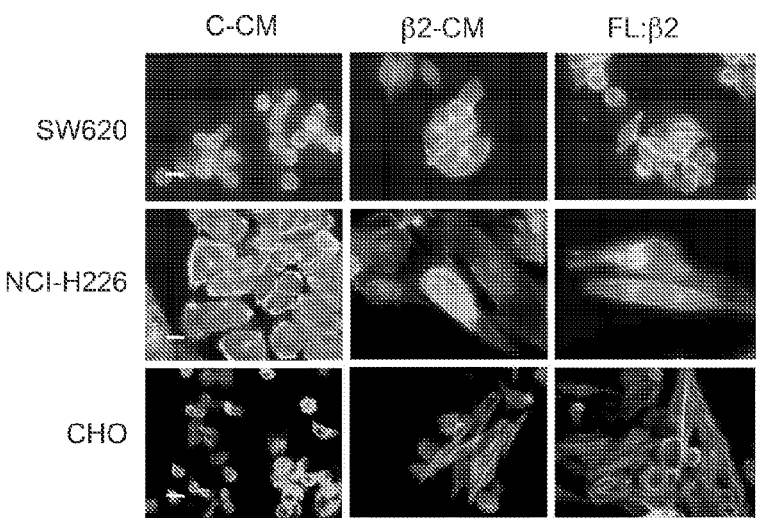
Figure 2B:
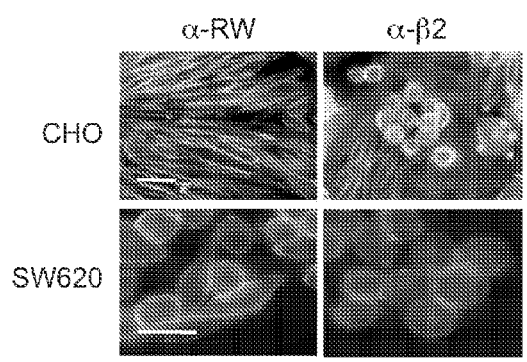
Figure 2C:
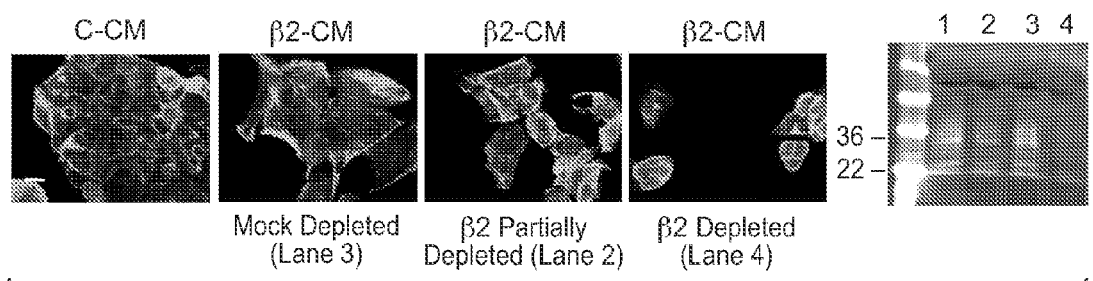
Figure 11A:
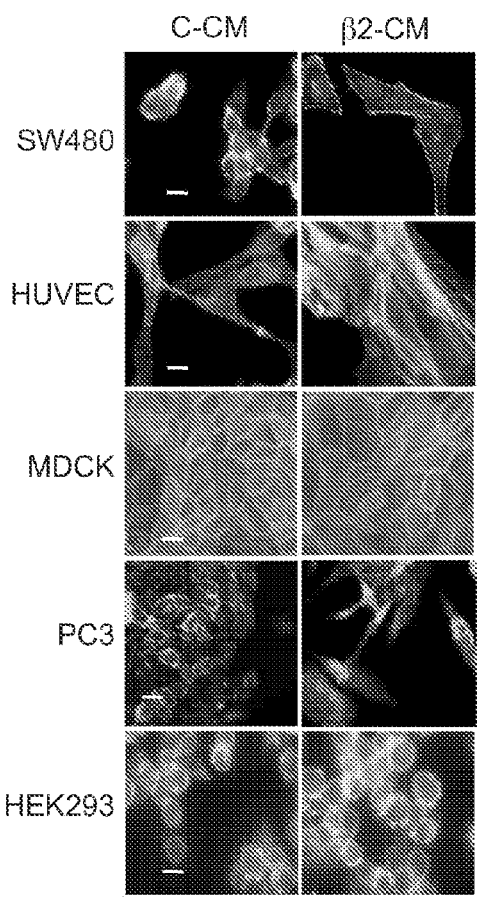

EMT is a transdifferentiation process in which epithelial cells acquire many attributes of more motile, invasive cells, including development of a more spindle-like, fibroblastic morphology. Expression of either β2 full-length protein or treatment of cells with conditioned media containing β2 extracellular domain (ECD) alone induced significant elongation and enlargement of cells as well as remodeling of the actin cytoskeleton (FIG. 2A). These changes were observed in numerous cell lines, including tumor cell lines such as NCI-H226 and SW620, as well as CHO cells (Chinese Hamster Ovary; FIG. 2A). Confirming that these changes resulted from expression of β2 protein, these effects could be blocked using a monoclonal antibody specific to the ECD of β2 (FIG. 2B): many newly divided cells were restored to a more normal, rounded appearance. Cells treated with an irrelevant control antibody (α-Ragweed) retained the β2-induced morphological change.

β2 contains a predicted mature ECD of ~129 amino acids, consisting largely of an Ig domain, along with a transmembrane region and a short (~35 amino acid) intracellular domain. We investigated whether the ECD alone could induce morphological change, by expressing a C-terminal his(8)- tagged ECD construct that was designed to be secreted from CHO cells. Conditioned media containing β2 ECD was capable of inducing phenotypic changes similar to those described above after 48-72 hours when placed on a variety of distinct cell types (naïve CHO cells, MDCK cells, HUVEC (endothelial), or tumor cell lines NCI-H226, SW620, SW480, and PC-3; FIG. 2A, FIG. 11A). To confirm that these effects were due to the presence of the β2 ECD, the β2 protein was depleted from the media, which was then added to naïve NCI-H226 cells. Changes in the actin cytoskeleton were assessed using rhodamine-phalloidin staining, and each sample was also analyzed by immunoblotting for β2 protein (FIG. 2C). Mock-depleted conditioned media contained β2 protein and induced complete phenotypic change. Conditioned media from which β2 was substantially depleted (>90%) yielded no detectable phenotypic changes, whereas conditioned media from which β2 was partially-depleted produced an intermediate phenotype, in which cells were enlarged and elongated but to a lesser degree than mock-treated cells. These data indicate that the phenotypic changes observed in β2 ECD conditioned media are dependent on the β2 ECD and reflect the level of β2 protein.

3. β2 Promotes Migration and Confers Protection Against Cell Death

Figure 3A:
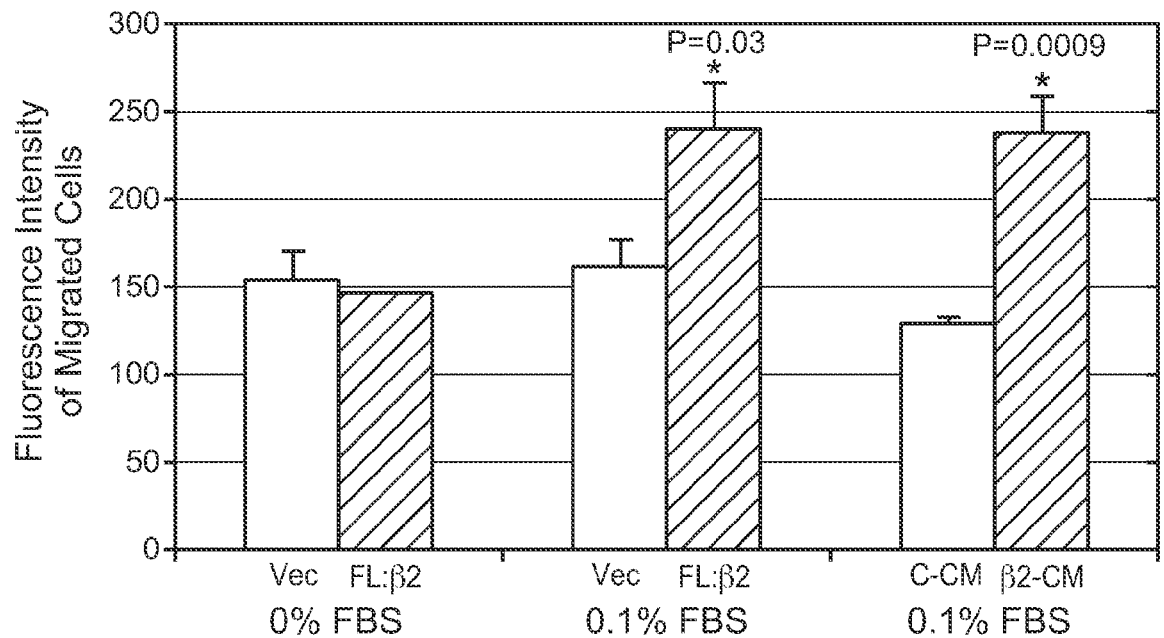
Figure 3B:
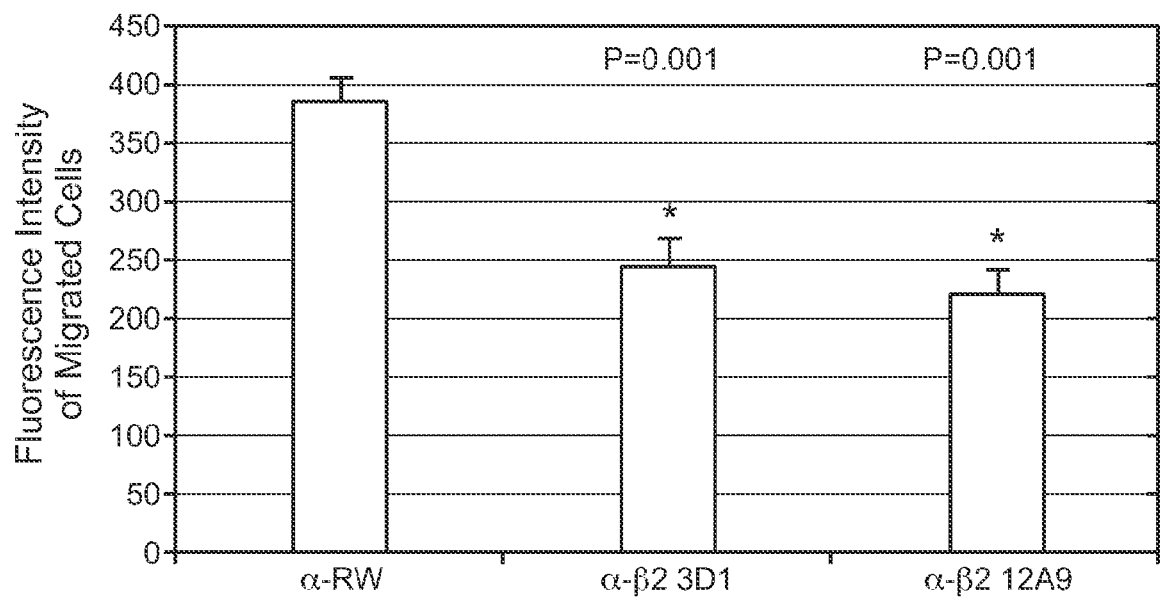

A physical property closely associated with cells undergoing EMT is increased motility. The effect of β2 on tumor cell migration was investigated by comparing the ability of β2 transfected and vector-transfected SW620 cells, or β2 ECD treated cells, to migrate across a transwell membrane to media containing fetal bovine serum (0.1%). Transfection efficiency was ~75%, with ~40% of cells in the SCN2B transfected pool displaying typical β2-induced phenotypic changes. After 18 hours, a significant increase in migration was observed for both β2 transfected cells and cells treated with β2 ECD in conditioned media (FIG. 3A; p=0.03 and 0.0009, respectively). Conversely, treating SW480 cells, which express β2 endogenously (see FIG. 5A), with 2 independent α-β2 antibodies resulted in a decrease in migration (FIG. 3B, p=0.001 for each antibody), further supporting a role for β2 in promoting cellular migration.

Figure 3C:
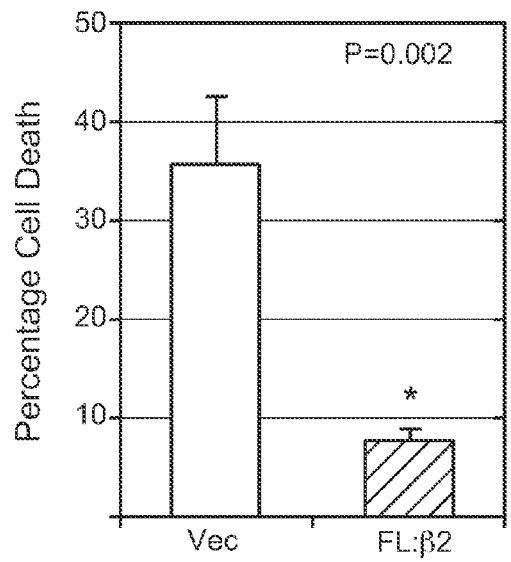
Figure 3E:
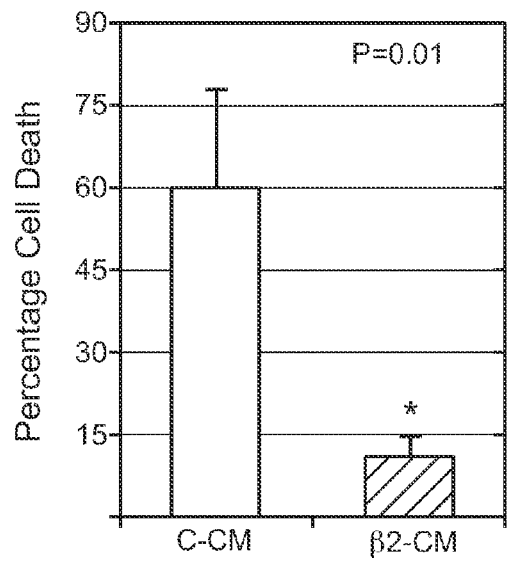
Figure 3D:
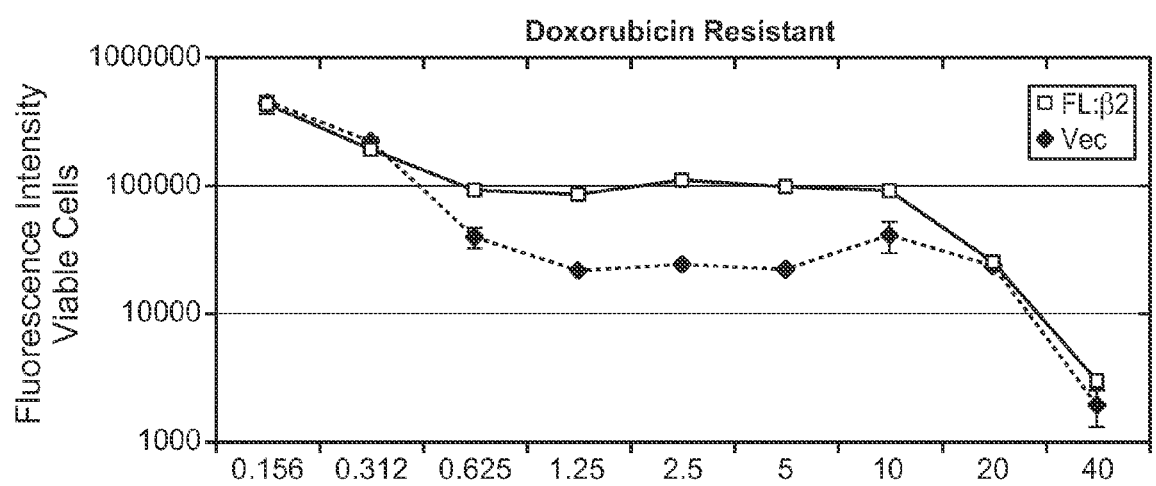

Another hallmark of EMT is increased resistance to cell death (Lee et al., 2006). The ability of β2 to influence this property was investigated in SW620 cells, which were subjected both to starvation and to treatment with chemotherapeutic drugs. β2-transfected or vector transfected control cells were subjected to starvation for a period of 2 weeks in media lacking serum and cell viability was compared to vector-transfected control cells using a trypan blue exclusion assay. β2 significantly increased cell viability, with less than 10% cell death as compared to 35% of vector-transfected control cells (p=0.002, FIG. 3C). β2 also promoted resistance to cell death upon exposure to the chemotherapeutic drug, doxorubicin (FIG. 3D). SW620 cells transfected with β2 exhibited significantly increased viability compared to vector-transfected control cells, over a 10-fold range of drug concentration, as determined by a quantitative cell viability assay (Cell Titer Glo, Promega, Madison, Wis.). Finally, we observed that expression of β2 by CHO cells increased their resistance to the chemotherapeutic drug, methotrexate, which was used as a selection for full-length β2 transfected CHO cells. To assess this independently, conditioned media from CHO cells expressing the β2 ECD only was added to naïve CHO cells and compared to control conditioned media-treated cells. In the presence of 200 nM methotrexate for 48 hours, 60% of control-treated cells died whereas the majority of β2-ECD treated cells remained viable (FIG. 3E, p=0.01), with only 10% cell death. These data indicate that the β2 ECD alone confers resistance to chemotherapeutic drugs.

4. β2 Induces Loss of E-Cadherin and Gain of Vimentin and this Process is Dependent on the EMT-Associated Transcription Factor Twist1

Figure 4A:
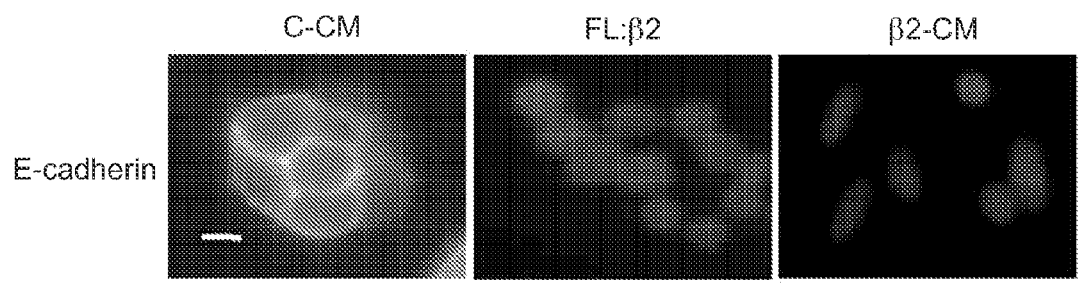
Figure 4B:
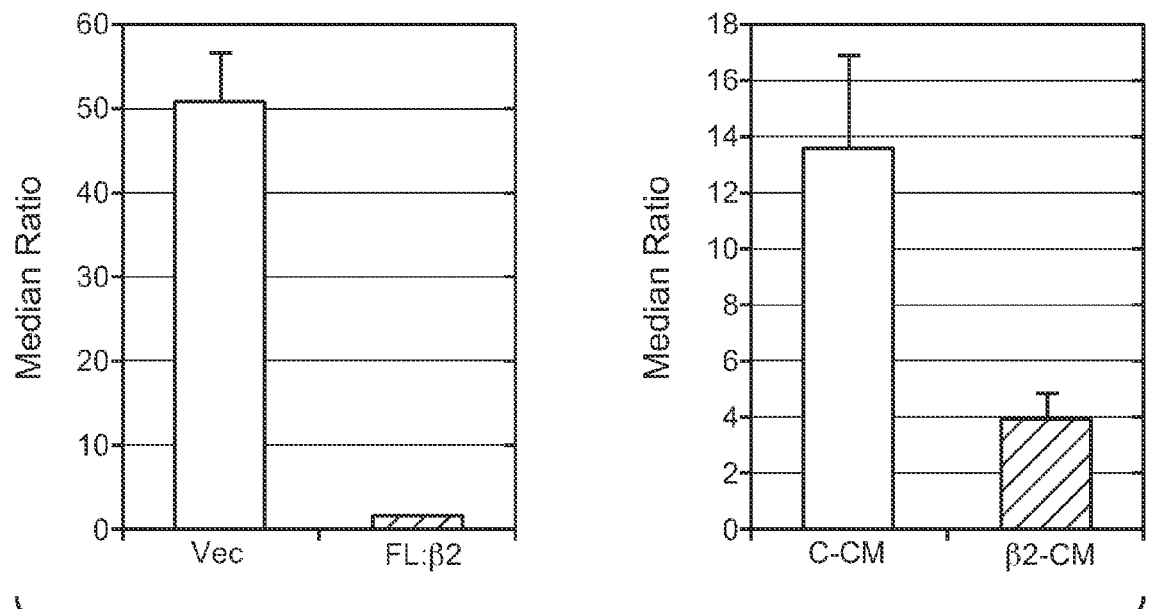
Figure 4C:
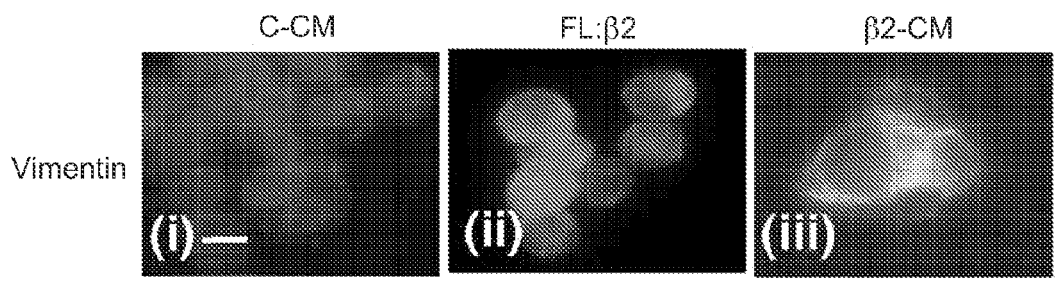

E-cadherin serves as one of the caretakers of epithelial phenotype and its loss is associated with both initiation and progression of tumors (Thiery and Sleeman, *Nat. Rev. Mol. Cell Biol.* 7:131-142, 2006). Loss of E-cadherin is also strongly associated with cells undergoing EMT. SW620 cells express E-cadherin (FIG. 4A) and transfection with β2 or treatment with β2 ECD in conditioned media for 48 hours greatly reduced E-cadherin protein levels, as evident by both immunofluoresence (FIG. 4A) and FACS analysis (FIG. 4B). Induced expression of the mesenchymal intermediate filament protein vimentin is another hallmark of epithelial cells undergoing EMT (Huber et al., *Curr. Opin. Cell Biol.* 17:548-558, 2005; Lee et al., *J. Cell Biol.* 172:973-981, 2006; Thiery and Sleeman, supra). Immunofluorescent staining of SW620 cells expressing either full length β2 or treated with β2 ECD in conditioned media, with α-vimentin antibodies, revealed a substantial increase in vimentin protein expression from otherwise undetectable levels (FIG. 4C).

Figure 12A:
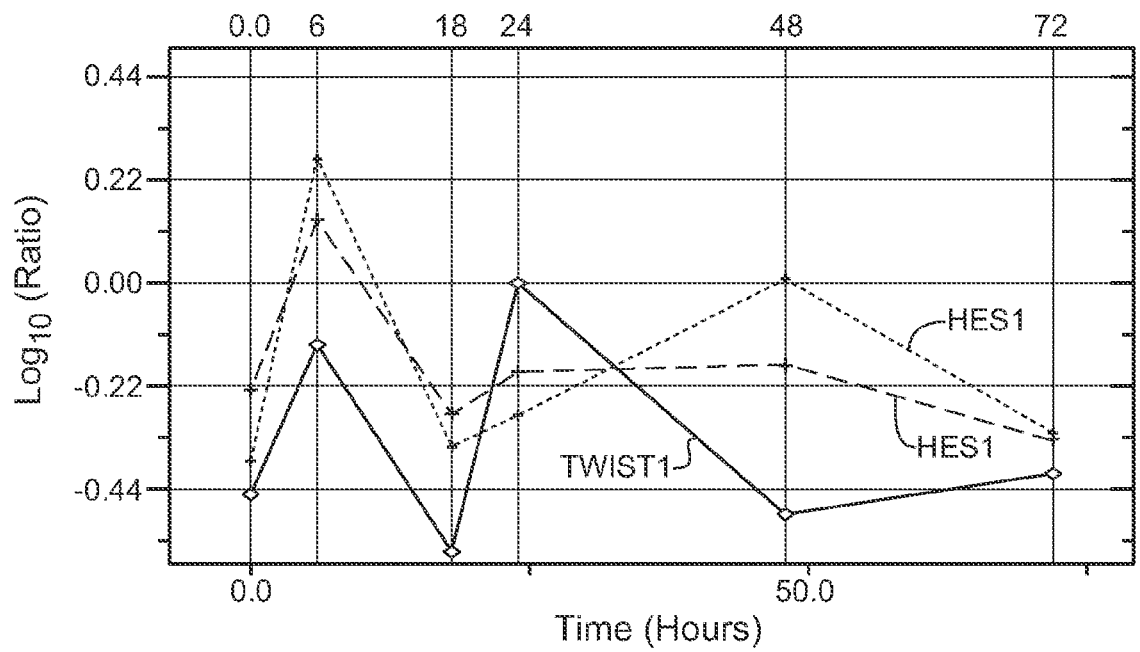
Figure 12B:
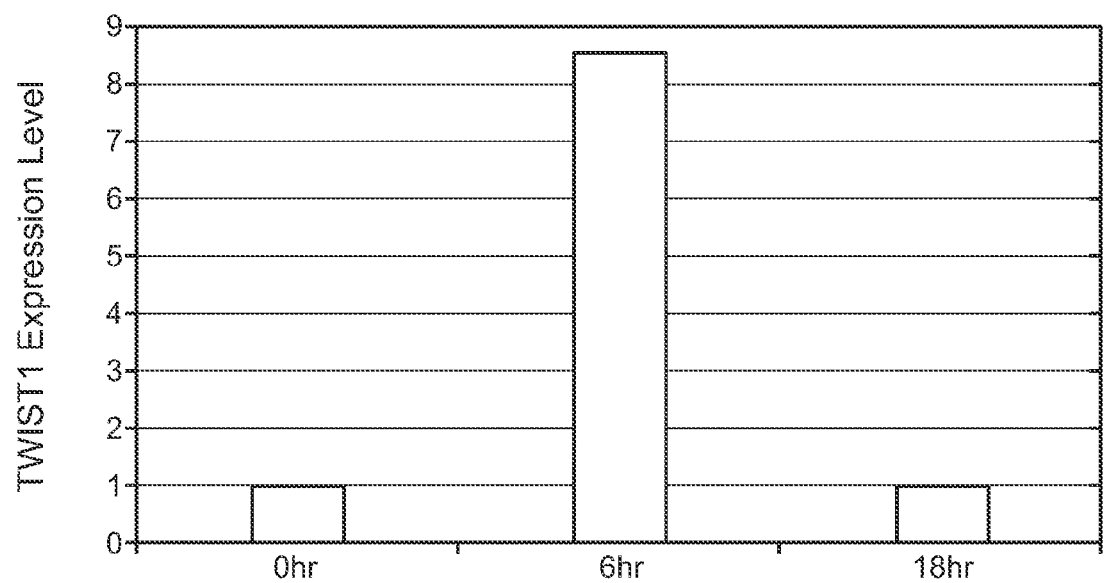

Given the ability of both full length β2 and β2 ECD to induce loss of E-cadherin and morphological transformation, the expression of transcription factors capable of mediating EMT was investigated. To facilitate detection of transcripts that might exhibit transitory expression or be subject to feedback regulation, SW620 cells were treated with β2 ECD in conditioned media and RNA was isolated at different timepoints. Microarray analysis revealed induction of Twist1 transcript 6 hours after treatment with β2 ECD with an oscillating pattern of expression at subsequent timepoints (FIG. 12A). RT-PCR analysis confirmed expression of Twist1 (FIG. 12B) and no significant or robust evidence of induction of transcripts for other characterized EMT transcription factors such as Snail and Slug/Snail2 (not shown). An oscillating pattern of regulation has been reported for transcription factors such as HES1, which mediate their own negative regulation (Hirata et al., *Science* 298:840-843, 2002) and our observations for Twist1 suggest the possibility that it is similarly regulated, or induced by a transcription factor that oscillates in this manner. As Twist1 is a transcriptional repressor that acts upon E-box sequences in the promoter of E-cadherin, and is capable of inducing EMT in epithelial cells (Batlle et al., *Nat. Cell Biol.* 2:84-89, 2000; Bolos et al., *J. Cell Sci.* 116:499-511, 2003; Cano et al., *Nat. Cell Biol.* 2:76-83, 2000; Conacci-Sorrell et al., *J. Cell Biol.* 163:847-857, 2003; Yang et al., *Cell* 117:927-939, 2004), these data suggest that induction of Twist1 expression after exposure to β2 may play a significant role in the morphological transformation observed.

Figure 4D:
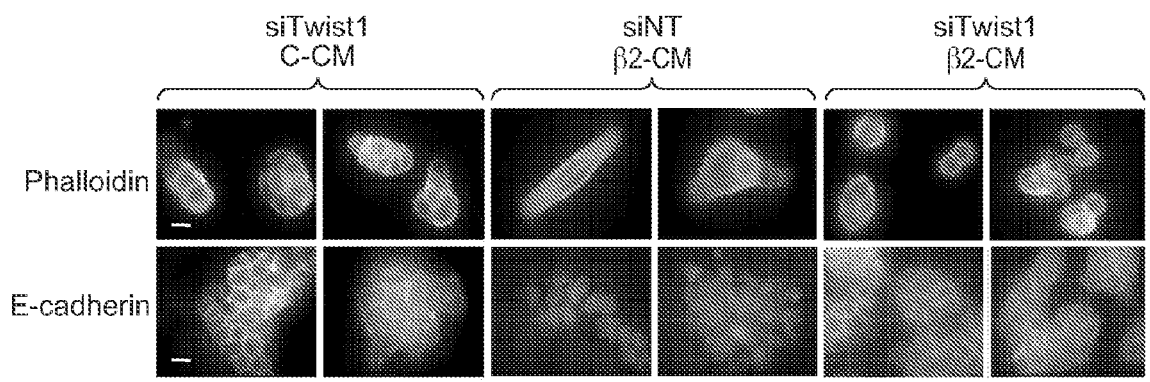
Figure 4E:
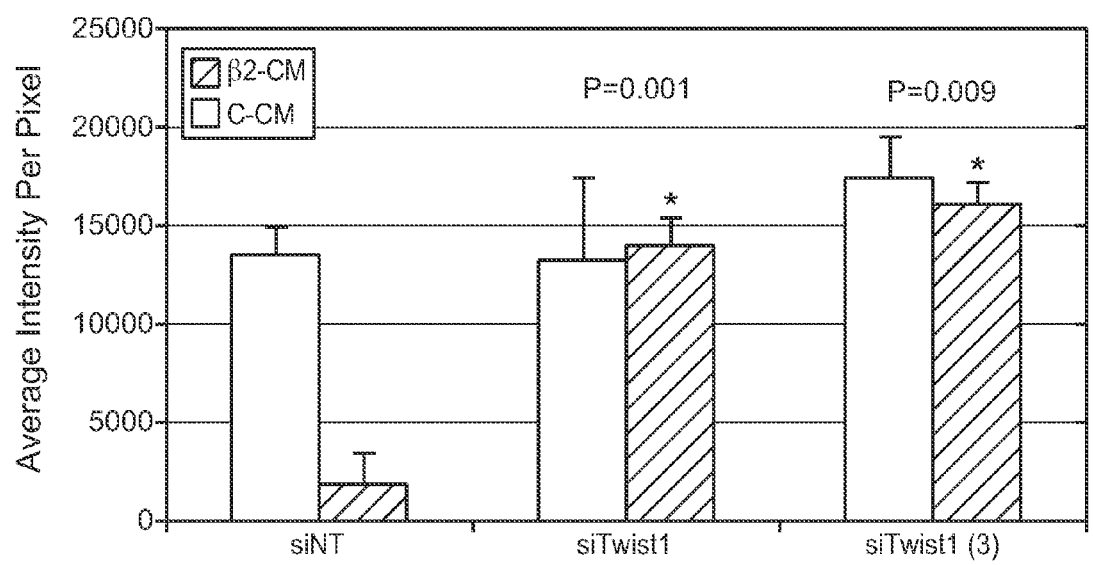

To further investigate the role of Twist1 in the EMT-like morphological transformation induced by β2, Twist1 was depleted from SW620 cells using siRNA knockdown. The cells were then treated with β2 ECD in conditioned media (FIG. 4D), and the actin cytoskeleton and E-cadherin staining assessed. In control cells treated with a non-targeting siRNA, treatment with β2 induced remodeling of the actin cytoskeleton and loss of E-cadherin, whereas control conditioned media had no effect on cells. However, in the presence of siRNAs specific to Twist1, β2 was no longer capable of inducing EMT: E-cadherin staining remained positive and cellular morphology was normal (FIG. 4D). Quantitative analysis of E-cadherin staining from multiple independent fields of cells revealed a statistically significant difference for β2 ECD-treated cells depleted for Twist1 as compared to control cells (FIG. 4E, p=0.001 and 0.009). These data indicate that the EMT induced by β2 in SW620 is dependent upon the presence of Twist1. Crosstalk and cooperation between EMT-associated transcription factors in development has been described (Aybar et al., *Development* 130:483-494, 2003; Ganguly et al., *Development* β2:3419-3429, 2005), and while their transcripts were not robustly detected in this study, it is possible that transcription factors such as Snail and Slug could also play a role in β2 induced EMT, either in these cells or in different cell types. Overall, given both the induction of Twist1 on treatment with β2 ECD and the dependence of the β2-induced morphological transformation on Twist1, a characterized EMT-inducing transcription factor, these results strongly support our phenotypic data findings that β2 does indeed induce EMT.

5. Knockdown of REST in Tumor Cells Results in EMT-Like Morphological Transformation that is Mediated by β2

Figures 8, 9:
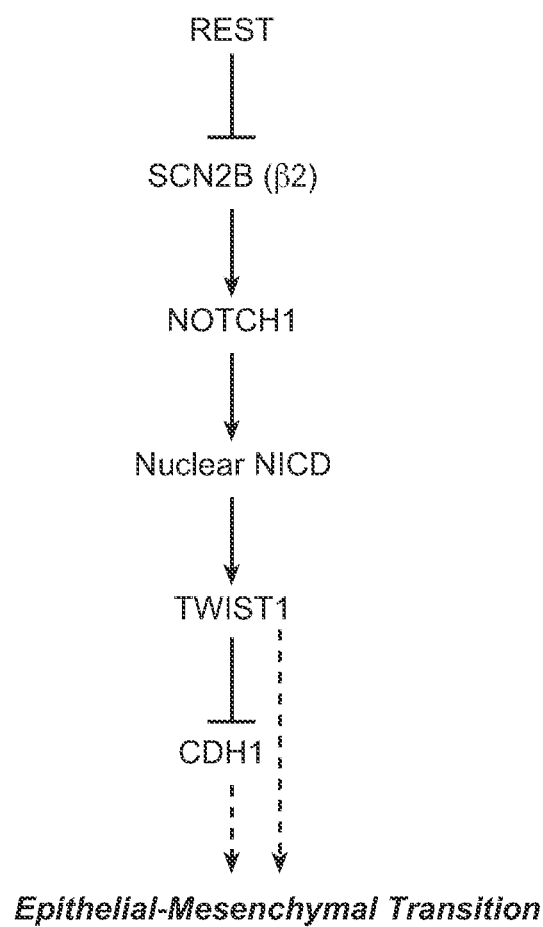

REST, a negative transcriptional regulator that restricts expression of neuronal genes in non-neural tissues, was more recently characterized as a tumor suppressor in colon and possibly other cancers (Westbrook et al., *Cell* 121:837-848, 2005). The type II voltage-dependent sodium channel and associated proteins are neuronally and developmentally expressed, and SCN2A was one of the first REST-regulated genes identified. Analysis of the SCN2B genomic region (encoding β2) revealed a cluster of 4 consensus REST binding sites in the first intron, suggesting that REST might regulate β2 expression. We further investigated a possible connection between the expression of β2 in tumor cells and REST deregulation using colon tumor cell lines. Staining of cell lines for REST and β2 proteins revealed reciprocal expression: colon cell lines SW480, SW1417, described as REST negative (Westbrook et al., supra), along with SW1116, were β2 positive whereas β2 was not detected in REST positive line SW620 (FIG. 9, FIG. 5A). DLD-1 expresses a mutant REST protein lacking a repressor domain (Westbrook et al., supra) and stained positive for β2 (FIG. 9). These data are consistent with β2 being transcriptionally repressed by REST, either directly or indirectly. Analysis of REST and β2 protein expression in colon tumors by immunohistochemistry revealed that this relationship persists: we found a reciprocal pattern of staining for REST and 13 in the grade III adenocarcinoma and metastatic colon tumor samples described earlier. Punctate REST staining was observed in tumors from 18 of 41 patients (44%; FIG. 5A) and in only one tumor was there overlap in staining between REST and β2 (for which expression was detected in 22 of 41 cases). REST staining was detected in 40 of 62 normal colon samples (65%), none of which were β2 positive. These results indicate that the anti-correlation in expression is not just a cell line phenomenon but is also true for tumor tissues, and supports the hypothesis that loss of REST in human tumor cells could contribute to the expression of β2.

Figure 5E:
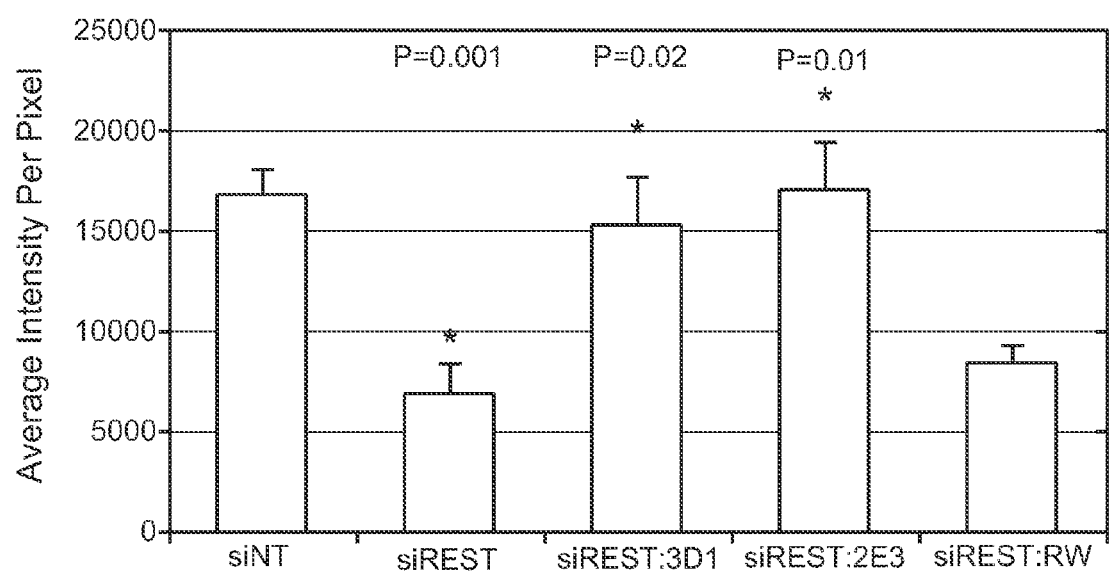
Figure 13A:
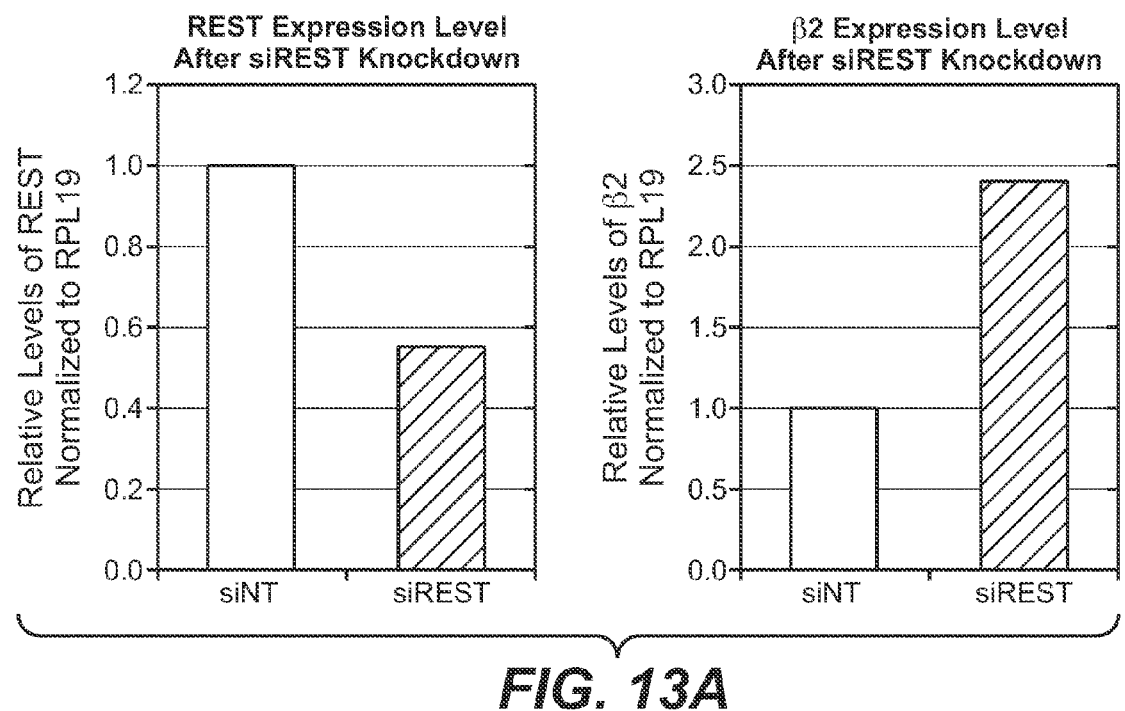
Figure 13B:
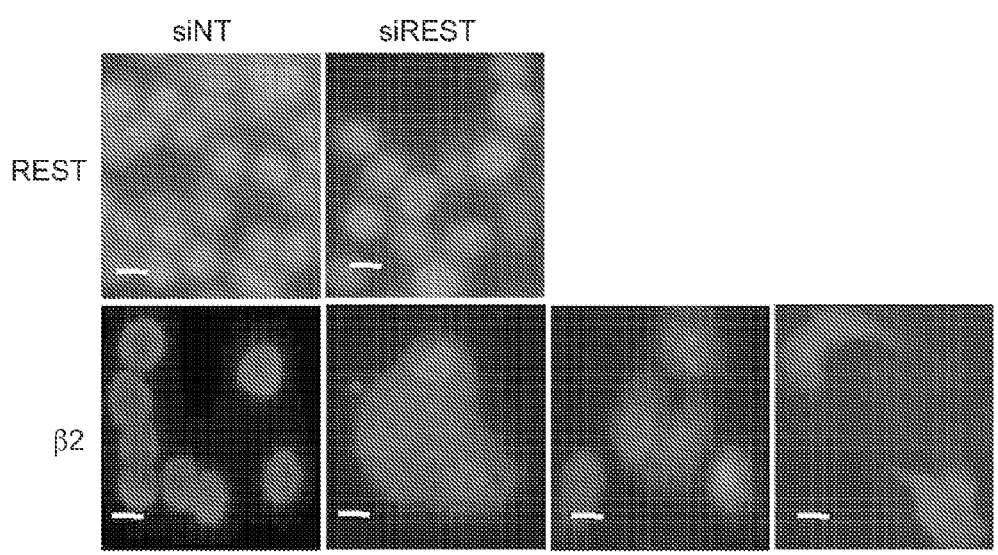
Figure 13C:
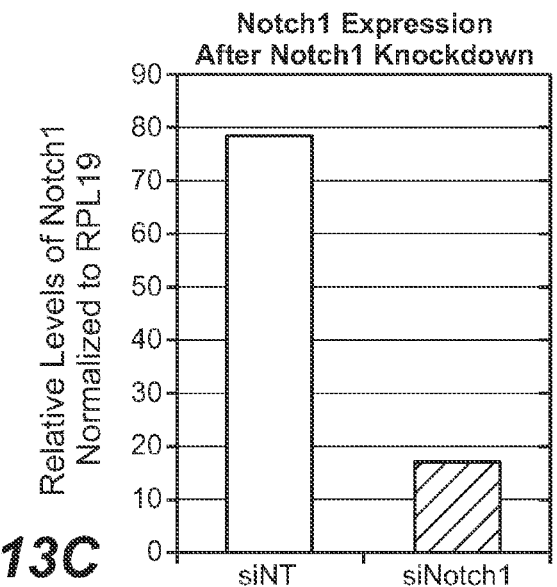

We further investigated the possibility of a biologically-relevant functional relationship between the REST tumor suppressor and β2. To determine whether loss of REST might result in expression of β2 and induction of EMT in a tumor cell context, REST was depleted in SW620 using RNAi. SW620 shows a pattern of REST and β2 staining opposite to that of SW480 (FIG. 5A), but is derived from tumors from the same individual. Five days after transfection with REST-specific siRNA, immunoblot analysis confirmed a substantial decrease in REST and a significant increase in β2 protein as compared to cells transfected with a non-targeting control siRNA (FIG. 5B, C; FIG. 13A, B). Changes in cell morphology consistent with the J32-induced EMT as visualized using rhodamine-phalloidin staining of the actin cytoskeleton, substantial reduction of E-cadherin, and induction of vimentin were also apparent in the REST knockdown cells (FIG. 5D). Quantitative analysis of E-cadherin staining from multiple independent fields of cells revealed a statistically significant decrease for cells transfected with REST-specific siRNA as compared to cells transfected with a non-targeting control siRNA (FIG. 5E; p=0.001). Overall, these data indicate that, in a tumor-cell context, one consequence of loss of REST is expression of β2 and induction of morphological changes consistent with EMT.

Having demonstrated that knockdown of REST induced changes in morphology and marker expression consistent with EMT, we used functionally-blocking β2 monoclonal antibodies to determine if the induction of EMT resulting from loss of REST is primarily mediated by expression of β2. REST was depleted in SW620 cells using siRNA, and cells were allowed to grow for 4 days in the presence of antibodies directed against either β2 or an irrelevant target (Ragweed). Cells were then stained with phalloidin to visualize the actin cytosekeleton or with an α-E-cadherin or α-vimentin antibody. α-Ragweed antibody treated cells underwent morphological change and loss of E-cadherin typical of the β2-induced EMT and REST knockdown. However, REST-depleted cells treated with β2-specific blocking monoclonal antibodies 3D1 and 2E3 had normal morphology, strong E-cadherin expression, and little or no expression of vimentin, similar to that observed with the non-targeting siRNA control (FIG. 5D). Quantitative analysis of E-cadherin staining from multiple independent fields of cells revealed a statistically significant increase in E-cadherin levels in siREST cells treated with each of the independent β2 functionally-blocking antibodies 3D1 and 2E3 compared to the untreated siREST or α-Ragweed treated siREST cells (FIG. 5E, p=0.02 and 0.01, respectively). These results are consistent with the EMT-lik morphological transformation induced by loss of REST being mediated by β2, and indeed requiring extracellular expression of β2.

6. Induction of EMT-Like Morphological Transformation by β2 is Dependent Upon Notch1

Figure 6A:
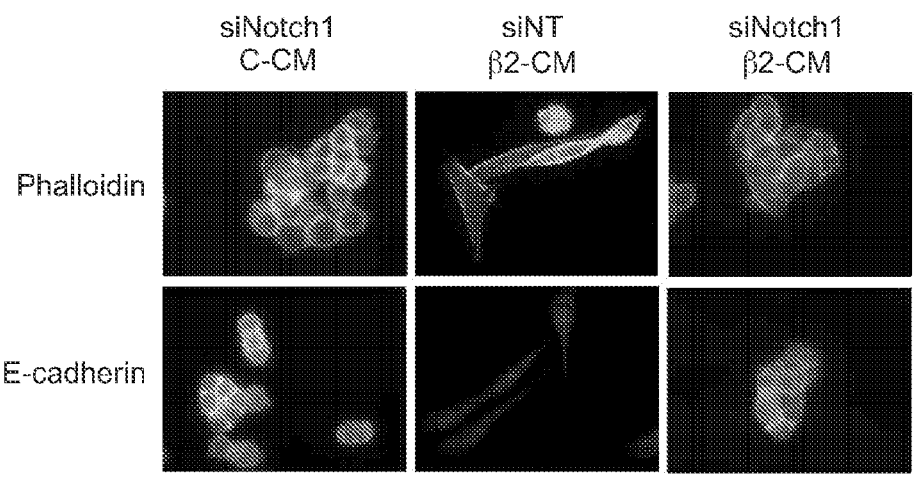
Figure 11B:
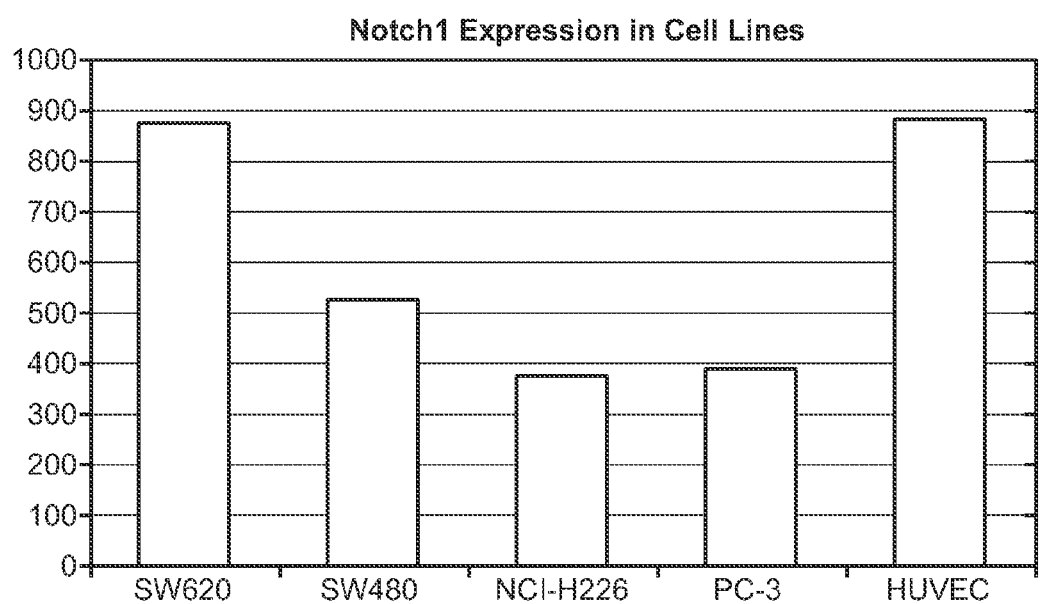
Figure 11C:
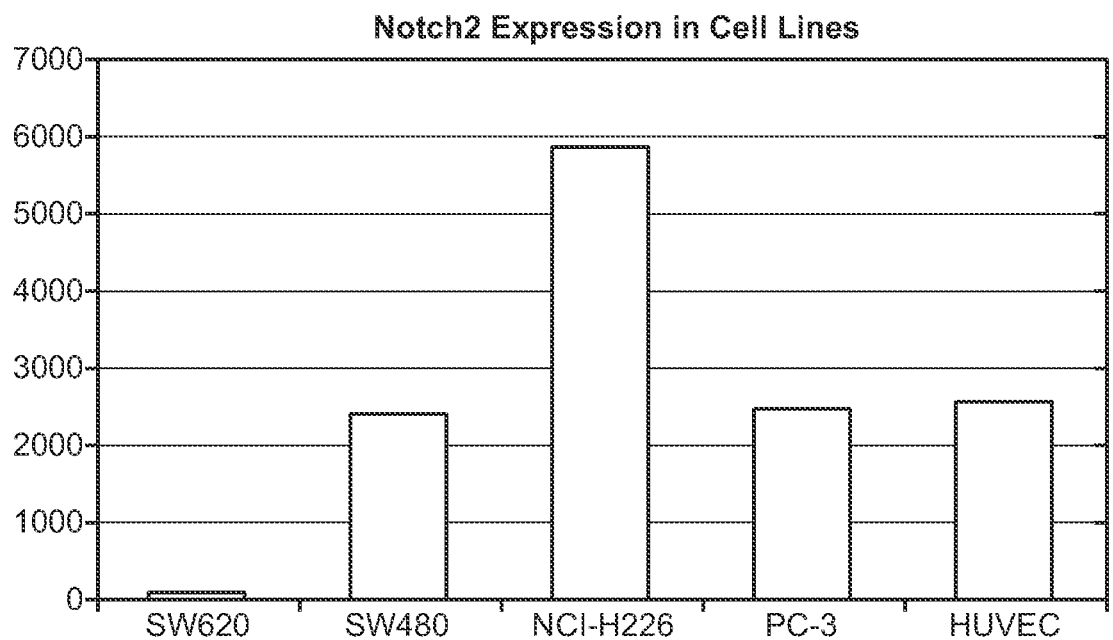

Notch signaling is an ancient and conserved system that regulates cell fate in development and in adult self-renewing cells (Artavanis-Tsakonas et al., *Science* 284:770-776, 1999). HES1 is a characterized target of Notch pathway signaling (Jarriault et al., *Nature* 377:355-358, 1995) which undergoes an oscillating cycle of transcript expression, due to self-mediated negative regulation (Hirata et al., *Science* 298:840-843, 2002). Oscillating HES1 expression at early timepoints (6-24 hrs) in transcript expression data derived from SW620 cells treated with β2 ECD (FIG. 12A) suggested a role for Notch signaling in the EMT induced by β2. Transcript analysis indicated that Notch1 was the only Notch family receptor expressed at significant levels on SW620 cells (FIGS. 11B, C, D). To determine whether Notch1 was required for the β2 ECD to induce EMT in SW620 cells, cells were transfected with siRNAs specific for Notch1 or a non-targeting control siRNA, treated with β2 ECD in conditioned media, and analyzed for loss of E-cadherin, as a primary marker of Twist1 activity and EMT. Cells transfected with a non-targeting siRNA and treated within ECD demonstrated loss of E-cadherin staining as compared to control-media treated cells, but depletion of Notch1 blocked this morphologic transformation and resulted in cells with a normal actin cytoskeleton which were positive for E-cadherin (FIG. 6A, C). These data indicate that Notch1 is necessary for the induction of the EMT-like morphological transformation by β2.

Figure 6B:
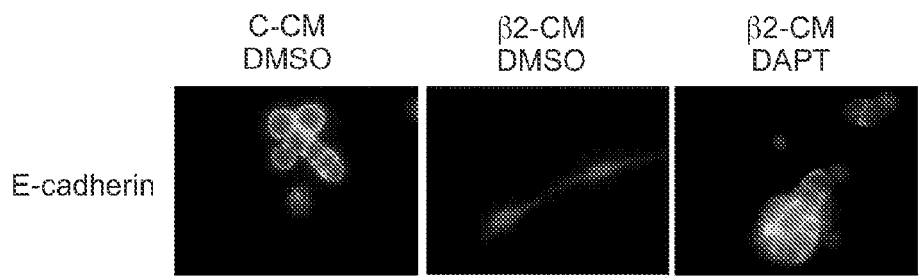
Figure 6C:
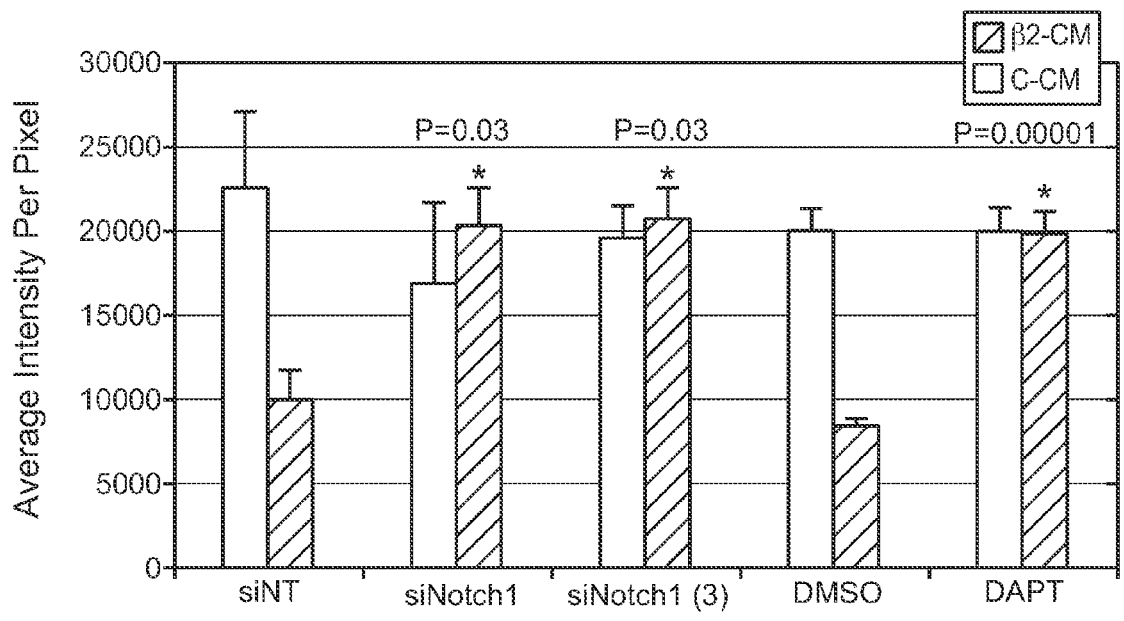

Activation of Notch signaling requires cleavage of the receptor by both an ADAM protease and gamma-secretase to release the Notch intracellular domain (NICD). We thus asked whether a gamma-secretase inhibitor, which prevents Notch signaling (De Strooper et al., Nature 398:518-522, 1999) would also inhibit β2-induced EMT. SW620 cells were mixed with DMSO (vehicle control) or the specific gamma-secretase inhibitor DAPT (N—[N-(3,5-difluorophenylacetyl-L-alanine)]-S-phenylglycine t-butylester) at 500 nM in DMSO, treated with β2 ECD in conditioned media, and analyzed for loss of E-cadherin. Unlike full-length β2, the β2 ECD construct does not contain the characterized gamma-secretase cleavage site (Kim et al., J. Biol. Chem. 280:23251-23261, 2005) and thus is not a target for inhibition of processing by DAPT. Cells treated with β2 ECD in the presence of DMSO showed the typical loss of E-cadherin, as compared to cells treated with control conditioned media. However, cells treated with β2 ECD in the presence of DAPT remained E-cadherin positive, suggesting that Notch1 signaling is required for the induction of EMT by β2 (FIG. 6B, C). Quantitative analysis of E-cadherin in both siRNA knockdown and gamma-secretase inhibition experiments confirmed a statistically significant difference in E-cadherin levels in cells treated with β2 ECD in which Notch1 was depleted or Notch1 signaling was inhibited (FIG. 6C).

Figure 11D:
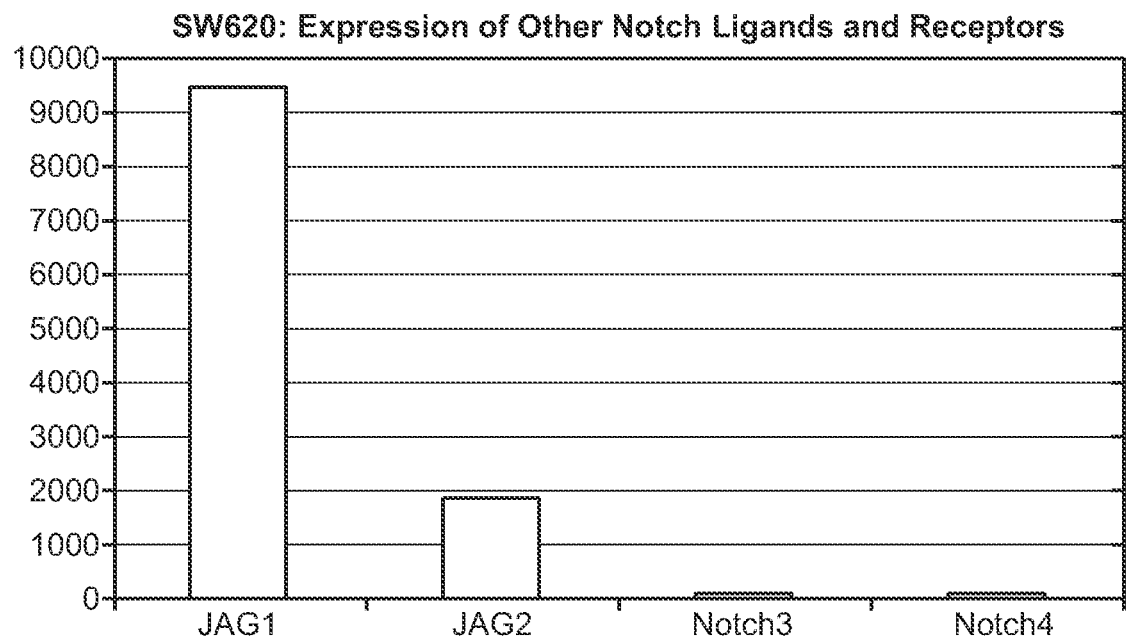

SW620 cells express the Notch ligands Jagged1 and Jagged2 (FIG. 11D), yet are not undergoing EMT. Given the apparent role of Notch signaling in the EMT induced by β2, we investigated whether Notch ligands from the Jagged or Delta-like families could induce EMT. Cells were stimulated by exogenous addition of the ligands Jagged1 or DLL1 in various formats, including in trans by co-culture with ligand-expressing cells or using plate-bound ligand, but no evidence of EMT was observed under any of the conditions used (data not shown). As a positive control, co-culture of Notch ligand-expressing cells with 3T3 cells transfected with Notch1 produced evidence of Notch pathway signaling as determined by a luciferase reporter assay from a CSL-binding promoter construct (data not shown). However, treatment of SW620 in similar co-culture assays with Jagged1-expressing or DLL1-expressing cells failed to induce either EMT-like morphological change or significant activity by the reporter construct (data not shown). It is possible that the reporter construct was insufficiently sensitive to detect endogenous Notch signaling in SW620, but this consideration notwithstanding, there was no evidence of induction of EMT or related morphological change by either Jagged1 or DLL1, suggesting that expression and presentation of these characterized Notch ligands in trans was not sufficient to induce EMT in these cells.

7. β2 Binds Notch1 and Induces Nuclear Localization of the Notch Intracellular Domain (NICD)

Treatment of cells with the β2 ECD induced phenotypic changes in cells that do not endogenously express β2 (eg. SW620), indicating that the receptor through which β2 acts is not β2 itself. Having established that the EMT induced by β2 was dependent upon Notch1 and Notch pathway signaling, and having observed induction of HES1 transcript at a 6 hour timepoint (FIG. 12A), well prior to the appearance of phenotypic changes (24-72 hours), we investigated the possibility that β2 might be a ligand or binding partner of Notch 1. β2, an Ig domain protein, does not share the sequence properties of classical Notch ligands such as Jagged-1 or 2 and DLL1. However, two other Ig domain proteins, contactin/F3 and NB3, have been described as novel Notch ligands that contribute to the determination of cell fate in neuronal precursors (Cui et al., J. Biol. Chem. 279:25858-25865, 2004; Hu et al., Cell 115:163-175, 2003). In considering Notch1 as a candidate receptor for β2, Notch1 (or possibly Notch2) expression would be expected in cells that undergo morphological change in response to the β2 ECD. Transcript analysis revealed that β2-responsive tumor cell lines expressed Notch1 (and frequently, also Notch2; examples in FIGS. 11B, C). Endothelial HUVEC cells expressed Notch1 and also responded to β2, whereas HEK293 cells, which showed no phenotypic change in response to β2 (FIG. 11A), do not express Notch1 (Hicks et al., Nat. Cell Biol. 2:515-520, 2000; Ray et al., J. Biol. Chem. 274:36801-36807, 1999). These observations are consistent with Notch1 being an effector or receptor for β2.

Figure 7A:
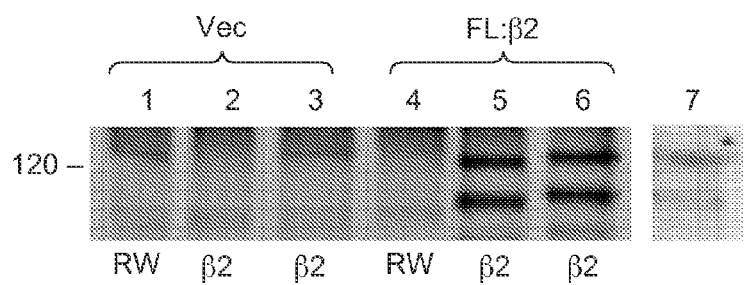

To determine whether Notch1 and β2 can physically associate, we performed a co-immunoprecipitation and immunoblot analysis of full-length β2-transfected SW620 cells, using α-β2 monoclonal antibodies or an irrelevant control antibody (α-Ragweed) in the immunoprecipitation. Immunoblotting with a Notch1-specific monoclonal antibody revealed that α-β2 antibodies co-precipitated endogenous Notch1 from β2-transfected cell lysates. This co-precipitation appeared specific as we did not observe Notch1 precipitation using the control antibody or using the α-β2 antibody with control lysates from cells not expressing β2 (FIG. 7A).

Figure 7B:
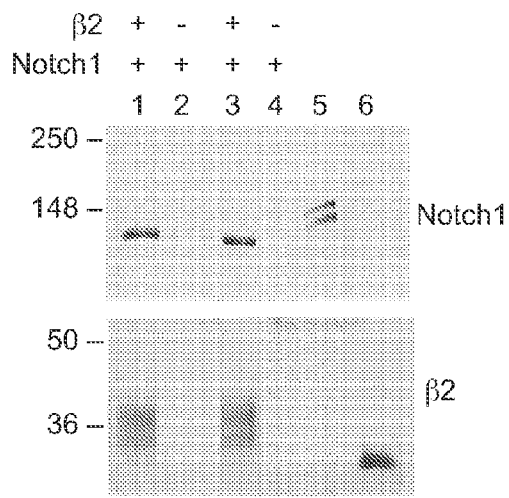

The possibility that β2 can bind Notch1 directly was investigated using C-terminal histidine-tagged β2 ECD and a purified Notch1 ECD region containing the majority of the EGF repeat region (repeats 6-36) with a C-terminal FLAG tag. Notch1 ECD (0.33 μg/ml) was incubated with β2 ECD in conditioned media (β2 estimated at 0.4 μg/ml) and β2 protein was then collected using Ni-NTA beads. Alternatively, β2 was enriched from conditioned media using Ni-NTA beads and subsequently incubated with tagged Notch1 ECD (at 3.3 μg/ml) in PBS. Both approaches yielded recovery of tagged Notch1 by β2, as compared to control conditioned media containing an irrelevant histidine-tagged protein (FIG. 7B). Notably, the β2-Notch1 binding occurred even at low concentrations of both proteins (approximately 1 nM Notch1 ECD and 20 nM β2 ECD, FIG. 7B lane 1) and in the presence of serum, other CHO-produced proteins and degradative enzymes present in the conditioned media. Purified Notch1 ECD migrated as a doublet band, possibly due to glycosylation or other modification (FIG. 7B). However, binding to β2 resulted in a single well-defined band for the tagged Notch1 ECD, suggesting specificity, or possible modification, associated with binding. Overall, these results support a role for β2 as a binding partner of Notch1. Similar to other Notch ligands, we anticipate that β2 would also bind close homolog Notch2, which is highly expressed on some β2 responsive cell lines.

Figure 7C:
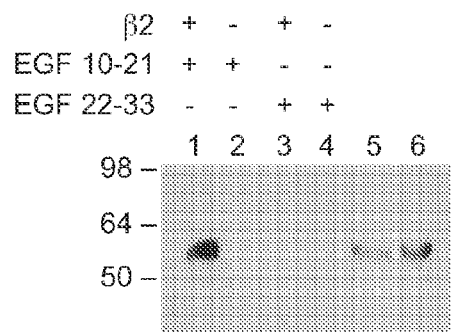

To further characterize the binding of β2 and Notch1, conditioned media containing tagged β2 ECD were incubated as described above with purified fragments of the Notch1 ECD, containing either EGF repeats 10-21 or 22-33. (Jagged-1 binds EGF repeats 11-13 of Notch1, and Drosophila Delta and Serrate bind EGF repeats 11-12 of Notch.) Each of these Notch1 ECD fragments contained a C-terminal FLAG tag to allow detection on an immunoblot with α-FLAG antibody. The β2 ECD specifically bound the Notch1 ECD fragment containing EGF repeats 10-21, with no detectable binding of the ECD fragment containing EGF repeats 22-33 (FIG. 7C). These data indicate that the binding of β2 and Notch1 is specific, rather than a non-specific association through EGF repeat structures.

Figure 7D:
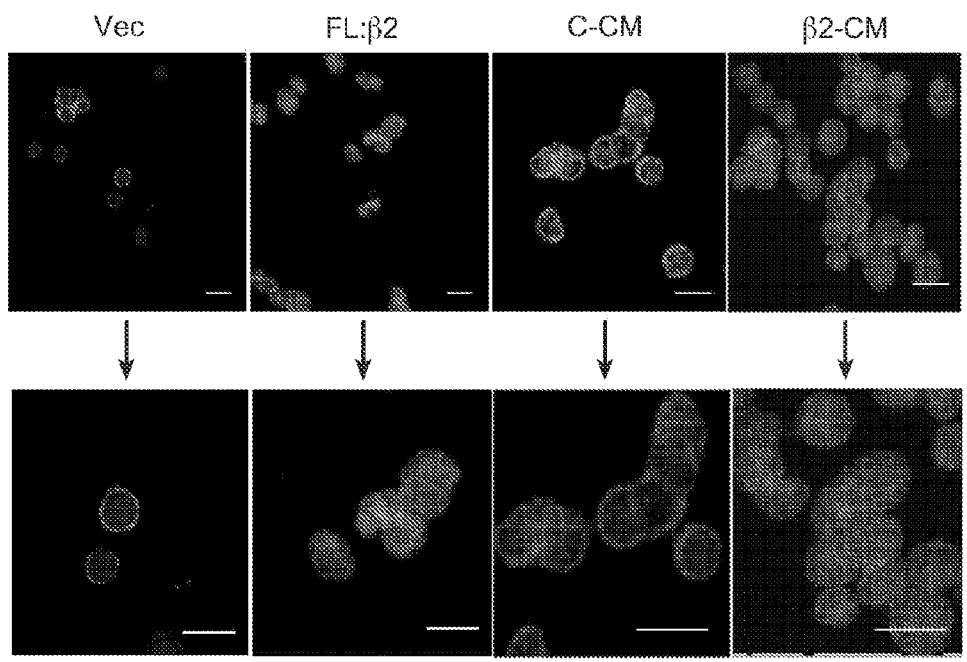

Activation of Notch1 by ligands results in cleavage to release the NICD, which translocates to the nucleus, and in concert with other proteins, directly regulates Notch target gene transcription. We analyzed whether nuclear NICD could be detected in cells in response to β2. As the NICD has been historically difficult to detect, we grew cells in the presence of a proteasome inhibitor (100 um Lactacystin) to assist in protein stabilization, and used high-resolution confocal microscopy for imaging. Nuclear NICD was detected in the majority of cells transfected with β2 compared to the vector-transfected control, in which, with the exception of 1 cell, cytoplasmic or membraneous staining only was observed (FIG. 7D). Similarly, nuclear NICD was detected in SW620 cells 6 hours after treatment with β2 ECD in conditioned media (FIG. 7D), consistent with the elevated HES1 transcript observed in these cells at 6 hours. These data indicate that β2 induces activation of the Notch signaling pathway.

Taken together, our data indicate that, beyond a role as an accessory protein or adhesion molecule, β2 can induce morphological transformation consistent with EMT. Expression of this neuronal protein in tumors can result from the loss of REST, a transcriptional repressor of neuronal gene expression in non-neuronal tissues. Furthermore, the morphological transformation induced by β2 depends on Notch, an evolutionarily conserved master regulator of development, differentiation and cell fate (Artavanis-Tsakonas et al., *Science* 284:770-776, 1999). In linking loss of REST and the Notch pathway signaling via a novel Notch binding partner β2, we describe a role for all three in tumor progression and metastasis.

8. Antibody Cross-Blocking Experiments Suggest Three Distinct Epitopes

Figure 14:
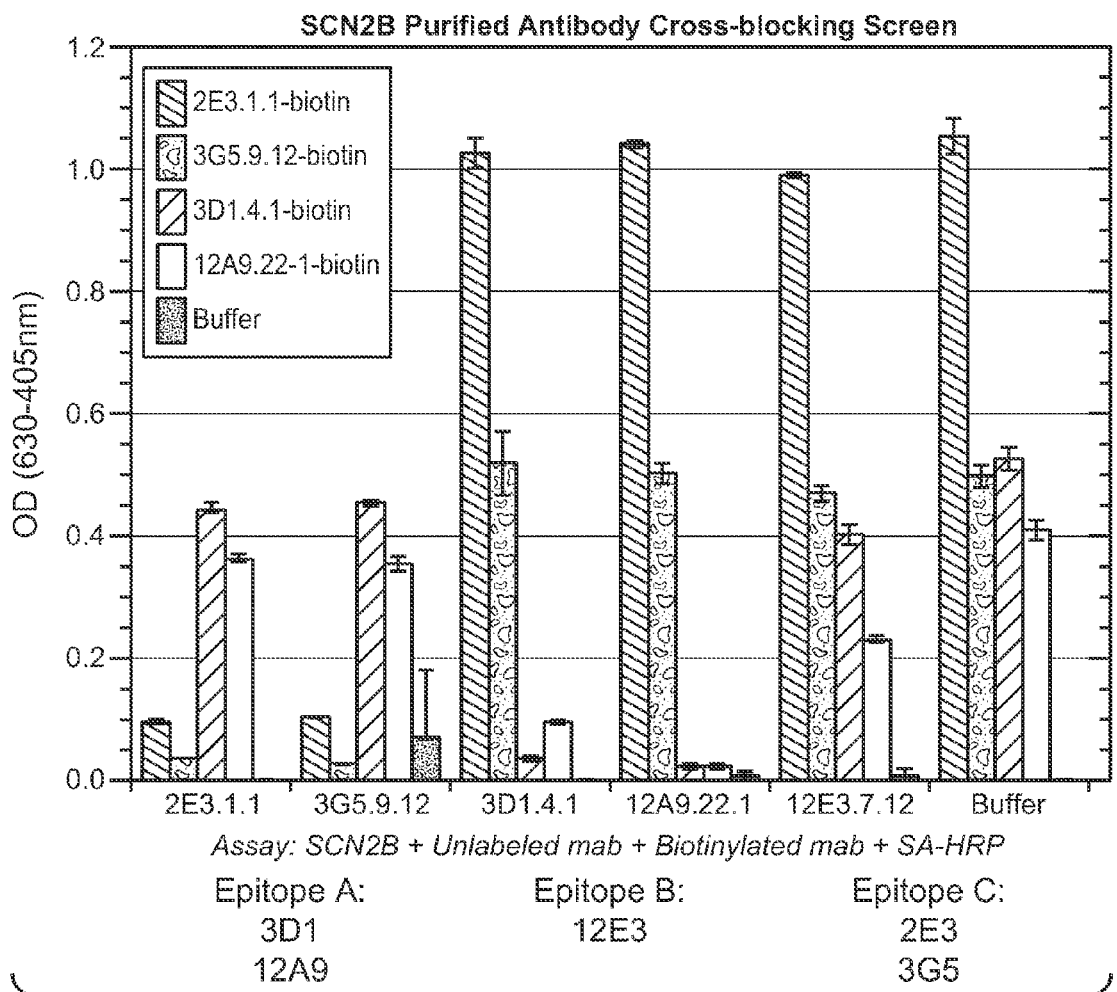

Antibody cross-blocking experiments were performed to determine whether the following α-β2 monoclonal antibodies bind to the same or different epitopes: 3D1, 12A9, 12E3, 2E3, and 3G5. In those experiments, the binding of biotinylated antibody to β2 antigen was assessed in the presence of an unlabeled "competitor" antibody, as depicted in FIG. 14. The results indicated that antibodies 3D1 and 12A9 bound to a first epitope ("Epitope A"); antibody 12E3 bound to a second epitope ("Epitope B"); and antibodies 2E3 and 3G5 bound to a third epitope ("Epitope C").

9. ATCC Deposits

The following hybridoma cell lines have been deposited with the American Type Culture Collection, 10801 University Blvd., Manassas, Va. 20110-2209 USA (ATCC):

| Hybridoma/Antibody Designation | ATCC No. | Deposit Date |
| --- | --- | --- |
| 12A9.22.1 (12A9) | PTA-8404 | May 2, 2007 |
| 3D1.4.1 (3D1) | PTA-8405 | May 2, 2007 |
| 2E3.1.1 (2E3) | PTA-8406 | May 2, 2007 |

These deposits were made under the provisions of the Budapest Treaty on the International Recognition of the Deposit of Microorganisms for the Purpose of Patent Procedure and the Regulations thereunder (Budapest Treaty). This assures the maintenance of a viable culture of the deposit for 30 years from the date of deposit and for at least five (5) years after the most recent request for furnishing of a sample of the deposit. The deposit will be made available by the ATCC under the terms of the Budapest Treaty, and subject to an agreement between Genentech, Inc., and the ATCC, which assures that all restrictions imposed by the depositor on the availability to the public of the deposited material will be irrevocably removed upon the granting of the pertinent U.S. patent; assures permanent and unrestricted availability of the progeny of the culture of the deposit to the public upon issuance of the pertinent U.S. patent or upon laying open to the public of any U.S. or foreign patent application, whichever comes first; and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited cell line is not to be construed as a license to practice the invention in contravention of the rights granted under the authority of any government in accordance with its patent laws.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. A monoclonal antibody that binds to β2 and blocks binding of β2 to Notch1.

2. The monoclonal antibody of claim 1, wherein the monoclonal antibody:
   a. is produced by a hybridoma selected from ATCC Accession Number PTA-8404, PTA-8405 and PTA-8406;
   b. is a humanized form of the antibody of (a);
   c. binds to the same epitope as the antibody of (a); or
   d. competes with the antibody of (a) for binding to β2.

3. The antibody of claim 1, wherein the antibody blocks binding of β2 to Notch1 partially.

4. The antibody of claim 1, wherein the antibody binds to the extracellular domain of β2.

5. The antibody of claim 1, wherein the antibody is an antibody fragment selected from a Fab, Fab'-SH, Fv, scFv, or (Fab')2 fragment.

6. The antibody of claim 1, wherein the antibody is human, humanized, or chimeric.

7. The antibody of claim 1, wherein the antibody is an IgG antibody.

8. The antibody of claim 1, wherein the antibody binds to β2 expressed on a cell.

9. The antibody of claim 8, wherein the cell is a cancer cell.

10. The antibody of claim 9, wherein the cancer is selected from the group consisting of colon, duodenum, esophagus, small intestine, liver, pancreas, rectum, stomach, bladder, breast, cervix, kidney, ovary, prostate, testis, uterus, brain, lung, skin, and spleen cancer.

11. The antibody of claim 1, wherein the antibody inhibits epithelial-mesenchymal transition.

12. The antibody of claim 1, wherein the antibody reduces β2-dependent loss of E-cadherin cell surface expression.

13. The antibody of claim 1, wherein the antibody reduces cell migration.

14. The antibody of claim 1, wherein the antibody co-immunoprecipitates β2 and Notch1 from lysates of cells that express β2 and Notch1.

15. A monoclonal antibody that binds to β2, wherein the antibody binds to a polypeptide comprising amino acids 30-159 of SEQ ID NO:2.

16. The antibody of claim 15, wherein the antibody inhibits β2 binding to Notch1.

17. A monoclonal antibody that binds to β2, wherein the antibody competes for binding to β2 with antibody 3D1, 12A9, or 2E3.

18. The antibody of claim 17, wherein binding competition is determined by antibody-cross blocking experiments.

* * * * *

UNITED STATES PATENT AND TRADEMARK OFFICE
CERTIFICATE OF CORRECTION

PATENT NO. : 8,563,695 B2  
APPLICATION NO. : 12/743516  
DATED : October 22, 2013  
INVENTOR(S) : Hongo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 621 days.

Signed and Sealed this

Fifteenth Day of September, 2015

Michelle K. Lee  
*Director of the United States Patent and Trademark Office*

SEQUENCE LISTING

```
<160> NUMBER OF SEQ ID NOS: 11

<210> SEQ ID NO 1
<211> LENGTH: 2556
<212> TYPE: PRT
<213> ORGANISM: Homo sapiens

<400> SEQUENCE: 1

Met Pro Pro Leu Leu Ala Pro Leu Leu Cys Leu Ala Leu Leu Pro
  1               5                  10                  15

Ala Leu Ala Ala Arg Gly Pro Arg Cys Ser Gln Pro Gly Glu Thr
                 20                  25                  30

Cys Leu Asn Gly Gly Lys Cys Glu Ala Ala Asn Gly Thr Glu Ala
                 35                  40                  45

Cys Val Cys Gly Gly Ala Phe Val Gly Pro Arg Cys Gln Asp Pro
                 50                  55                  60

Asn Pro Cys Leu Ser Thr Pro Cys Lys Asn Ala Gly Thr Cys His
                 65                  70                  75
```

```
Val Val Asp Arg Arg Gly Val Ala Asp Tyr Ala Cys Ser Cys Ala
            80                  85                  90

Leu Gly Phe Ser Gly Pro Leu Cys Leu Thr Pro Leu Asp Asn Ala
            95                 100                 105

Cys Leu Thr Asn Pro Cys Arg Asn Gly Gly Thr Cys Asp Leu Leu
           110                 115                 120

Thr Leu Thr Glu Tyr Lys Cys Arg Cys Pro Pro Gly Trp Ser Gly
           125                 130                 135

Lys Ser Cys Gln Gln Ala Asp Pro Cys Ala Ser Asn Pro Cys Ala
           140                 145                 150

Asn Gly Gly Gln Cys Leu Pro Phe Glu Ala Ser Tyr Ile Cys His
           155                 160                 165

Cys Pro Pro Ser Phe His Gly Pro Thr Cys Arg Gln Asp Val Asn
           170                 175                 180

Glu Cys Gly Gln Lys Pro Arg Leu Cys Arg His Gly Gly Thr Cys
           185                 190                 195

His Asn Glu Val Gly Ser Tyr Arg Cys Val Cys Arg Ala Thr His
           200                 205                 210

Thr Gly Pro Asn Cys Glu Arg Pro Tyr Val Pro Cys Ser Pro Ser
           215                 220                 225

Pro Cys Gln Asn Gly Gly Thr Cys Arg Pro Thr Gly Asp Val Thr
           230                 235                 240

His Glu Cys Ala Cys Leu Pro Gly Phe Thr Gly Gln Asn Cys Glu
           245                 250                 255

Glu Asn Ile Asp Asp Cys Pro Gly Asn Asn Cys Lys Asn Gly Gly
           260                 265                 270

Ala Cys Val Asp Gly Val Asn Thr Tyr Asn Cys Pro Cys Pro Pro
           275                 280                 285

Glu Trp Thr Gly Gln Tyr Cys Thr Glu Asp Val Asp Glu Cys Gln
           290                 295                 300

Leu Met Pro Asn Ala Cys Gln Asn Gly Gly Thr Cys His Asn Thr
           305                 310                 315

His Gly Gly Tyr Asn Cys Val Cys Val Asn Gly Trp Thr Gly Glu
           320                 325                 330

Asp Cys Ser Glu Asn Ile Asp Asp Cys Ala Ser Ala Ala Cys Phe
           335                 340                 345

His Gly Ala Thr Cys His Asp Arg Val Ala Ser Phe Tyr Cys Glu
           350                 355                 360

Cys Pro His Gly Arg Thr Gly Leu Leu Cys His Leu Asn Asp Ala
           365                 370                 375

Cys Ile Ser Asn Pro Cys Asn Glu Gly Ser Asn Cys Asp Thr Asn
           380                 385                 390

Pro Val Asn Gly Lys Ala Ile Cys Thr Cys Pro Ser Gly Tyr Thr
           395                 400                 405

Gly Pro Ala Cys Ser Gln Asp Val Asp Glu Cys Ser Leu Gly Ala
           410                 415                 420

Asn Pro Cys Glu His Ala Gly Lys Cys Ile Asn Thr Leu Gly Ser
           425                 430                 435

Phe Glu Cys Gln Cys Leu Gln Gly Tyr Thr Gly Pro Arg Cys Glu
           440                 445                 450

Ile Asp Val Asn Glu Cys Val Ser Asn Pro Cys Gln Asn Asp Ala
           455                 460                 465

Thr Cys Leu Asp Gln Ile Gly Glu Phe Gln Cys Met Cys Met Pro
           470                 475                 480
```

```
Gly Tyr Glu Gly Val His Cys Glu Val Asn Thr Asp Glu Cys Ala
            485                 490                 495

Ser Ser Pro Cys Leu His Asn Gly Arg Cys Leu Asp Lys Ile Asn
            500                 505                 510

Glu Phe Gln Cys Glu Cys Pro Thr Gly Phe Thr Gly His Leu Cys
            515                 520                 525

Gln Tyr Asp Val Asp Glu Cys Ala Ser Thr Pro Cys Lys Asn Gly
            530                 535                 540

Ala Lys Cys Leu Asp Gly Pro Asn Thr Tyr Thr Cys Val Cys Thr
            545                 550                 555

Glu Gly Tyr Thr Gly Thr His Cys Glu Val Asp Ile Asp Glu Cys
            560                 565                 570

Asp Pro Asp Pro Cys His Tyr Gly Ser Cys Lys Asp Gly Val Ala
            575                 580                 585

Thr Phe Thr Cys Leu Cys Arg Pro Gly Tyr Thr Gly His His Cys
            590                 595                 600

Glu Thr Asn Ile Asn Glu Cys Ser Ser Gln Pro Cys Arg Leu Arg
            605                 610                 615

Gly Thr Cys Gln Asp Pro Asp Asn Ala Tyr Leu Cys Phe Cys Leu
            620                 625                 630

Lys Gly Thr Thr Gly Pro Asn Cys Glu Ile Asn Leu Asp Asp Cys
            635                 640                 645

Ala Ser Ser Pro Cys Asp Ser Gly Thr Cys Leu Asp Lys Ile Asp
            650                 655                 660

Gly Tyr Glu Cys Ala Cys Glu Pro Gly Tyr Thr Gly Ser Met Cys
            665                 670                 675

Asn Ser Asn Ile Asp Glu Cys Ala Gly Asn Pro Cys His Asn Gly
            680                 685                 690

Gly Thr Cys Glu Asp Gly Ile Asn Gly Phe Thr Cys Arg Cys Pro
            695                 700                 705

Glu Gly Tyr His Asp Pro Thr Cys Leu Ser Glu Val Asn Glu Cys
            710                 715                 720

Asn Ser Asn Pro Cys Val His Gly Ala Cys Arg Asp Ser Leu Asn
            725                 730                 735

Gly Tyr Lys Cys Asp Cys Asp Pro Gly Trp Ser Gly Thr Asn Cys
            740                 745                 750

Asp Ile Asn Asn Asn Glu Cys Glu Ser Asn Pro Cys Val Asn Gly
            755                 760                 765

Gly Thr Cys Lys Asp Met Thr Ser Gly Ile Val Cys Thr Cys Arg
            770                 775                 780

Glu Gly Phe Ser Gly Pro Asn Cys Gln Thr Asn Ile Asn Glu Cys
            785                 790                 795

Ala Ser Asn Pro Cys Leu Asn Lys Gly Thr Cys Ile Asp Asp Val
            800                 805                 810

Ala Gly Tyr Lys Cys Asn Cys Leu Leu Pro Tyr Thr Gly Ala Thr
            815                 820                 825

Cys Glu Val Val Leu Ala Pro Cys Ala Pro Ser Pro Cys Arg Asn
            830                 835                 840

Gly Gly Glu Cys Arg Gln Ser Glu Asp Tyr Glu Ser Phe Ser Cys
            845                 850                 855

Val Cys Pro Thr Ala Gly Ala Lys Gly Gln Thr Cys Glu Val Asp
            860                 865                 870

Ile Asn Glu Cys Val Leu Ser Pro Cys Arg His Gly Ala Ser Cys
            875                 880                 885
```

-continued

```
Gln Asn Thr His Gly Gly Tyr Arg Cys His Cys Gln Ala Gly Tyr
            890                 895                 900

Ser Gly Arg Asn Cys Glu Thr Asp Ile Asp Asp Cys Arg Pro Asn
        905                 910                 915

Pro Cys His Asn Gly Gly Ser Cys Thr Asp Gly Ile Asn Thr Ala
        920                 925                 930

Phe Cys Asp Cys Leu Pro Gly Phe Arg Gly Thr Phe Cys Glu Glu
        935                 940                 945

Asp Ile Asn Glu Cys Ala Ser Asp Pro Cys Arg Asn Gly Ala Asn
        950                 955                 960

Cys Thr Asp Cys Val Asp Ser Tyr Thr Cys Thr Cys Pro Ala Gly
        965                 970                 975

Phe Ser Gly Ile His Cys Glu Asn Asn Thr Pro Asp Cys Thr Glu
        980                 985                 990

Ser Ser Cys Phe Asn Gly Gly Thr Cys Val Asp Gly Ile Asn Ser
        995                 1000                1005

Phe Thr Cys Leu Cys Pro Pro Gly Phe Thr Gly Ser Tyr Cys Gln
        1010                1015                1020

His Val Val Asn Glu Cys Asp Ser Arg Pro Cys Leu Leu Gly Gly
        1025                1030                1035

Thr Cys Gln Asp Gly Arg Gly Leu His Arg Cys Thr Cys Pro Gln
        1040                1045                1050

Gly Tyr Thr Gly Pro Asn Cys Gln Asn Leu Val His Trp Cys Asp
        1055                1060                1065

Ser Ser Pro Cys Lys Asn Gly Gly Lys Cys Trp Gln Thr His Thr
        1070                1075                1080

Gln Tyr Arg Cys Glu Cys Pro Ser Gly Trp Thr Gly Leu Tyr Cys
        1085                1090                1095

Asp Val Pro Ser Val Ser Cys Glu Val Ala Ala Gln Arg Gln Gly
        1100                1105                1110

Val Asp Val Ala Arg Leu Cys Gln His Gly Gly Leu Cys Val Asp
        1115                1120                1125

Ala Gly Asn Thr His His Cys Arg Cys Gln Ala Gly Tyr Thr Gly
        1130                1135                1140

Ser Tyr Cys Glu Asp Leu Val Asp Glu Cys Ser Pro Ser Pro Cys
        1145                1150                1155

Gln Asn Gly Ala Thr Cys Thr Asp Tyr Leu Gly Gly Tyr Ser Cys
        1160                1165                1170

Lys Cys Val Ala Gly Tyr His Gly Val Asn Cys Ser Glu Glu Ile
        1175                1180                1185

Asp Glu Cys Leu Ser His Pro Cys Gln Asn Gly Gly Thr Cys Leu
        1190                1195                1200

Asp Leu Pro Asn Thr Tyr Lys Cys Ser Cys Pro Arg Gly Thr Gln
        1205                1210                1215

Gly Val His Cys Glu Ile Asn Val Asp Asp Cys Asn Pro Pro Val
        1220                1225                1230

Asp Pro Val Ser Arg Ser Pro Lys Cys Phe Asn Asn Gly Thr Cys
        1235                1240                1245

Val Asp Gln Val Gly Gly Tyr Ser Cys Thr Cys Pro Pro Gly Phe
        1250                1255                1260

Val Gly Glu Arg Cys Glu Gly Asp Val Asn Glu Cys Leu Ser Asn
        1265                1270                1275

Pro Cys Asp Ala Arg Gly Thr Gln Asn Cys Val Gln Arg Val Asn
        1280                1285                1290
```

-continued

```
Asp Phe His Cys Glu Cys Arg Ala Gly His Thr Gly Arg Cys
            1295                1300                1305

Glu Ser Val Ile Asn Gly Cys Lys Gly Lys Pro Cys Lys Asn Gly
            1310                1315                1320

Gly Thr Cys Ala Val Ala Ser Asn Thr Ala Arg Gly Phe Ile Cys
            1325                1330                1335

Lys Cys Pro Ala Gly Phe Glu Gly Ala Thr Cys Glu Asn Asp Ala
            1340                1345                1350

Arg Thr Cys Gly Ser Leu Arg Cys Leu Asn Gly Gly Thr Cys Ile
            1355                1360                1365

Ser Gly Pro Arg Ser Pro Thr Cys Leu Cys Leu Gly Pro Phe Thr
            1370                1375                1380

Gly Pro Glu Cys Gln Phe Pro Ala Ser Ser Pro Cys Leu Gly Gly
            1385                1390                1395

Asn Pro Cys Tyr Asn Gln Gly Thr Cys Glu Pro Thr Ser Glu Ser
            1400                1405                1410

Pro Phe Tyr Arg Cys Leu Cys Pro Ala Lys Phe Asn Gly Leu Leu
            1415                1420                1425

Cys His Ile Leu Asp Tyr Ser Phe Gly Gly Gly Ala Gly Arg Asp
            1430                1435                1440

Ile Pro Pro Pro Leu Ile Glu Glu Ala Cys Glu Leu Pro Glu Cys
            1445                1450                1455

Gln Glu Asp Ala Gly Asn Lys Val Cys Ser Leu Gln Cys Asn Asn
            1460                1465                1470

His Ala Cys Gly Trp Asp Gly Gly Asp Cys Ser Leu Asn Phe Asn
            1475                1480                1485

Asp Pro Trp Lys Asn Cys Thr Gln Ser Leu Gln Cys Trp Lys Tyr
            1490                1495                1500

Phe Ser Asp Gly His Cys Asp Ser Gln Cys Asn Ser Ala Gly Cys
            1505                1510                1515

Leu Phe Asp Gly Phe Asp Cys Gln Arg Ala Glu Gly Gln Cys Asn
            1520                1525                1530

Pro Leu Tyr Asp Gln Tyr Cys Lys Asp His Phe Ser Asp Gly His
            1535                1540                1545

Cys Asp Gln Gly Cys Asn Ser Ala Glu Cys Glu Trp Asp Gly Leu
            1550                1555                1560

Asp Cys Ala Glu His Val Pro Glu Arg Leu Ala Ala Gly Thr Leu
            1565                1570                1575

Val Val Val Val Leu Met Pro Pro Glu Gln Leu Arg Asn Ser Ser
            1580                1585                1590

Phe His Phe Leu Arg Glu Leu Ser Arg Val Leu His Thr Asn Val
            1595                1600                1605

Val Phe Lys Arg Asp Ala His Gly Gln Gln Met Ile Phe Pro Tyr
            1610                1615                1620

Tyr Gly Arg Glu Glu Glu Leu Arg Lys His Pro Ile Lys Arg Ala
            1625                1630                1635

Ala Glu Gly Trp Ala Ala Pro Asp Ala Leu Leu Gly Gln Val Lys
            1640                1645                1650

Ala Ser Leu Leu Pro Gly Gly Ser Glu Gly Gly Arg Arg Arg Arg
            1655                1660                1665

Glu Leu Asp Pro Met Asp Val Arg Gly Ser Ile Val Tyr Leu Glu
            1670                1675                1680

Ile Asp Asn Arg Gln Cys Val Gln Ala Ser Ser Gln Cys Phe Gln
            1685                1690                1695
```

```
Ser Ala Thr Asp Val Ala Ala Phe Leu Gly Ala Leu Ala Ser Leu
            1700                1705                1710

Gly Ser Leu Asn Ile Pro Tyr Lys Ile Glu Ala Val Gln Ser Glu
            1715                1720                1725

Thr Val Glu Pro Pro Pro Ala Gln Leu His Phe Met Tyr Val
            1730                1735                1740

Ala Ala Ala Ala Phe Val Leu Leu Phe Phe Val Gly Cys Gly Val
            1745                1750                1755

Leu Leu Ser Arg Lys Arg Arg Arg Gln His Gly Gln Leu Trp Phe
            1760                1765                1770

Pro Glu Gly Phe Lys Val Ser Glu Ala Ser Lys Lys Arg Arg
            1775                1780                1785

Glu Pro Leu Gly Glu Asp Ser Val Gly Leu Lys Pro Leu Lys Asn
            1790                1795                1800

Ala Ser Asp Gly Ala Leu Met Asp Asp Asn Gln Asn Glu Trp Gly
            1805                1810                1815

Asp Glu Asp Leu Glu Thr Lys Lys Phe Arg Phe Glu Glu Pro Val
            1820                1825                1830

Val Leu Pro Asp Leu Asp Asp Gln Thr Asp His Arg Gln Trp Thr
            1835                1840                1845

Gln Gln His Leu Asp Ala Ala Asp Leu Arg Met Ser Ala Met Ala
            1850                1855                1860

Pro Thr Pro Pro Gln Gly Glu Val Asp Ala Asp Cys Met Asp Val
            1865                1870                1875

Asn Val Arg Gly Pro Asp Gly Phe Thr Pro Leu Met Ile Ala Ser
            1880                1885                1890

Cys Ser Gly Gly Gly Leu Glu Thr Gly Asn Ser Glu Glu Glu Glu
            1895                1900                1905

Asp Ala Pro Ala Val Ile Ser Asp Phe Ile Tyr Gln Gly Ala Ser
            1910                1915                1920

Leu His Asn Gln Thr Asp Arg Thr Gly Glu Thr Ala Leu His Leu
            1925                1930                1935

Ala Ala Arg Tyr Ser Arg Ser Asp Ala Ala Lys Arg Leu Leu Glu
            1940                1945                1950

Ala Ser Ala Asp Ala Asn Ile Gln Asp Asn Met Gly Arg Thr Pro
            1955                1960                1965

Leu His Ala Ala Val Ser Ala Asp Ala Gln Gly Val Phe Gln Ile
            1970                1975                1980

Leu Ile Arg Asn Arg Ala Thr Asp Leu Asp Ala Arg Met His Asp
            1985                1990                1995

Gly Thr Thr Pro Leu Ile Leu Ala Ala Arg Leu Ala Val Glu Gly
            2000                2005                2010

Met Leu Glu Asp Leu Ile Asn Ser His Ala Asp Val Asn Ala Val
            2015                2020                2025

Asp Asp Leu Gly Lys Ser Ala Leu His Trp Ala Ala Ala Val Asn
            2030                2035                2040

Asn Val Asp Ala Ala Val Val Leu Leu Lys Asn Gly Ala Asn Lys
            2045                2050                2055

Asp Met Gln Asn Asn Arg Glu Glu Thr Pro Leu Phe Leu Ala Ala
            2060                2065                2070

Arg Glu Gly Ser Tyr Glu Thr Ala Lys Val Leu Leu Asp His Phe
            2075                2080                2085

Ala Asn Arg Asp Ile Thr Asp His Met Asp Arg Leu Pro Arg Asp
            2090                2095                2100
```

```
Ile Ala Gln Glu Arg Met His His Asp Ile Val Arg Leu Leu Asp
            2105                2110                2115

Glu Tyr Asn Leu Val Arg Ser Pro Gln Leu His Gly Ala Pro Leu
            2120                2125                2130

Gly Gly Thr Pro Thr Leu Ser Pro Pro Leu Cys Ser Pro Asn Gly
            2135                2140                2145

Tyr Leu Gly Ser Leu Lys Pro Gly Val Gln Gly Lys Lys Val Arg
            2150                2155                2160

Lys Pro Ser Ser Lys Gly Leu Ala Cys Gly Ser Lys Glu Ala Lys
            2165                2170                2175

Asp Leu Lys Ala Arg Arg Lys Lys Ser Gln Asp Gly Lys Gly Cys
            2180                2185                2190

Leu Leu Asp Ser Ser Gly Met Leu Ser Pro Val Asp Ser Leu Glu
            2195                2200                2205

Ser Pro His Gly Tyr Leu Ser Asp Val Ala Ser Pro Leu Leu
            2210                2215                2220

Pro Ser Pro Phe Gln Gln Ser Pro Ser Val Pro Leu Asn His Leu
            2225                2230                2235

Pro Gly Met Pro Asp Thr His Leu Gly Ile Gly His Leu Asn Val
            2240                2245                2250

Ala Ala Lys Pro Glu Met Ala Ala Leu Gly Gly Gly Gly Arg Leu
            2255                2260                2265

Ala Phe Glu Thr Gly Pro Pro Arg Leu Ser His Leu Pro Val Ala
            2270                2275                2280

Ser Gly Thr Ser Thr Val Leu Gly Ser Ser Gly Gly Ala Leu
            2285                2290                2295

Asn Phe Thr Val Gly Gly Ser Thr Ser Leu Asn Gly Gln Cys Glu
            2300                2305                2310

Trp Leu Ser Arg Leu Gln Ser Gly Met Val Pro Asn Gln Tyr Asn
            2315                2320                2325

Pro Leu Arg Gly Ser Val Ala Pro Gly Pro Leu Ser Thr Gln Ala
            2330                2335                2340

Pro Ser Leu Gln His Gly Met Val Gly Pro Leu His Ser Ser Leu
            2345                2350                2355

Ala Ala Ser Ala Leu Ser Gln Met Met Ser Tyr Gln Gly Leu Pro
            2360                2365                2370

Ser Thr Arg Leu Ala Thr Gln Pro His Leu Val Gln Thr Gln Gln
            2375                2380                2385

Val Gln Pro Gln Asn Leu Gln Met Gln Gln Gln Asn Leu Gln Pro
            2390                2395                2400

Ala Asn Ile Gln Gln Gln Ser Leu Gln Pro Pro Pro Pro Pro
            2405                2410                2415

Pro Gln Pro His Leu Gly Val Ser Ser Ala Ala Ser Gly His Leu
            2420                2425                2430

Gly Arg Ser Phe Leu Ser Gly Glu Pro Ser Gln Ala Asp Val Gln
            2435                2440                2445

Pro Leu Gly Pro Ser Ser Leu Ala Val His Thr Ile Leu Pro Gln
            2450                2455                2460

Glu Ser Pro Ala Leu Pro Thr Ser Leu Pro Ser Ser Leu Val Pro
            2465                2470                2475

Pro Val Thr Ala Ala Gln Phe Leu Thr Pro Pro Ser Gln His Ser
            2480                2485                2490

Tyr Ser Ser Pro Val Asp Asn Thr Pro Ser His Gln Leu Gln Val
            2495                2500                2505
```

```
Pro Glu His Pro Phe Leu Thr Pro Ser Pro Glu Ser Pro Asp Gln
            2510                2515                2520

Trp Ser Ser Ser Pro His Ser Asn Val Ser Asp Trp Ser Glu
            2525                2530                2535

Gly Val Ser Ser Pro Pro Thr Ser Met Gln Ser Gln Ile Ala Arg
            2540                2545                2550

Ile Pro Glu Ala Phe Lys
            2555

<210> SEQ ID NO 2
<211> LENGTH: 215
<212> TYPE: PRT
<213> ORGANISM: Homo sapiens

<400> SEQUENCE: 2

Met His Arg Asp Ala Trp Leu Pro Arg Pro Ala Phe Ser Leu Thr
  1               5                  10                  15

Gly Leu Ser Leu Phe Phe Ser Leu Val Pro Pro Gly Arg Ser Met
                 20                  25                  30

Glu Val Thr Val Pro Ala Thr Leu Asn Val Leu Asn Gly Ser Asp
                 35                  40                  45

Ala Arg Leu Pro Cys Thr Phe Asn Ser Cys Tyr Thr Val Asn His
                 50                  55                  60

Lys Gln Phe Ser Leu Asn Trp Thr Tyr Gln Glu Cys Asn Asn Cys
                 65                  70                  75

Ser Glu Glu Met Phe Leu Gln Phe Arg Met Lys Ile Ile Asn Leu
                 80                  85                  90

Lys Leu Glu Arg Phe Gln Asp Arg Val Glu Phe Ser Gly Asn Pro
                 95                 100                 105

Ser Lys Tyr Asp Val Ser Val Met Leu Arg Asn Val Gln Pro Glu
                110                 115                 120

Asp Glu Gly Ile Tyr Asn Cys Tyr Ile Met Asn Pro Pro Asp Arg
                125                 130                 135

His Arg Gly His Gly Lys Ile His Leu Gln Val Leu Met Glu Glu
                140                 145                 150

Pro Pro Glu Arg Asp Ser Thr Val Ala Val Ile Val Gly Ala Ser
                155                 160                 165

Val Gly Gly Phe Leu Ala Val Val Ile Leu Val Leu Met Val Val
                170                 175                 180

Lys Cys Val Arg Arg Lys Lys Glu Gln Lys Leu Ser Thr Asp Asp
                185                 190                 195

Leu Lys Thr Glu Glu Glu Gly Lys Thr Asp Gly Glu Gly Asn Pro
                200                 205                 210

Asp Asp Gly Ala Lys
                215

<210> SEQ ID NO 3
<211> LENGTH: 21
<212> TYPE: RNA
<213> ORGANISM: Artificial sequence
<220> FEATURE:
<223> OTHER INFORMATION: Sequence is synthesized

<400> SEQUENCE: 3
caacgaaucu acccauauuu u                                        21
```

```
<210> SEQ ID NO 4
<211> LENGTH: 21
<212> TYPE: RNA
<213> ORGANISM: Artificial sequence
<220> FEATURE:
<223> OTHER INFORMATION: Sequence is synthesized

<400> SEQUENCE: 4
gcgacgagcu ggacuccaau u                                                   21

<210> SEQ ID NO 5
<211> LENGTH: 21
<212> TYPE: RNA
<213> ORGANISM: Artificial sequence
<220> FEATURE:
<223> OTHER INFORMATION: Sequence is synthesized

<400> SEQUENCE: 5
gcgacaaggu guugacguuu u                                                   21

<210> SEQ ID NO 6
<211> LENGTH: 21
<212> TYPE: RNA
<213> ORGANISM: Artificial sequence
<220> FEATURE:
<223> OTHER INFORMATION: Sequence is synthesized

<400> SEQUENCE: 6
cugcagacgc agcgggucau u                                                   21

<210> SEQ ID NO 7
<211> LENGTH: 21
<212> TYPE: RNA
<213> ORGANISM: Artificial sequence
<220> FEATURE:
<223> OTHER INFORMATION: Sequence is synthesized

<400> SEQUENCE: 7
ggaguccgca gucuuacgau u                                                   21

<210> SEQ ID NO 8
<211> LENGTH: 21
<212> TYPE: RNA
<213> ORGANISM: Artificial sequence
<220> FEATURE:
<223> OTHER INFORMATION: Sequence is synthesized

<400> SEQUENCE: 8
gagcaagauu cagacccucu u                                                   21

<210> SEQ ID NO 9
<211> LENGTH: 21
<212> TYPE: RNA
<213> ORGANISM: Artificial sequence
<220> FEATURE:
<223> OTHER INFORMATION: Sequence is synthesized

<400> SEQUENCE: 9
gaugcgagau cgacgucaau u                                                   21

<210> SEQ ID NO 10
<211> LENGTH: 21
<212> TYPE: RNA
<213> ORGANISM: Artificial sequence
<220> FEATURE:
<223> OTHER INFORMATION: Sequence is synthesized
```

-continued

```
<400> SEQUENCE: 10
gaacggggcu aacaaagauu  u                                              21

<210> SEQ ID NO 11
<211> LENGTH: 21
<212> TYPE: RNA
<213> ORGANISM: Artificial sequence
<220> FEATURE:
<223> OTHER INFORMATION: Sequence is synthesized

<400> SEQUENCE: 11
gcaaggacca cuucagcgau  u                                              21
```